(12) United States Patent
O'Neill

(10) Patent No.: US 10,889,803 B2
(45) Date of Patent: Jan. 12, 2021

(54) TRANSGENIC MACROPHAGES, CHIMERIC ANTIGEN RECEPTORS, AND ASSOCIATED METHODS

(71) Applicant: Thunder Biotech, Inc., Provo, UT (US)

(72) Inventor: Kim Leslie O'Neill, Provo, UT (US)

(73) Assignee: Thunder Biotech, Inc, Alpine, UT (US)

( * ) Notice: Subject to any disclaimer, the term of this patent is extended or adjusted under 35 U.S.C. 154(b) by 0 days.

(21) Appl. No.: 16/572,368

(22) Filed: Sep. 16, 2019

(65) Prior Publication Data

US 2020/0002676 A1 Jan. 2, 2020

Related U.S. Application Data

(63) Continuation of application No. 15/597,822, filed on May 17, 2017, now Pat. No. 10,415,017.

(51) Int. Cl.
| | |
|---|---|
| *C12N 5/0786* | (2010.01) |
| *C07K 14/705* | (2006.01) |
| *C07K 16/30* | (2006.01) |
| *C07K 16/40* | (2006.01) |

(52) U.S. Cl.
CPC .......... *C12N 5/0645* (2013.01); *C07K 14/705* (2013.01); *C07K 16/30* (2013.01); *C07K 16/40* (2013.01); *C12Y 207/01021* (2013.01); *C07K 2317/622* (2013.01); *C07K 2319/30* (2013.01); *C07K 2319/32* (2013.01); *C07K 2319/33* (2013.01); *C07K 2319/70* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 499,629 | A | 6/1893 | Ellis |
| 906,682 | A | 12/1908 | Birkeland |
| 911,993 | A | 2/1909 | Jacobs |
| 916,381 | A | 3/1909 | Webster |
| 5,359,046 | A | 10/1994 | Capon et al. |
| 8,906,682 | B2 | 12/2014 | June et al. |
| 8,911,993 | B2 | 12/2014 | June et al. |
| 8,916,381 | B1 | 12/2014 | June et al. |
| 9,499,629 | B2 | 11/2016 | June et al. |
| 2010/0143290 | A1 | 6/2010 | Lallatin |
| 2010/0266495 | A1 | 10/2010 | O'Neill |
| 2011/0176996 | A1 | 7/2011 | O'Neill et al. |
| 2018/0244748 | A1 | 8/2018 | Gill et al. |

FOREIGN PATENT DOCUMENTS

| | | |
|---|---|---|
| WO | 2010065763 A1 | 6/2010 |
| WO | 2011082345 A2 | 7/2011 |
| WO | 2015063069 A1 | 5/2015 |
| WO | 2016033331 A1 | 3/2016 |
| WO | 2017025944 A2 | 2/2017 |
| WO | WO2017019848 A1 | 2/2017 |

OTHER PUBLICATIONS

Gunaydin, et al. (2014) "Mutations in Toll-Like Receptor 3 Are Associated with Elevated Levels of Rotavirus-Specific IgG Antibodies in IgA-Deficient but Not IgA-Sufficient Individuals", Cancer and Vaccine Immunology, 21(3): 298-301 (Year: 2014).*
Sarlus, et al. (2017) "Micrglia in Alzheimer's disease", The Journal of Clinical Investigation, 127(9): 3240-49. (Year: 2017).*
Wynn, et al. (2015) "Macrophages in Tissue Repair, Regeneration and Fibrosis", Immunity, 44: 450-462. (Year: 2015).*
Bulut, Chlamydia Heat Shock Protein 60 Activates Macrophages and Endothelial Cells Through Toll-Like Receptor 4 and MD2 in a MyD88-Dependent Pathway, 2002, The Journal of Immunology 168:1435-1440, American Association of Immunologists, Inc.
Darcy et al., Manipulating Immune Cells for Adoptive Immunotherapy of Cancer, Apr. 1, 2014, Current Opinion Immunology, vol. 27: 46-52.
Levin et al, Evaluation of macrophage-specific promoters using lentiviral delivery in mice, 2012, Gene Therapy, Macmillan Publishers Limited 168:1435-1440.
Palaga et al, Notch signaling is activated by TLR stimulation and regulates macrophage functions, 2008, European Journal of Immunology 38:174-183.
"Paul et al., Targeted macrophage cytotoxicity using a nonreplicative live vector expressing a tumor-specific single-chain variable region fragment, Jul. 1, 2000, Human Gene Therapy, Mary Ann Liebert, Inc. Publichers, US, vol. 1, No. 10."
PCT International Search Report and Written Opinion, PCT/IB2016/056140, dated Mar. 17, 2017, 17 pages.
Sinha et al., Reduction of Myeloid-Derived Suppressor Cells and Induction of MI Macrophages Facilitate the Rejection of Established Metastatic Disease, 2005, The Journal of Immunology 174:636-645.

(Continued)

*Primary Examiner* — Robert M Kelly

(74) *Attorney, Agent, or Firm* — Patent Law Works, LLP

(57) ABSTRACT

Described herein are chimeric receptors. Chimeric receptors comprise a cytoplasmic domain; a transmembrane domain; and an extracellular domain. In embodiments, the cytoplasmic domain comprises a cytoplasmic portion of a receptor that when activated polarizes a macrophage. In further embodiments, a wild-type protein comprising the cytoplasmic portion does not comprise the extracellular domain of the chimeric receptor. In embodiments, the binding of a ligand to the extracellular domain of the chimeric receptor activates the intracellular portion of the chimeric receptor. Activation of the intracellular portion of the chimeric receptor may polarize the macrophage into an M1 or M2 macrophage.

12 Claims, 30 Drawing Sheets

Specification includes a Sequence Listing.

(56) References Cited

OTHER PUBLICATIONS

Wang et al., Notch Signaling Determines the M1 versus M2 Polarization of Macrophages in Antitumor Immune Responses, 2010, Cancer Res, 70: 4840-4849.

Yong et al, Using Electroporation to Determine Function of a Chimeric Antigen Receptor in T Cell and Macrophage Cell Lines, The Open Gene Therapey Journal, vol. 5 No. 1, Aug. 23, 2013, pp. 1-11.

Zhang F et al., "A Monoclonal Antibody Specific for Human Thymidine Kinase 1," Jul. 20, 2004, Hybridoma, Liebert, New York, NY, US, vol. 1: 25-34.

PCT International Search Report and Written Opinion, PCT/US2017/033039, dated Jan. 30, 2018, 10 pages.

\* cited by examiner

| SP | TK1-ScFv | GS-Linker | TLR4 Transmembrane domain | Toll like receptor 4 cytosolic domain |
|---|---|---|---|---|

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSIGVSVLSVLV

VSVVAVLVYKFYFHLMLLAGCIKYGRGENIYDAFVIYSSQDEDWVRNELV

KNLEEGVPPFQLCLHYRDFIPGVAIAANIIHEGFHKSRKVIVVVSQHFIQ

SRWCIFEYEIAQTWQFLSSRAGIIFIVLQKVEKTLLRQQVELYRLLSRNT

FIG. 1B

| SP | TK1-ScFv | GS-Linker | LRR 5 a.a. Short hinge | TLR4 Transmembrane domain | Toll like receptor 4 cytosolic domain |
|---|---|---|---|---|---|

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSMNKTIIGVSV

LSVLVVSVVAVLVYKFYFHLMLLAGCIKYGRGENIYDAFVIYSSQDEDWV

RNELVKNLEEGVPPFQLCLHYRDFIPGVAIAANIIHEGFHKSRKVIVVVS

QHFIQSRWCIFEYEIAQTWQFLSSRAGIIFIVLQKVEKTLLRQQVELYRL

LSRNTYLEWEDSVLGRHIFWRRLRKALLDGKSWNPEGTVGTGCNWQEATS

FIG. 2B

| SP | TK1-ScFv | GS-Linker | LRR long hinge | TLR4 Transmembrane domain | Toll like receptor 4 cytosolic domain |

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSNDFACTCEHQ

SFLQWIKDQRQLLVEVERMECATPSDKQGMPVLSLNITCQMNKTIIGVSV

LSVLVVSVVAVLVYKFYFHLMLLAGCIKYGRGENIYDAFVIYSSQDEDWV

RNELVKNLEEGVPPFQLCLHYRDFIPGVAIAANIIHEGFHKSRKVIVVVS

QHFIQSRWCIFEYEIAQTWQFLSSRAGIIFIVLQKVEKTLLRQQVELYRL

LSRNTYLEWEDSVLGRHIFWRRLRKALLDGKSWNPEGTVGTGCNWQEATS

| SP | TK1-ScFv | GS-Linker | IgG4 short hinge | TLR4 Transmembrane domain | Toll like receptor 4 cytosolic domain |

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSESKYGPPCPP

CPIGVSVLSVLVVSVVAVLVYKFYFHLMLLAGCIKYGRGENIYDAFVIYS

SQDEDWVRNELVKNLEEGVPPFQLCLHYRDFIPGVAIAANIIHEGFHKSR

KVIVVVSQHFIQSRWCIFEYEIAQTWQFLSSRAGIIFIVLQKVEKTLLRQ

QVELYRLLSRNTYLEWEDSVLGRHIFWRRLRKALLDGKSWNPEGTVGTGC

NWQEATSI
```

FIG. 4B

| SP | TK1-ScFv | GS-Linker | IgG 119 aa medium hinge | TLR4 Transmembrane domain | Toll like receptor 4 cytosolic domain |

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSESKYGPPCPP

CPGQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHYTQ

KSLSLSLGKIGVSVLSVLVVSVVAVLVYKFYFHLMLLAGCIKYGRGENIY

DAFVIYSSQDEDWVRNELVKNLEEGVPPFQLCLHYRDFIPGVAIAANIIH

EGFHKSRKVIVVVSQHFIQSRWCIFEYEIAQTWQFLSSRAGIIFIVLQKV

EKTLLRQQVELYRLLSRNTYLEWEDSVLGRHIFWRRLRKALLDGKSWNPE

GTVGTGCNWQEATSI

FIG. 5B

| SP | TK1-ScFv | GS-Linker | IgG4 long hinge | TLR4 Transmembrane domain | Toll like receptor 4 cytosolic domain |

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSESKYGPPCPP

CPAPPVAGPSVFLFPPKPKDTLMISRTPEVTCVVVDVSQEDPEVQFNWYV

DGVEVHNAKTKPREEQFQSTYRVVSVLTVLHQDWLNGKEYKCKVSNKGLP

SSIEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSVMH

EALHNHYTQKSLSLSLGKIGVSVLSVLVVSVVAVLVYKFYFHLMLLAGCI

KYGRGENIYDAFVIYSSQDEDWVRNELVKNLEEGVPPFQLCLHYRDFIPG

VAIAANIIHEGFHKSRKVIVVVSQHFIQSRWCIFEYEIAQTWQFLSSRAG

IIFIVLQKVEKTLLRQQVELYRLLSRNTYLEWEDSVLGRHIFWRRLRKAL

LDGKSWNPEGTVGTGCNWQEATSI

FIG. 6B

| SP | TK1-ScFv | GS-Linker | Mutated CD8 hinge cysteines to serines | TLR4 Transmembrane domain | Toll like receptor 4 cytosolic domain |

FIG. 7A

```
1         10        20        30        40        50
|         |         |         |         |         |
MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSSALSNSIMYF

SHFVPVFLPAKPTTTPAPRPPTPAPTIASQPLSLRPEASRPAAGGAVHTR

GLDFASDIIGVSVLSVLVVSVVAVLVYKFYFHLMLLAGCIKYGRGENIYD

AFVIYSSQDEDWVRNELVKNLEEGVPPFQLCLHYRDFIPGVAIAANIIHE

GFHKSRKVIVVVSQHFIQSRWCIFEYEIAQTWQFLSSRAGIIFIVLQKVE

KTLLRQQVELYRLLSRNTYLEWEDSVLGRHIFWRRLRKALLDGKSWNPEG

TVGTGCNWQEATSI
```

FIG. 7B

| SP | TK1-ScFv | GS-Linker | Portion of CD8 hinge | TLR4 Transmembrane domain | Toll like receptor 4 cytosolic domain |
|---|---|---|---|---|---|

FIG. 8A

```
1         10        20        30        40        50
|         |         |         |         |         |
MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSSALSNSIMYF

SHFVPVFLPAKPTTTPAPRPPTPAPTIASQPLSLRPEACRPAAGGAVHTR

GLDFACDIIGVSVLSVLVVSVVAVLVYKFYFHLMLLAGCIKYGRGENIYD

AFVIYSSQDEDWVRNELVKNLEEGVPPFQLCLHYRDFIPGVAIAANIIHE

GFHKSRKVIVVVSQHFIQSRWCIFEYEIAQTWQFLSSRAGIIFIVLQKVE

KTLLRQQVELYRLLSRNTYLEWEDSVLGRHIFWRRLRKALLDGKSWNPEG

TVGTGCNWQEATSI
```

FIG. 8B

| SP | TK1-ScFv | GS-Linker | FCGR3A Transmembrane | FCGR3A-Cytosolic domain | FCER1G Cytosolic domain |
|---|---|---|---|---|---|

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQSSLTSEDTAVYYCA

KVGYGHWYFDVWGAGTTVTVSSVDLGGGGSGGGGSGGGGSVSFCLVMVLL

FAVDTGLYFSVKTNIRSSTRDWKDHKFKWRKDPQDKRLKIQVRKAAITSY

EKSDGVYTGLSTRNQETYETLKHEKPPQ
```

FIG. 9B

| SP | TK1-ScFv | GS-Linker | Modified CD8a hinge Cysteines to Serines | FCGR3A Transmembrane | FCGR3A-Cytosolic domain | FCER1G Cytosolic domain |

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSSALSNSIMYF

SHFVPVFLPAKPTTTPAPRPPTPAPTIASQPLSLRPEASRPAAGGAVHTR

GLDFASDIVSFCLVMVLLFAVDTGLYFSVKTNIRSSTRDWKDHKFKWRKD

PQDKRLKIQVRKAAITSYEKSDGVYTGLSTRNQETYETLKHEKPPQ

FIG. 10B

| SP | TK1-ScFv | GS-Linker | Portion of CD8a hinge | FCGR3A Transmembrane | FCGR3A-Cytosolic domain | FCER1G Cytosolic domain |

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSSALSNSIMYF

SHFVPVFLPAKPTTTPAPRPPTPAPTIASQPLSLRPEACRPAAGGAVHTR

GLDFACDIVSFCLVMVLLFAVDTGLYFSVKTNIRSSTRDWKDHKFKWRKD

PQDKRLKIQVRKAAITSYEKSDGVYTGLSTRNQETYETLKHEKPPQ
```

FIG. 11B

| SP | TK1-ScFv | GS-Linker | IgG4 short hinge | FCGR3A Transmembrane | FCGR3A-Cytosolic domain | FCER1G Cytosolic domain |

FIG. 12A

```
1         10        20        30        40        50
|         |         |         |         |         |
MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSESKYGPPCPP

CPIVSFCLVMVLLFAVDTGLYFSVKTNIRSSTRDWKDHKFKWRKDPQDKR

LKIQVRKAAITSYEKSDGVYTGLSTRNQETYETLKHEKPPQ
```

FIG. 12B

| SP | TK1-ScFv | GS-Linker | IgG4 119 aa hinge | FCGR3A Transmembrane | FCGR3A-Cytosolic domain | FCER1G Cytosolic domain |

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSESKYGPPCPP

CPGQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHYTQ

KSLSLSLGKVSFCLVMVLLFAVDTGLYFSVKTNIRSSTRDWKDHKFKWRK

DPQDKRLKIQVRKAAITSYEKSDGVYTGLSTRNQETYETLKHEKPPQ
```

FIG. 13B

| SP | TK1-ScFv | GS-Linker | IgG4 long hinge | FCGR3A Transmembrane | FCGR3A-Cytosolic domain | FCER1G Cytosolic domain |

FIG. 14A

```
1         10        20        30        40        50
|         |         |         |         |         |
MDFQVQIISFLLISASVIMSRGQIVLSQSPAILSASPGEKVTMTCRASSS
VSYMHFYQQKPGSSPKPWIYATSNLASGVPARFSGSGSGTSFSLTISRVE
AEDAATYYCQQWSSNPPTFGSGTKLEIKSGGGGSGGGGSGGGGSMAVVTG
VNSEVQLQQSGAELVKPGASVKLSCTASGFNIKDTYIHWVKQRPEQGLEW
IGRIDPANGNTKYDPKFQGKATITTDTSFNTAYLQLSSLTSEDTAVYYCA
KVGYGHWYFDVWGAGTTVTVSSVDLGGGGSGGGGSGGGGSESKYGPPCPP
CPAPPVAGPSVFLFPPKPKDTLMISRTPEVTCVVVDVSQEDPEVQFNWYV
DGVEVHNAKTKPREEQFQSTYRVVSVLTVLHQDWLNGKEYKCKVSNKGLP
SSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMH
EALHNHYTQKSLSLSLGKIVSFCLVMVLLFAVDTGLYFSVKTNIRSSTRD
WKDHKFKWRKDPQDKRLKIQVRKAAITSYEKSDGVYTGLSTRNQETYETL
KHEKPPQ
```

FIG. 14B

| SP | TK1-ScFv | GS-Linker | FCGR2A Transmembrane | FCGR2A Cytosolic domain |
|---|---|---|---|---|

MDFQVQIISFLLISASVIMSRGQIVLSQSPAILSASPGEKVTMTCRASSS
VSYMHFYQQKPGSSPKPWIYATSNLASGVPARFSGSGSGTSFSLTISRVE
AEDAATYYCQQWSSNPPTFGSGTKLEIKSGGGGSGGGGSGGGGSMAVVTG
VNSEVQLQQSGAELVKPGASVKLSCTASGFNIKDTYIHWVKQRPEQGLEW
IGRIDPANGNTKYDPKFQGKATITTDTSFNTAYLQLSSLTSEDTAVYYCA
KVGYGHWYFDVWGAGTTVTVSSVDLGGGGSGGGGSGGGGSIIVAVVIATA
VAAIVAAVVALIYCRKKRISANSTDPVKAAQFEPPGRQMIAIRKRQLEET
NNDYETADGGYMTLNPRAPTDDDKNIYLTLPPNDHVSNN
```

FIG. 15B

| SP | TK1-ScFv | GS-Linker | Modified CD8a hinge Cysteines to Serines | FCGR2A Transmembrane | FCGR2A Cytosolic domain |
|---|---|---|---|---|---|

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSSALSNSIMYF

SHFVPVFLPAKPTTTPAPRPPTPAPTIASQPLSLRPEASRPAAGGAVHTR

GLDFASDIIIVAVVIATAVAAIVAAVVALIYCRKKRISANSTDPVKAAQF

EPPGRQMIAIRKRQLEETNNDYETADGGYMTLNPRAPTDDDKNIYLTLPP

NDHVSNN
```

FIG. 16B

| SP | TK1-ScFv | GS-Linker | Portion of CD8a hinge | FCGR2A Transmembrane | FCGR2A Cytosolic domain |
|---|---|---|---|---|---|

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSSALSNSIMYF

SHFVPVFLPAKPTTTPAPRPPTPAPTIASQPLSLRPEACRPAAGGAVHTR

GLDFACDIIIVAVVIATAVAAIVAAVVALIYCRKKRISANSTDPVKAAQF

EPPGRQMIAIRKRQLEETNNDYETADGGYMTLNPRAPTDDDKNIYLTLPP

NDHVSNN
```

FIG. 17B

| SP | TK1-ScFv | GS-Linker | IgG4 short hinge | FCGR2A Transmembrane | FCGR2A Cytosolic domain |

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSESKYGPPCPP

CPIIIVAVVIATAVAAIVAAVVALIYCRKKRISANSTDPVKAAQFEPPGR

QMIAIRKRQLEETNNDYETADGGYMTLNPRAPTDDDKNIYLTLPPNDHVN

SNN

FIG. 18B

| SP | TK1-ScFv | GS-Linker | IgG4 119 aa hinge | FCGR2A Transmembrane | FCGR2A Cytosolic domain |
|---|---|---|---|---|---|

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSESKYGPPCPP

CPGQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHYTQ

KSLSLSLGKIIVAVVIATAVAAIVAAVVALIYCRKKRISANSTDPVKAAQ

FEPPGRQMIAIRKRQLEETNNDYETADGGYMTLNPRAPTDDDKNIYLTLP

PNDHVNSNN
```

FIG. 19B

| SP | TK1-ScFv | GS-Linker | IgG4 long hinge | FCGR2A Transmembrane | FCGR2A Cytosolic domain |

MDFQVQIISFLLISASVIMSRGQIVLSQSPAILSASPGEKVTMTCRASSS

VSYMHFYQQKPGSSPKPWIYATSNLASGVPARFSGSGSGTSFSLTISRVE

AEDAATYYCQQWSSNPPTFGSGTKLEIKSGGGGSGGGGSGGGGSMAVVTG

VNSEVQLQQSGAELVKPGASVKLSCTASGFNIKDTYIHWVKQRPEQGLEW

IGRIDPANGNTKYDPKFQGKATITTDTSFNTAYLQLSSLTSEDTAVYYCA

KVGYGHWYFDVWGAGTTVTVSSVDLGGGGSGGGGSGGGGSESKYGPPCPP

CPAPPVAGPSVFLFPPKPKDTLMISRTPEVTCVVVDVSQEDPEVQFNWYV

DGVEVHNAKTKPREEQFQSTYRVVSVLTVLHQDWLNGKEYKCKVSNKGLP

SSIEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSVMH

EALHNHYTQKSLSLSLGKIIIVAVVIATAVAAIVAAVVALIYCRKKRISA

NSTDPVKAAQFEPPGRQMIAIRKRQLEETNNDYETADGGYMTLNPRAPTD

DDKNIYLTLPPNDHVSNN

FIG. 20B

TRANSGENIC MACROPHAGES, CHIMERIC ANTIGEN RECEPTORS, AND ASSOCIATED METHODS

CROSS-REFERENCE TO RELATED APPLICATION

This application is a continuation of and claims priority to U.S. patent application Ser. No. 15/597,822, filed May 17, 2017, now U.S. Pat. No. 10,415,017, issued Sep. 17, 2019, the entirety of which is hereby incorporated by reference.

TECHNICAL FIELD

The present disclosure relates generally to biotechnology. More specifically, the present disclosure relates to chimeric antigen receptors, nucleic acids encoding chimeric antigen receptors, macrophages harboring chimeric antigen receptors and/or nucleic acids encoding, and associated methods.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

BACKGROUND

Cancer consists of a group of diseases which involve unregulated cell growth and death, genome instability and mutations, tumor-promoting inflammation, induction of angiogenesis, immune system evasion, deregulation of metabolic pathways, immortal cell replication, and metastatic tissue invasion [1]. Cancer is the second leading cause of death in the United States after heart disease [2]. More than 1.6 million new cases of cancer are projected to be diagnosed each year, with more than 580,000 Americans expected to die (about 1600 cancer deaths per day), accounting for nearly 1 in 4 of all American deaths [2,3].

The immune system plays an important role in the development and progression of cancer. Immune cell infiltration to the tumor site can adversely affect malignancy progression and metastasis [4, 5]. Infiltration of macrophages into the tumor site has been shown to account for more than 50% of the tumor mass in certain breast cancer cases suggesting macrophages have a significant role in tumor progression [6-8].

Macrophages are cells derived from the myeloid lineage and belong to the innate immune system. They are derived from blood monocytes that migrate into tissue. One of their main functions is to phagocytose microbes and clear cellular debris. They also play an important role in both the initiation and resolution of inflammation [9, 10]. Moreover, macrophages can display different responses, ranging from pro-inflammatory to anti-inflammatory, depending on the type of stimuli they receive from the surrounding microenvironment [11]. Two major macrophage phenotypes have been proposed which correlate with extreme macrophage responses: M1 and M2.

M1 pro-inflammatory macrophages are activated upon contact with certain molecules such as lipopolysaccharide (LPS), IFN-γ, IL-1β, TNF-α, and Toll-like receptor engagement. M1 macrophages constitute a potent an of she immune system deployed to fight infections. They are capable of either direct (pathogen pattern recognition receptors) or indirect (Fc receptors, complement receptors) recognition of the pathogen. They are also armed in their ability to produce reactive oxygen species (ROS) as means to help killing, pathogens. In addition, M1 macrophages secrete pro-inflammatory cytokines and chemokines attracting other types of immune cells and integrating/orchestrating the immune response. M1, activation is induced by IFN-g, TNFa, GM-CSF, LPS and other toll-like receptors (TLR) ligands.

In contrast, M2 anti-inflammatory macrophages, also known as alternatively activated macrophages, are activated by anti-inflammatory molecules such as IL-4, IL-13, and IL-10 [12, 13]. M2 macrophages exhibit immunomodulatory, tissue repair, and angiogenesis properties which allow them to recruit regulatory T cells to sites of inflammation. M2 macrophages do not constitute a uniform population and often are further subdivided into M2a, M2b and M2c categories. The common denominator of all three subpopulations is high IL-10 production accompanied by low production of IL-12. One of their signatures is production of enzyme Arginase-1 that depletes L-arginine thereby suppressing T cell responses and depriving iNOS of its substrate.

The in vivo molecular mechanisms of macrophage polarization are poorly characterized because of the variety of signals macrophages experience in the cellular microenvironment [10, 14]. In recent years, progress has been made in identifying in vivo macrophage polarization under physiological conditions such as ontogenesis, pregnancy, and pathological conditions such as allergies, chronic inflammation, and cancer. We do know, however, that in vitro macrophage polarization is plastic and macrophages, with the help of cytokines, can be polarized back and forth to either phenotype [15, 16]. Interferon gamma (IFN-γ) and IL-4 are two cytokines that can polarize macrophages to M1 and M2 phenotypes, respectively [15].

The presence of macrophages is crucial for tumor progression and growth, and has implications in determining prognosis [17, 18]. Because macrophages can exhibit both pro-inflammatory and anti-inflammatory properties, it is important to understand their polarization and function in tumor progression and metastasis.

Macrophage Polarization

The tumor microenvironment can affect macrophage polarization. The process of polarization can be diverse and complex because of the hostile environment of IL-10, glucocorticoid hormones, apoptotic cells, and immune complexes that can interfere with innate immune cells function [11, 19]. The mechanisms of polarization are still unclear but we know they involve transcriptional regulation. For example, macrophages exposed to LPS or IFN-γ will polarize towards an M1 phenotype, whereas macrophages exposed to IL-4 or IL-13 will polarize towards an M2 phenotype. LPS or IFN-γ can interact with Toll-like receptor 4 (TLR4) on the surface of macrophages inducing the Trif and MyD88 pathways, inducing the activation of transcription factors IRF3, AP-1, and NFκB and thus activating TNFs genes, interferon genes, CXCL10, NOS2, IL-12, etc., which are necessary in a pro-inflammatory M1 macrophage response [20]. Similarly, IL-4 and IL-13 bind to IL-4R, activation the Jak/Stat6 pathway, which regulates the expression of CCL17, ARG1, IRF4, IL-10, SOCS3, etc., which are genes associated with an anti-inflammatory response (M2 response).

Additional mechanisms of macrophage polarization include microRNA (miRNA) micromanagement. miRNAs are small non-coding RNA of 22 nucleotides in length that regulate gene expression post-transcriptionally, as they affect the rate of mRNA degradation. Several miRNAs have been shown to be highly expressed in polarized macrophages, especially miRNA-155, miRNA-125, miRNA-378 (M1 polarization), and miRNA let-7c, miRNA-9, miRNA-21, miRNA-146, miRNA147, miRNA-187 (M2 polarization) [21].

Macrophage polarization is a complex process, were macrophages behave and elicit different responses depending on microenvironment stimuli. Therefore, macrophage polarization is better represented by a continuum of activation states where M1 and M2 phenotypes are the extremes of the spectrum. In recent years, there has been much controversy on the definition/description of macrophage activation and macrophage polarization. A recent paper published by Murray et al., in which they describe a set of standards to be considered for the consensus definition/description of macrophage activation, polarization, activators, and markers. This publication was much needed for the definition and characterization of activated/polarized macrophages [22].

M1 Phenotype

M1 pro-inflammatory macrophages or classically activated macrophages are aggressive, highly phagocytic, and produce large amounts of reactive oxygen and nitrogen species, thereby promoting a Th1 response [11]. M1 macrophages secrete high levels of two important inflammatory cytokines, IL-12 and IL-23. IL-12 induces the activation and clonal expansion of Th17 cells, which secrete high amounts of IL-17, which contributes to inflammation [23]. These characteristics allow M1 macrophages to control metastasis, suppress tumor growth, and control microbial infections [24]. Moreover, the infiltration and recruitment of M1 macrophages to tumor sites correlates with a better prognosis and higher overall survival rates in patients with solid tumors [17, 18, 25-28].

Polarization of macrophages to the M1 phenotype is regulated in vitro by inflammatory signals such as IFN-γ, TNF-α, IL-1β and LPS as well as transcription factors and miRNAs [29, 30]. Classically activated macrophages initiate the induction of the STAT1 transcription factor which targets CXCL9, CXCL10 (also known as IP-10), IFN regulatory factor-1, and suppressor of cytokine signaling-1 [31]. Cytokine signaling-1 protein functions downstream of cytokine receptors, and takes part in a negative feedback loop to attenuate cytokine signaling. In the tumor microenvironment, Notch signaling plays an important role in the polarization of M1 macrophages, as it allows transcription factor RBP-J to regulate classical activation. Macrophages that are deficient in Notch signaling express an M2 phenotype regardless of other extrinsic inducers [32]. One crucial miRNA, miRNA-155, is upregulated when macrophages are transitioning from M2 to M1; M1 macrophages overexpressing miRNA-155 are generally more aggressive and are associated with tumor reduction [33]. Moreover, miRNA-342-5p has been found to foster a greater inflammatory response in macrophages by targeting Akt1 in mice. This miRNA also promotes the upregulation of Nos2 and IL-6, both of which act as inflammatory signals for macrophages [34]. Other miRNAs such as miRNA-125 and miRNA-378 have also been shown to be involved in the classical activation pathway of macrophages (M1) [35].

Classically activated macrophages are thought to play an important role in the recognition and destruction of cancer cells as their presence usually indicates good prognosis. After recognition, malignant cells can be destroyed by M1 macrophages through several mechanisms, which include contact-dependent phagocytosis and cytotoxicity (i.e., cytokine release such as TNF-α) [24]. Environmental signals such as the tumor microenvironment or tissue-resident cells, however, can polarize M1 macrophages to M2 macrophages. In vivo studies of murine macrophages have shown that macrophages are plastic in their cytokine and surface marker expression and that re-polarizing macrophages to an M1 phenotype in the presence of cancer can help the immune system reject tumors [19].

M2 Phenotype

M2 macrophages are anti-inflammatory and aid in the process of angiogenesis and tissue repair. They express scavenger receptors and produce large quantities of IL-10 and other anti-inflammatory cytokines [33, 36]. Expression of IL-10 by M2 macrophages promotes a Th2 response. Th2 cells consequently upregulate the production of IL-3 and IL-4. IL-3 stimulates proliferation of all cells in the myeloid lineage (granulocytes, monocytes, and dendritic cells), in conjunction with other cytokines, e.g., Erythropoietin (EPO), Granulocyte macrophage colony-stimulating factor (GM-CSF), and IL-6. IL-4 is an important cytokine in the healing process because it contributes to the production of the extracellular matrix [23]. M2 macrophages exhibit functions that may help tumor progression by allowing blood vessels to feed the malignant cells and thus promoting their growth. The presence of macrophages (thought to be M2) in the majority of solid tumors negatively correlates with treatment success and longer survival rates [37]. Additionally, the presence of M2 macrophages has been linked to the metastatic potential in breast cancer. Lin and colleagues found that early recruitment of macrophages to the breast tumor sites in mice increase angiogenesis and incidence of malignancy [38]. It is thought that the tumor microenvironment helps macrophages maintain an M2 phenotype [23, 39]. Anti-inflammatory signals present in the tumor microenvironment such as adiponectin and IL-10 can enhance an M2 response [41].

Tumor-Associated Macrophages (TAMs)

Cells exposed to a tumor microenvironment behave differently. For example, tumor-associated macrophages found in the periphery of solid tumors are thought to help promote tumor growth and metastasis, and have an M2-like phenotype [42]. Tumor-associated macrophages can be either tissue resident macrophages or recruited macrophages derived from the bone marrow (macrophages that differentiate from monocytes to macrophages and migrate into tissue). A study by Cortez-Retamozo found that high numbers of TAM precursors in the spleen migrate to the tumor stroma, suggesting this organ as a TAM reservoir also [43]. TAM precursors found in the spleen were found to initiate migration through their CCR2 chemokine receptor [43]. Recent studies have found CSF-1 as the primary factor that attracts macrophages to the tumor periphery, and that CSF-1 production by cancer cells predicts lower survival rates and it indicates an overall poor prognosis [44-46]. Other cytokines such as TNF-α and IL-6 have been also linked to the accumulation/recruitment of macrophages to the tumor periphery [45].

It is thought that macrophages that are recruited around the tumor borders are regulated by an "angiogenic switch" that is activated in the tumor. The angiogenic switch is defined as the process by which the tumor develops a high density network of blood vessels that potentially allows the tumor to become metastatic, and is necessary for malignant transition. In a breast cancer mouse model, it was observed that the presence of macrophages was required for a full angiogenic switch. When macrophage maturation, migration, and accumulation around the tumor was delayed, the angiogenic switch was also delayed suggesting that the angiogenic switch does not occur in the absence of macrophages and that macrophage presence is necessary for malignancy progression [47]. Moreover, the tumor stromal cells produce chemokines such as CSF1, CCL2, CCL3, CCL5, and placental growth factor that will recruit macrophages to the tumor surroundings. These chemokines provide an environment for macrophages to activate the angiogenic switch, in which macrophages will produce high levels of IL-10, TGF-β, ARG-1 and low levels of IL-12, TNF-α, and IL-6. The level of expression of these cytokines suggests macrophages modulate immune evasion. It is important to note that macrophages are attracted to hypoxic tumor environments and will respond by producing hypoxia-inducible factor-1α (HIF-1α) and HIF-2α, which regulate the transcription of genes associated with angiogenesis. During the angiogenic switch, macrophages can also secrete VEGF (stimulated by the NF-κB pathway), which will promote blood vessel maturation and vascular permeability [48].

Tumor-associated macrophages are thought to be able to maintain their M2-like phenotype by receiving polarization signals from malignant cells such as IL-1R and MyD88, which are mediated through IkB kinase β and NF-kB signaling cascade. Inhibition of NF-kB in TAMs promotes classical activation [40]. Moreover, another study suggested that p50 NF-kB subunit was involved in suppression of M1 macrophages, and reduction of inflammation promoted tumor growth. A p50 NF-κB knock-out mouse generated by Saccani et al. suggested that M1 aggressiveness was restored upon p50 NF-kB knockout, reducing tumor survival [49].

Because the tumor mass contains a great number of M2-like macrophages, TAMs can be used as a target for cancer treatment. Reducing the number of TAMs or polarizing them towards an M1 phenotype can help destroy cancer cells and impair tumor growth [50-52]. Luo and colleagues used a vaccine against legumain, a cysteine protease and stress protein upregulated in TAMs thought to be a potential tumor target [52]. When the vaccine against legumain was administered to mice, genes controlling angiogenesis were downregulated and tumor growth was halted [52].

Metabolism and Activation Pathways

Metabolic alterations present in tumor cells are controlled by the same genetic mutations that produce cancer [53]. As a result of these metabolic alterations, cancer cells are able to produce signals that can modify the polarization of macrophages and promote tumor growth [54, 55].

M1 and M2 macrophages demonstrate distinct metabolic patterns that reflect their dissimilar behaviors [56]. The M1 phenotype increases glycolysis and skews glucose metabolism towards the oxidative pentose phosphate pathway, thereby decreasing oxygen consumption and consequently producing large amounts of radical oxygen and nitrogen species as well as inflammatory cytokines such as TNF-α, IL-12, and IL-6 [56, 57]. The M2 phenotype increases fatty acid intake and oxidation, which decreases flux towards the pentose phosphate pathway while increasing the overall cell redox potential, consequently upregulating scavenger receptors and immunomodulatory cytokines such as IL-10 and TGF-β [56].

Multiple metabolic pathways play important roles in macrophage polarization. Protein kinases, such as Akt1 and Akt2, alter macrophage polarization by allowing cancer cells to survive, proliferate, and use an intermediary metabolism [58]. Other protein kinases can direct macrophage polarization through glucose metabolism by increasing glycolysis and decreasing oxygen consumption [57, 59]. Shu and colleagues were the first to visualize macrophage metabolism and immune response in vivo using a PET scan and a glucose analog [60].

L-arginine metabolism also exhibits discrete shifts important to cytokine expression in macrophages and exemplifies distinct metabolic pathways which alter TAM-tumor cell interactions [61]. Classically activated (M1) macrophages favor inducible nitric oxide synthase (iNOS). The iNOS pathway produces cytotoxic nitric oxide (NO), and consequently exhibits anti-tumor behavior. Alternatively activated (M2) macrophages have been shown to favor the arginase pathway and produce ureum and 1-ornithine, which contribute to progressive tumor cell growth [61, 62].

Direct manipulation of metabolic pathways can alter macrophage polarization. The carbohydrate kinase-like protein (CARKL) protein, which plays a role in glucose metabolism, has been used to alter macrophage cytokine signatures [56, 57]. When CARKL is knocked down by RNAi, macrophages tend to adopt an M1-like metabolic pathway (metabolism skewed towards glycolysis and decreased oxygen consumption). When CARKL is overexpressed, macrophages adopt an M2-like metabolism (decreased glycolytic flux and more oxygen consumption) [56]. When macrophages adopt an M1-like metabolic state through LPS/TLR4 engagement, CARKL levels decrease, genes controlled by the NFκB pathway are activated (TNF-α, IL-12, and IL-6), and cell redox potential increases due to growing concentrations of NADH:NAD+ and GSH:GSSSG complexes. During an M2-like metabolic state, macrophages upregulate CARKL and genes regulated by STATE/IL-4 (IL-10 and TGF-β).

Obesity can also affect macrophage polarization. Obesity is associated with a state of chronic inflammation, an environment that drives the IL4/STAT6 pathway to activate NKT cells, which drive macrophages towards an M2 response. During late-stage diet-induced obesity, macrophages migrate to adipose tissue, where immune cells alter levels of $T_H1$ or $T_H2$ cytokine expression in the adipose tissue, causing an M2 phenotype bias and possibly increased insulin sensitivity [63].

M1 phenotype bias by targeting metabolic pathways in TAMS may offer an alternative means of reducing tumor growth and metastasis.

Macrophage Immunotherapy Approaches Against Cancer

The role of cancer immunotherapy is to stimulate the immune system to recognize, reject, and destroy cancer cells. Cancer immunotherapy with monocytes/macrophages has the goal to polarize macrophages towards a pro-inflammatory response (M1), thus allowing the macrophages and other immune cells to destroy the tumor. Many cytokines and bacterial compounds can achieve this in vitro, although the side effects are typically too severe in vivo. The key is to find a compound with minimal or easily managed patient side effects. Immunotherapy using monocytes/macrophages has been used in past decades and new approaches are being developed every year [64, 65]. Early immunotherapy has established a good foundation for better cancer therapies and increased survival rate in patients treated with immunotherapies [66].

Some approaches to cancer immunotherapy include the use of cytokines or chemokines to recruit activated macrophages and other immune cells to the tumor site which allow for recognition and targeted destruction of the tumor site [67, 68]. IFN-α and IFN-β have been shown to inhibit tumor progression by inducing cell differentiation and apoptosis

[69]. Also, IFN treatments are anti-proliferative and can increase S phase time in the cell cycle [70, 71]. Zhang and colleagues performed a study in nude mice using IFN-β gene therapy to target human prostate cancer cells. Their results indicate that adenoviral-delivered IFN-β gene therapy involves macrophages and helps suppress growth and metastasis [72].

The macrophage inhibitory factor (MIF) is another cytokine that can be used in cancer immunotherapy. MIF is usually found in solid tumors and indicates poor prognosis. MIF inhibits aggressive macrophage function and drives macrophages toward an M2 phenotype, which can aid tumor growth and progression. Simpson, Templeton & Cross (2012) found that MIF induces differentiation of myeloid cells, macrophage precursors, into a suppressive population of myeloid cells that express an M2 phenotype [73]. By targeting MIF, they were able to deplete this suppressive population of macrophages, inhibiting their growth and thus control tumor growth and metastasis [73].

The chemokine receptor type 2, CCR2, is crucial to the recruitment of monocytes to inflammatory sites and it has been shown as a target to prevent the recruitment of macrophages to the tumor site, angiogenesis, and metastasis. Sanford and colleagues (2013) studied a novel CCR2 inhibitor (PF-04136309) in a pancreatic mouse model, demonstrating that the CCR2 inhibitor depleted monocyte/macrophage recruitment to the tumor site, decreased tumor growth and metastasis, and increased antitumor immunity [74]. Another recent study by Schmall et al. showed that macrophages co-cultured with 10 different human lung cancers upregulated CCR2 expression. Moreover, they showed that tumor growth and metastasis were reduced in a lung mouse model treated with a CCR2 antagonist [75].

Other studies have used liposomes to deliver drugs to deplete M2 macrophages from tumors and to stop angiogenesis. Cancer cells that express high levels of IL-10 grow faster and induce more angiogenesis in vivo. Kimura and colleagues found that macrophages exposed to tumor cells expressing IL-1β produced higher levels of angiogenic factors and chemokines such as vascular endothelial growth factor A (VEG-A), IL-8, monocyte chemoattractant protein 1, etc., facilitating tumor growth and angiogenesis [76]. When they used clodronate liposomes to deplete macrophages, they found fewer IL-1β-producing tumor cells. They also found that by inhibiting NF-κB and AP-1 transcription factors in the cancer cells, tumor growth and angiogenesis were reduced. These findings may suggest that macrophages that surround the tumor site may be involved in promoting tumor growth and angiogenesis [76].

Compounds such as methionine enkephalin (MENK) have anti-tumor properties in vivo and in vitro. MENK has the ability to polarize M2 macrophages to M1 macrophages by downregulating CD206 and arginase-1 (M2 markers) while upregulating CD64, MHC-II, and the production of nitric oxide (M1 markers). MENK can also upregulate TNF-α and downregulate IL-10 [77].

Recent studies have focused on bisphosphonates as a potential inhibitor of M2 macrophages. Bisphosphonates are commonly used to treat metastatic breast cancer patients to prevent skeletal complications such as bone resorption [78]. While bisphosphonates stay in the body for short periods of time, bisphosphonates can target osteoclasts, cells in the same family as macrophages, due to their high affinity for hydroxyapatite. Once bisphosphonates bind to the bones, the bone matrix internalizes the bisphosphonates by endocytosis. Once in the cytoplasm, bisphosphonates can inhibit protein prenylation, an event that prevents integrin signaling and endosomal trafficking, thereby forcing the cell to go apoptotic [69]. Until recently, it was unknown whether bisphosphonates could target tumor-associated macrophages but a recent study by Junankar et al. has shown that macrophages uptake nitrogen-containing bisphosphonate compounds by pinocytosis and phagocytosis, an event that does not occur in epithelial cells surrounding the tumor [79]. Forcing TAMs to go apoptotic using bisphosphonates could reduce angiogenesis and metastasis.

Additional approaches to cancer immunotherapy include the use of biomaterials that may elicit an immune response. Cationic polymers are used in immunotherapy because of their reactivity once dissolved in water. Chen et al. used cationic polymers including PEI, polylysine, cationic dextran and cationic gelatin to produce a strong Th1 immune response [77]. They were also able to induce proliferation of CD4+ cells and secretion of IL-12 typical of M1 macrophages [77]. Huang and colleagues also used biomaterials to trigger TAMs to produce an anti-tumor response by targeting TLR4 [80]. This study found that TAMs were able to polarize to an M1 phenotype and express IL-12. They found that these cationic molecules have direct tumoricidal activity and demonstrate tumor reduction in mice [80].

TLR4

Toll-like receptor 4 is a protein in humans that is encoded by the TLR4 gene. TLR 4 detects lipopolysaccharide (LPS) on gram negative bacteria and thus plays a fundamental role in the recognition of danger and the activation of the innate immune system (FIG. 7). It cooperates with LY96 (MD-2) and CD14 to mediate signal transduction when macrophages are induced by LPS. The cytoplasmic domain of TLR4 is responsible for the activation of M1 macrophages when they detect the presence of LPS. This is the functional portion of the receptor that would be coupled to the MOTO-CAR (i.e., chimeric receptor) to induce activation of the monocyte/macrophage when the CAR binds its target protein.

The adaptor proteins MyD88 and TIRAP contribute to the activation of several and possibly all pathways via direct interactions with TLR4's Toll/interleukin-1 receptor (IL-1R) (TIR) domain. However, additional adaptors that are required for the activation of specific subsets of pathways may exist, which could contribute to the differential regulation of target genes.

Thymidine Kinase

Human Thymidine Kinase 1 (TK1) is a well-known nucleotide salvage pathway enzyme that has largely been studied in the context of its overexpression in tumors. Since TK1 was initially popularized by its expression in the serum of cancer patients (sTK), its diagnostic and prognostic potential has been studied extensively. For example, several studies have demonstrated that sTK1 in many different cancer patients is elevated in a stage-like manner with a higher level of TK1 indicating a more advanced tumor [81].

Other studies have investigated the prognostic potential of TK1. One such study demonstrates that the TK1 levels in primary breast tumors can be used to predict recurrence. Other exciting TK1 prognostic studies show significant reductions in sTK1 levels when patients respond to treatment while sTK1 levels continue to rise in patients who do not appear to respond to their treatment. It is also known that sTK1 levels begin to rise prior to recurrence and noted in some cases sTK1 levels could predict recurrence "1-6 months before the onset of clinical symptoms." Several other studies confirm the rich potential of TK1 as a diagnostic and prognostic indicator of cancer [82].

Although the diagnostic and prognostic potential of TK1 has been well established, the therapeutic potential of TK1 remains veiled in comparison. While it is true that HSV-TK has been used in gene therapy and PET imaging utilizes TK1 to identify proliferating cancer cells, few, if any studies address the possibility of a TK1 immunotherapy. Perhaps this is primarily because TK1 is a known cytosolic protein. It has been recently discovered that TK1 is expressed not only in cancer cells but also on the surface membrane of multiple tumor types and is therefore a very viable target for tumor immunotherapy.

BRIEF SUMMARY

Described herein are chimeric receptors. Chimeric receptors comprise a cytoplasmic domain; a transmembrane domain; and an extracellular domain. In embodiments, the cytoplasmic domain comprises a cytoplasmic portion of a receptor that when activated polarizes a macrophage. In further embodiments, a wild-type protein comprising the cytoplasmic portion does not comprise the extracellular domain of the chimeric receptor (see, e.g., FIG. 21). In embodiments, the binding of a ligand to the extracellular domain of the chimeric receptor activates the intracellular portion of the chimeric receptor (see, e.g., FIG. 22). Activation of the intracellular portion of the chimeric receptor may polarize the macrophage into an M1 or M2 macrophage (see, e.g., FIGS. 23 and 24(A) and 25).

In certain embodiments, the extracellular domain may comprise an antibody or a fragment there of that specifically binds to a ligand. In embodiments, the chimeric receptor may contain a linker. In embodiments, the chimeric receptor may contain a hinge region.

Further embodiments include cells comprising a chimeric receptor or nucleic acids encoding a chimeric receptor.

Embodiments include methods of polarizing a macrophage by contacting a macrophage comprising a chimeric receptor with a ligand for the extracellular domain of the chimeric receptor; binding the ligand to the extracellular domain of the chimeric receptor. The binding of the ligand to the extracellular domain of the chimeric receptor activates the cytoplasmic portion and the activation of the cytoplasmic portion polarizes the macrophage.

These and other aspects of the disclosure will become apparent to the skilled artisan in view of the teachings contained herein.

BRIEF DESCRIPTION OF THE SEVERAL VIEWS OF THE DRAWINGS

FIG. 1A depicts a block diagram of the order of elements in the chimeric receptor TK1-MOTO1. FIG. 1B depicts the sequence of TK1-MOTO1 (SEQ ID NO:35). Amino acids 1-18 are a signal peptide (SP), amino acids 19-275 are an anti-TK1 ScFv, amino acids 276-290 are a GS linker, amino acids 291-313 are a TLR4 transmembrane domain, and amino acids 314-496 are a TLR4 cytosolic domain.

FIG. 2A depicts a block diagram of the order of elements in the chimeric receptor TK1-MOTO2. FIG. 2B depicts the sequence of TK1-MOTO2 (SEQ ID NO:36). Amino acids 1-18 are a signal peptide (SP), amino acids 19-275 are an anti-TK1 ScFv, amino acids 276-290 are a GS linker, amino acids 291-295 are a LRR short hinge, amino acids 296-318 are a TLR4 transmembrane domain, and amino acids 319-500 are a TLR4 cytosolic domain.

FIG. 3A depicts a block diagram of the order of elements in the chimeric receptor TK1-MOTO3. FIG. 3B depicts the sequence of TK1-MOTO3 (SEQ ID NO:37). Amino acids 1-18 are a signal peptide (SP), amino acids 19-275 are an anti-TK1 ScFv, amino acids 276-290 are a GS linker, amino acids 291-345 are a LRR long hinge, amino acids 346-368 are a TLR4 transmembrane domain, and amino acids 269-501 are a TLR4 cytosolic domain.

FIG. 4A depicts a block diagram of the order of elements in the chimeric receptor TK1-MOTO4. FIG. 4B depicts the sequence of TK1-MOTO4 (SEQ ID NO:38). Amino acids 1-18 are a signal peptide (SP), amino acids 19-275 are an anti-TK1 ScFv, amino acids 276-290 are a GS linker, amino acids 291-302 are an IgG4 short hinge, amino acids 303-325 are a TLR4 transmembrane domain, and amino acids 326-508 are a TLR4 cytosolic domain.

FIG. 5A depicts a block diagram of the order of elements in the chimeric receptor TK1-MOTO5. FIG. 5B depicts the sequence of TK1-MOTO5 (SEQ ID NO:39). Amino acids 1-18 are a signal peptide (SP), amino acids 19-275 are an anti-TK1 ScFv, amino acids 276-290 are a GS linker, amino acids 291-409 are an IgG 119 amino acid medium hinge, amino acids 410-432 are a TLR4 transmembrane domain, and amino acids 433-615 are a TLR4 cytosolic domain.

FIG. 6A depicts a block diagram of the order of elements in the chimeric receptor TK1-MOTO6. FIG. 6B depicts the sequence of TK1-MOTO6 (SEQ ID NO:40). Amino acids 1-18 are a signal peptide (SP), amino acids 19-275 are an anti-TK1 ScFv, amino acids 276-290 are a GS linker, amino acids 291-518 are an IgG4 long hinge, amino acids 519-541 are a TLR4 transmembrane domain, and amino acids 542-724 are a TLR4 cytosolic domain.

FIG. 7A depicts a block diagram of the order of elements in the chimeric receptor TK1-MOTO7. FIG. 7B depicts the sequence of TK1-MOTO7 (SEQ ID NO:41). Amino acids 1-18 are a signal peptide (SP), amino acids 19-275 are an anti-TK1 ScFv, amino acids 276-290 are a GS linker, amino acids 291-358 are mutated CD8 hinge with C339S and C356S, amino acids 359-381 are a TLR4 transmembrane domain, and amino acids 382-564 are a TLR4 cytosolic domain.

FIG. 8A depicts a block diagram of the order of elements in the chimeric receptor TK1-MOTOR. FIG. 8B depicts the sequence of TK1-MOTO8 (SEQ ID NO:42). Amino acids 1-18 are a signal peptide (SP), amino acids 19-275 are an anti-TK1 ScFv, amino acids 276-290 are a GS linker, amino acids 291-358 are a portion of a CD8 hinge, amino acids 359-381 are a TLR4 transmembrane domain, and amino acids 382-564 are a TLR4 cytosolic domain.

FIG. 9A depicts a block diagram of the order of elements in the chimeric receptor TK1-MO-FCGRA-CAR-1. FIG. 9B depicts the sequence of TK1-MO-FCGRA-CAR-1 (SEQ ID NO:43). Amino acids 1-18 are a signal peptide (SP), amino acids 19-275 are an anti-TK1 ScFv, amino acids 276-290 are a GS linker, amino acids 291-311 are a FCGR3A transmembrane domain, amino acids 312-336 are a FCGR3A cytosolic domain, and amino acids 337-378 are a FCER1G cytosolic domain.

FIG. 10A depicts a block diagram of the order of elements in the chimeric receptor TK1-MO-FCGRA-CAR-2. FIG. 10B depicts the sequence of TK1-MO-FCGRA-CAR-2 (SEQ ID NO:44). Amino acids 1-18 are a signal peptide (SP), amino acids 19-275 are an anti-TK1 ScFv, amino acids 276-290 are a GS linker, amino acids 291-358 are mutated CD8 hinge with C339S and C356S, amino acids 359-379 are a FCGR3A transmembrane domain, amino acids 380-404 are a FCGR3A cytosolic domain, and amino acids 405-446 are a FCER1G cytosolic domain.

FIG. 11A depicts a block diagram of the order of elements in the chimeric receptor TK1-MO-FCGRA-CAR-3. FIG. 11B depicts the sequence of TK1-MO-FCGRA-CAR-3

Figure 21:
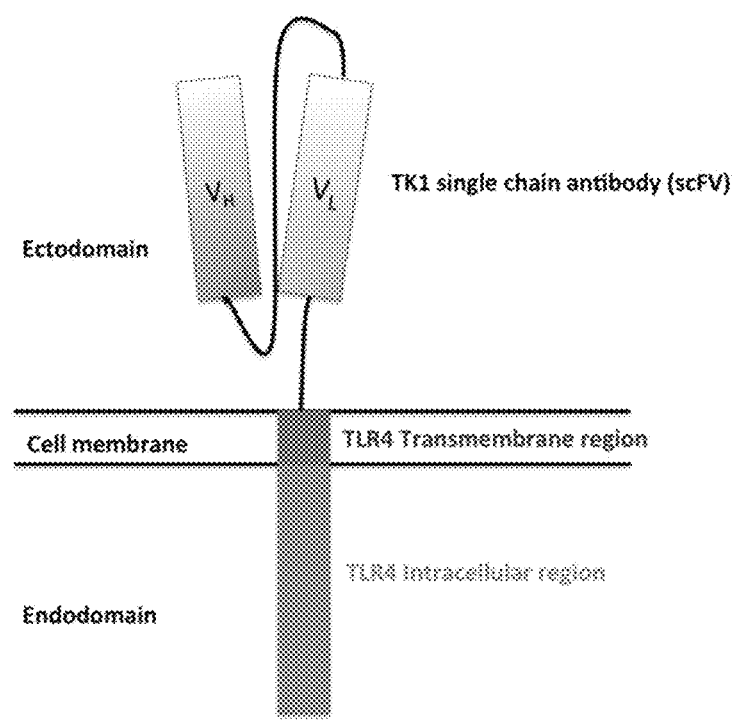

(SEQ ID NO:45). Amino acids 1-18 are a signal peptide (SP), amino acids 19-275 are an anti-TK1 ScFv, amino acids 276-290 are a GS linker, amino acids 291-358 are a portion of a CD8 hinge, amino acids 359-379 are a FCGR3A transmembrane domain, amino acids 380-404 are a FCGR3A cytosolic domain, and amino acids 405-446 are a FCER1G cytosolic domain.

FIG. 12A depicts a block diagram of the order of elements in the chimeric receptor TK1-MO-FCGRA-CAR-4. FIG. 12B depicts the sequence of TK1-MO-FCGRA-CAR-4 (SEQ ID NO:46). Amino acids 1-18 are a signal peptide (SP), amino acids 19-275 are an anti-TK1 ScFv, amino acids 276-290 are a GS linker, amino acids 291-303 are a IgG4 short hinge, amino acids 304-324 are a FCGR3A transmembrane domain, amino acids 325-349 are a FCGR3A cytosolic domain, and amino acids 350-391 are a FCER1G cytosolic domain.

FIG. 13A depicts a block diagram of the order of elements in the chimeric receptor TK1-MO-FCGRA-CAR-5. FIG. 13B depicts the sequence of TK1-MO-FCGRA-CAR-5 (SEQ ID NO:47). Amino acids 1-18 are a signal peptide (SP), amino acids 19-275 are an anti-TK1 ScFv, amino acids 276-290 are a GS linker, amino acids 291-409 are a IgG4 119 amino acid hinge, amino acids 410-430 are a FCGR3A transmembrane domain, amino acids 431-455 are a FCGR3A cytosolic domain, and amino acids 456-497 are a FCER1G cytosolic domain.

FIG. 14A depicts a block diagram of the order of elements in the chimeric receptor TK1-MO-FCGRA-CAR-6. FIG. 14B depicts the sequence of TK1-MO-FCGRA-CAR-6 (SEQ ID NO:48). Amino acids 1-18 are a signal peptide (SP), amino acids 19-275 are an anti-TK1 ScFv, amino acids 276-290 are a GS linker, amino acids 291-519 are a IgG4 long hinge, amino acids 520-540 are a FCGR3A transmembrane domain, amino acids 541-565 are a FCGR3A cytosolic domain, and amino acids 566-607 are a FCER1G cytosolic domain.

FIG. 15A depicts a block diagram of the order of elements in the chimeric receptor TK1-MO-FCG2A-CAR-1. FIG. 15B depicts the sequence of TK1-MO-FCG2A-CAR-1 (SEQ ID NO:49). Amino acids 1-18 are a signal peptide (SP), amino acids 19-275 are an anti-TK1 ScFv, amino acids 276-290 are a GS linker, amino acids 291-312 are a FCGR2A transmembrane domain, amino acids 313-390 are a FCGR2A cytosolic domain.

FIG. 16A depicts a block diagram of the order of elements in the chimeric receptor TK1-MO-FCG2A-CAR-2. FIG. 16B depicts the sequence of TK1-MO-FCG2A-CAR-2 (SEQ ID NO:50). Amino acids 1-18 are a signal peptide (SP), amino acids 19-275 are an anti-TK1 ScFv, amino acids 276-290 are a GS linker, amino acids 291-358 are mutated CD8 hinge with C339S and C356S, amino acids 359-380 are a FCGR2A transmembrane domain, amino acids 381-458 are a FCGR2A cytosolic domain.

FIG. 17A depicts a block diagram of the order of elements in the chimeric receptor TK1-MO-FCG2A-CAR-3. FIG. 17B depicts the sequence of TK1-MO-FCG2A-CAR-3 (SEQ ID NO:51). Amino acids 1-18 are a signal peptide (SP), amino acids 19-275 are an anti-TK1 ScFv, amino acids 276-290 are a GS linker, amino acids 291-358 are a portion of a CD8 hinge, amino acids 359-380 are a FCGR2A transmembrane domain, amino acids 381-458 are a FCGR2A cytosolic domain.

FIG. 18A depicts a block diagram of the order of elements in the chimeric receptor TK1-MO-FCG2A-CAR-4. FIG. 18B depicts the sequence of TK1-MO-FCG2A-CAR-4 (SEQ ID NO:52). Amino acids 1-18 are a signal peptide (SP), amino acids 19-275 are an anti-TK1 ScFv, amino acids 276-290 are a GS linker, amino acids 291-303 are a IgG4 short hinge, amino acids 304-325 are a FCGR2A transmembrane domain, amino acids 326-403 are a FCGR2A cytosolic domain.

FIG. 19A depicts a block diagram of the order of elements in the chimeric receptor TK1-MO-FCG2A-CAR-5. FIG. 19B depicts the sequence of TK1-MO-FCG2A-CAR-5 (SEQ ID NO:53). Amino acids 1-18 are a signal peptide (SP), amino acids 19-275 are an anti-TK1 ScFv, amino acids 276-290 are a GS linker, amino acids 291-409 are a IgG4 119 amino acid hinge, amino acids 410-431 are a FCGR2A transmembrane domain, amino acids 432-509 are a FCGR2A cytosolic domain.

FIG. 20A depicts a block diagram of the order of elements in the chimeric receptor TK1-MO-FCG2A-CAR-6. FIG. 20B depicts the sequence of TK1-MO-FCG2A-CAR-6 (SEQ ID NO:54). Amino acids 1-18 are a signal peptide (SP), amino acids 19-275 are an anti-TK1 ScFv, amino acids 276-290 are a GS linker, amino acids 291-519 are a IgG4 long hinge, amino acids 520-541 are a FCGR2A transmembrane domain, amino acids 542-619 are a FCGR2A cytosolic domain.

FIG. 21 is a schematic illustrating a chimeric receptor.

Figure 22:
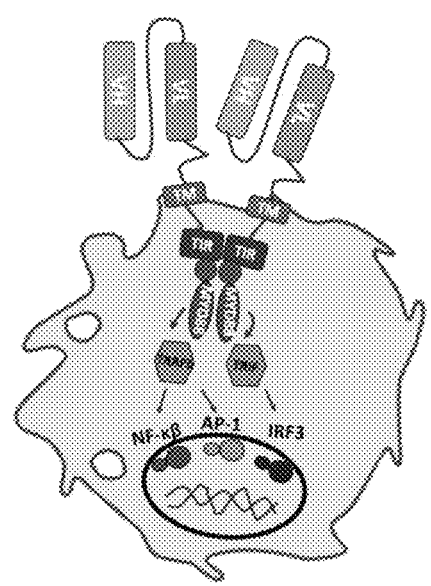

FIG. 22 is a schematic showing a macrophage expressing a chimeric receptor. As depicted, the chimeric receptor comprises the cytosolic domain of a toll like receptors, a transmembrane domain, and a ScFv specific for a ligand. The arrows depict signaling to polarize the macrophage upon the ScFv binding the ligand.

Figure 23:
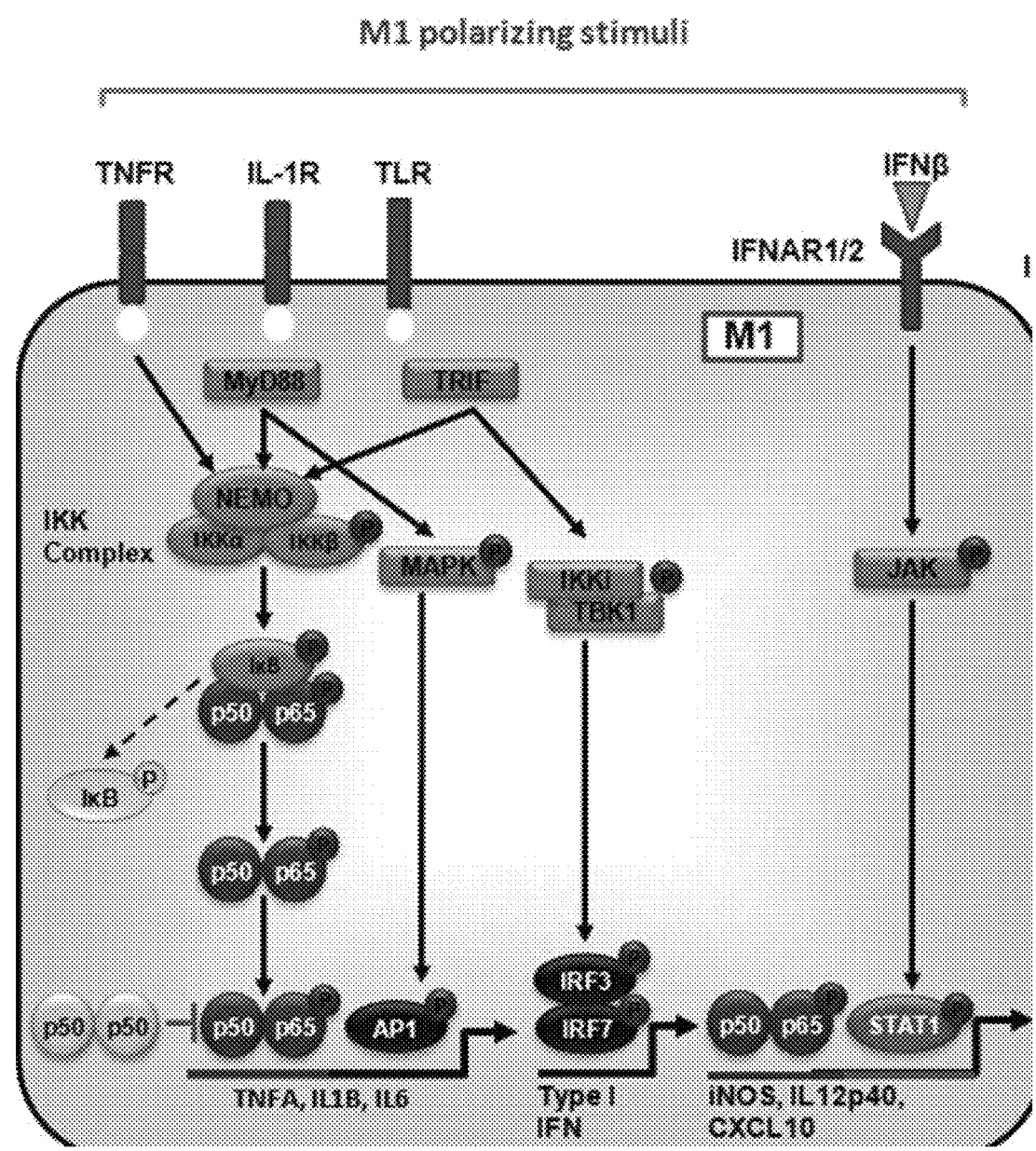

FIG. 23 is a schematic showing different macrophage receptors that could be utilized to build a chimeric receptor.

Figure 24A:
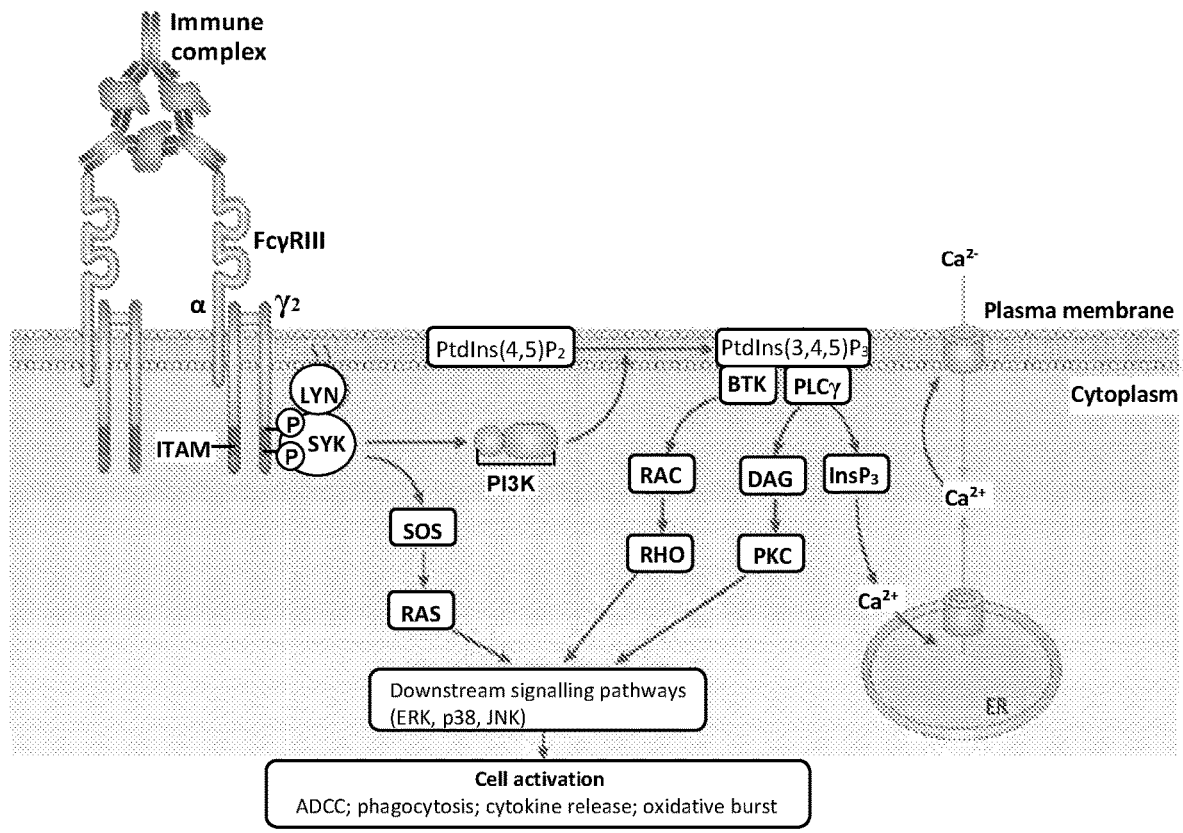
Figure 24B:
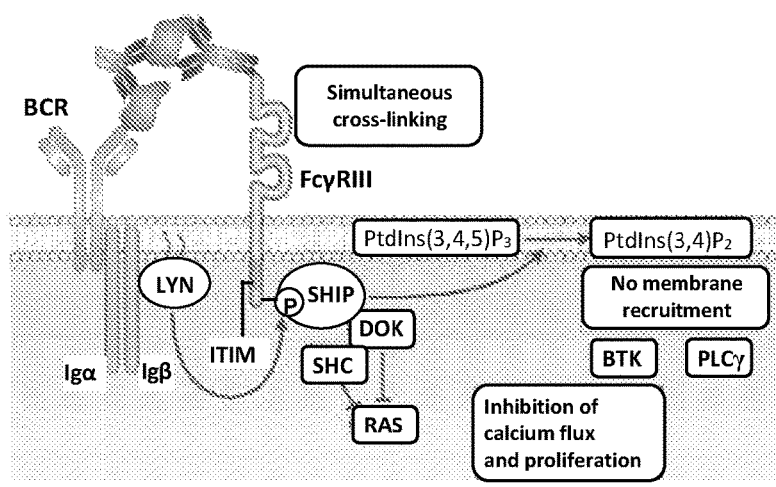
Figure 24C:
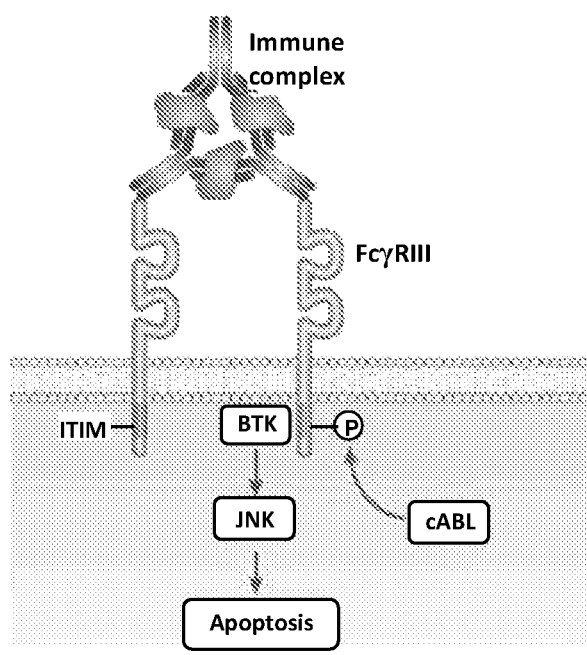

FIGS. 24A through 24C. FIG. 24A is a schematic showing the Fc Gamma Receptor III signaling cascade leading to cell activation. FIG. 24B is a schematic showing the Fc Gamma Receptor III signaling cascade leading to inhibition of calcium flux and proliferation. FIG. 24C is a schematic showing the Fc Gamma Receptor III signaling cascade leading to apoptosis.

Figure 25:
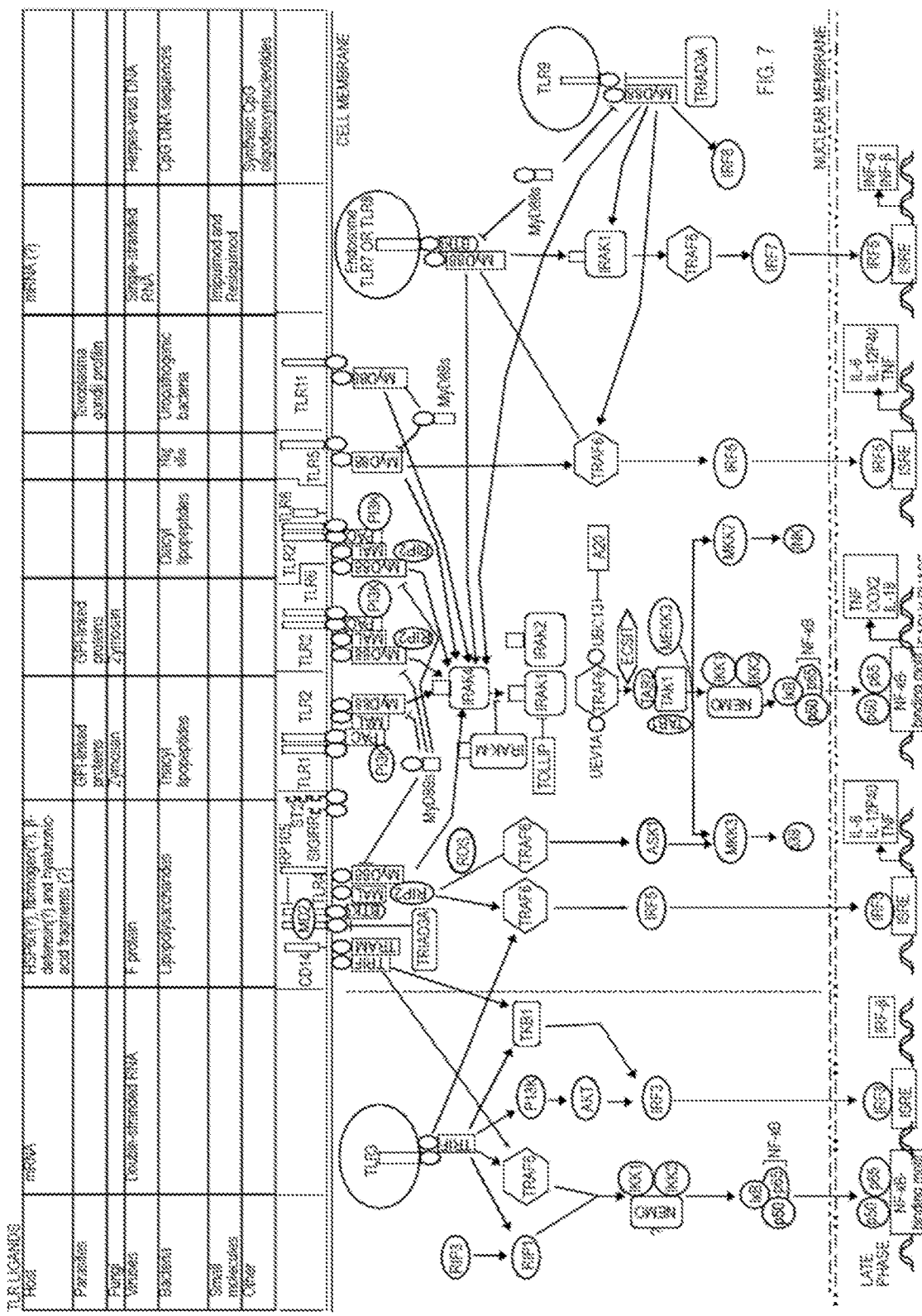

FIG. 25 is a schematic illustrating the Toll Like Receptor Signaling cascade.

Figure 26:
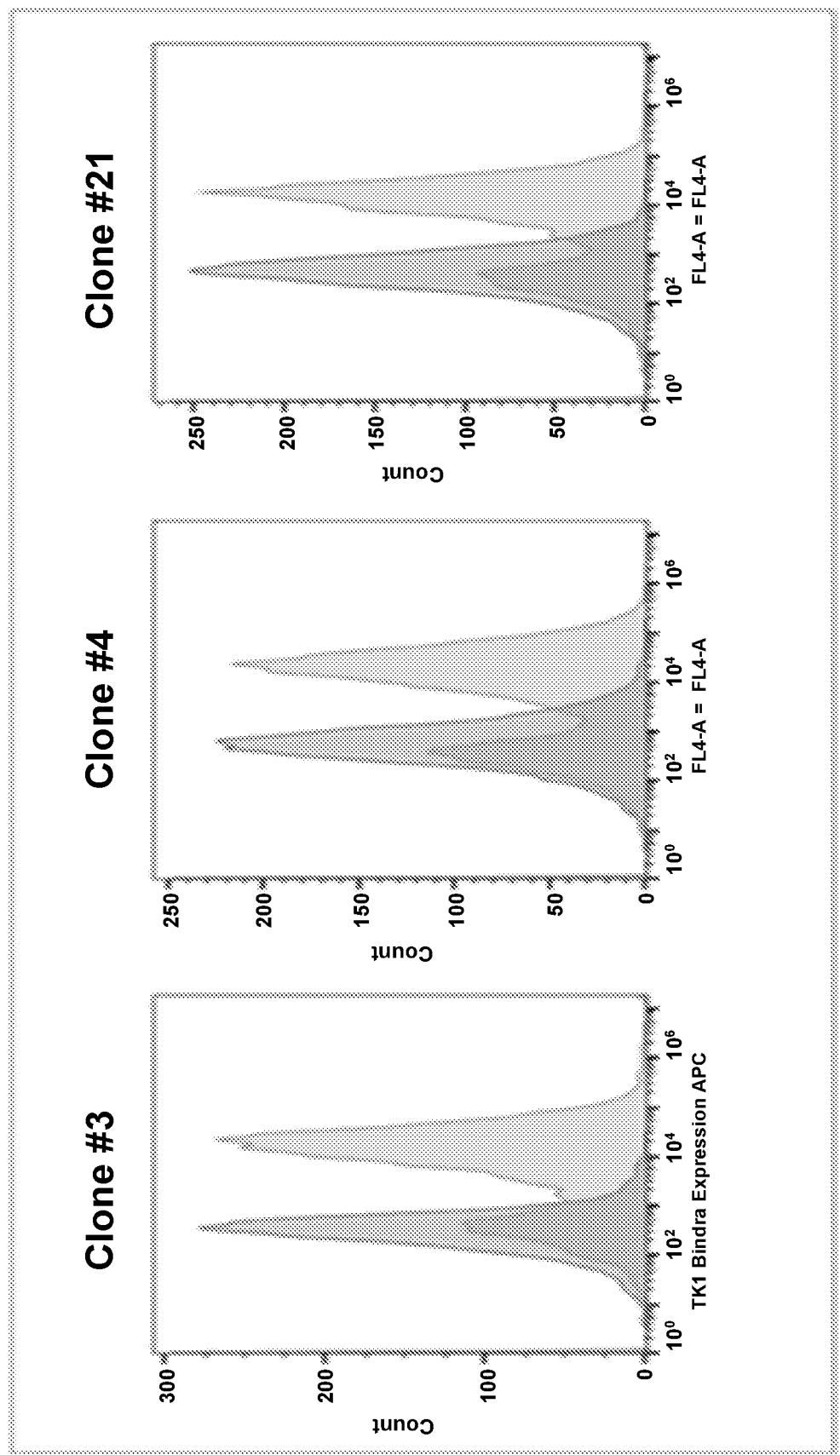

FIG. 26 presents graphs illustrating flow cytometry confirming that an expressed antibody fragment binds the ligand of interest.

Figure 27:
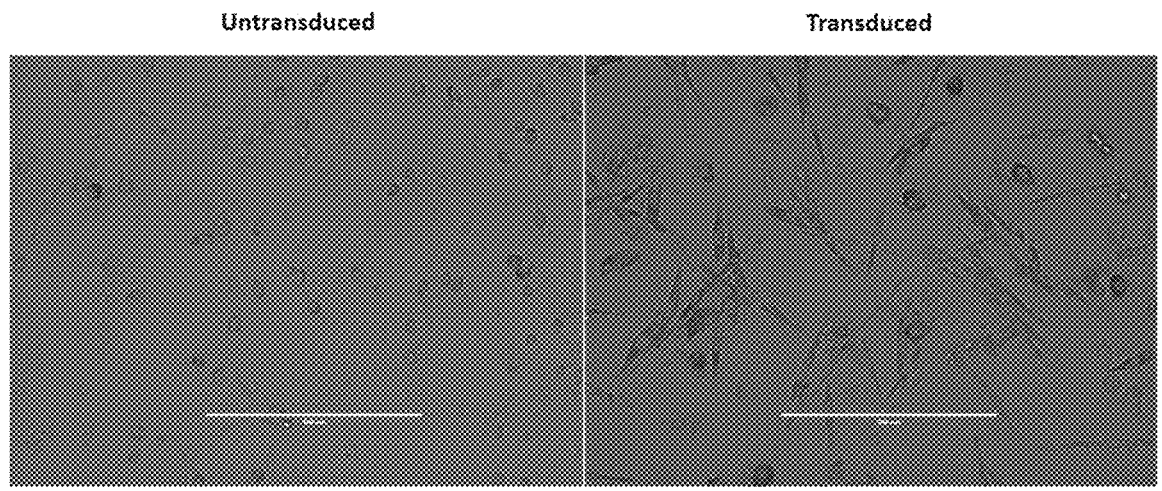

FIG. 27 presents two images showing a phenotype change in macrophages after transduction with a chimeric receptor.

Figure 28:
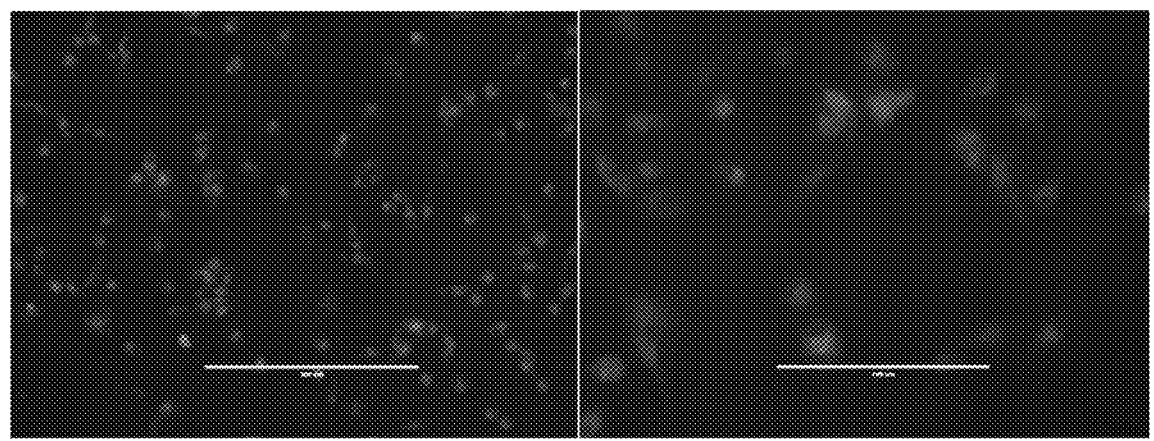

FIG. 28 presents two images confirming the expression of a chimeric receptor in monocytes.

Figure 29:
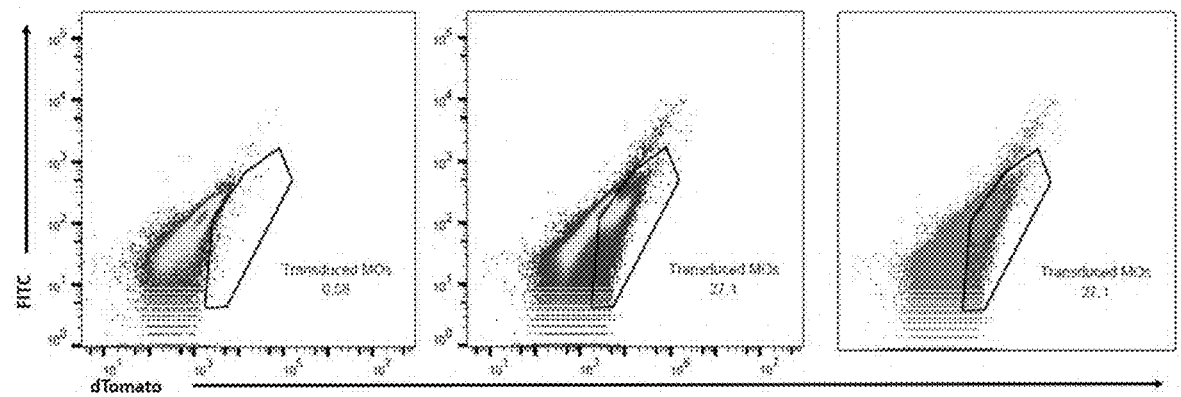

FIG. 29 presents three scatter plots of fluorescence activated cell sorting demonstrating the expression of dTomato. The left most plot shows a control wherein only 0.58% of cells show fluorescence which would indicate expression of dTomato. The right two plots show a transduction efficiency of 27.1 percent after transduction.

Figure 30:
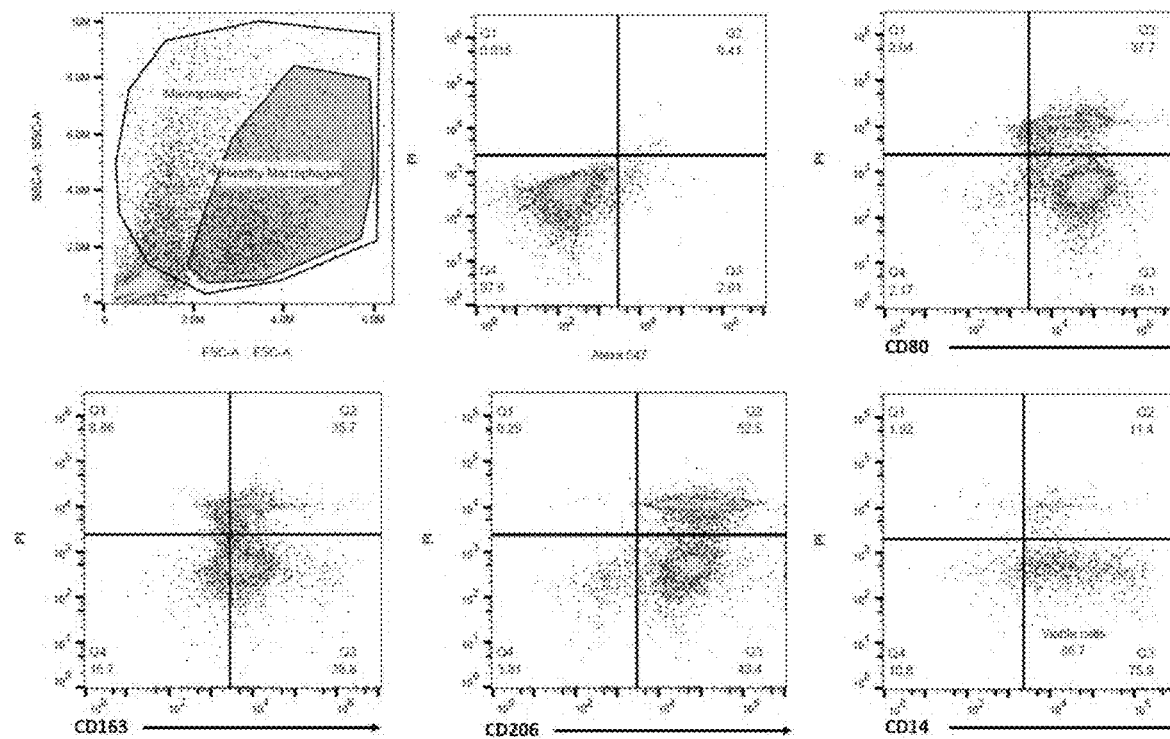

FIG. 30 presents six scatter plots of fluorescence activated cell sorting demonstrating the retention of dye (Alexa 647), and the expression of CD80, CD163, CD206, and CD14 in macrophages transduced with a chimeric receptor.

Figure 31:
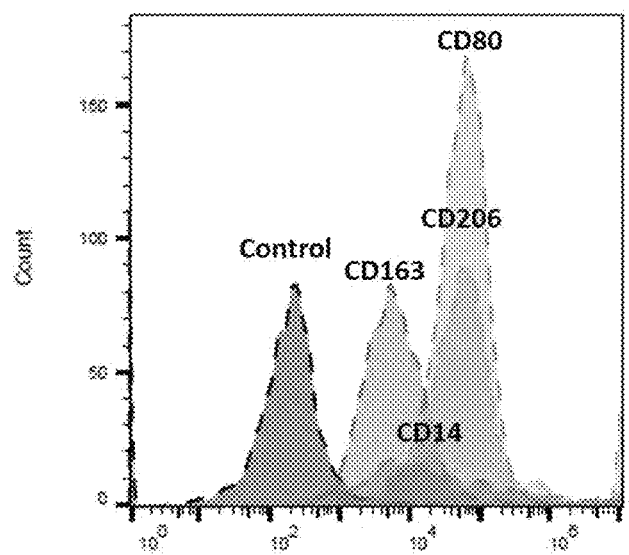

FIG. 31 presents a histogram demonstrating the relative expression levels of CD80, CD163, CD206, and CD14 in macrophages transduced with a chimeric receptor.

Figure 32:
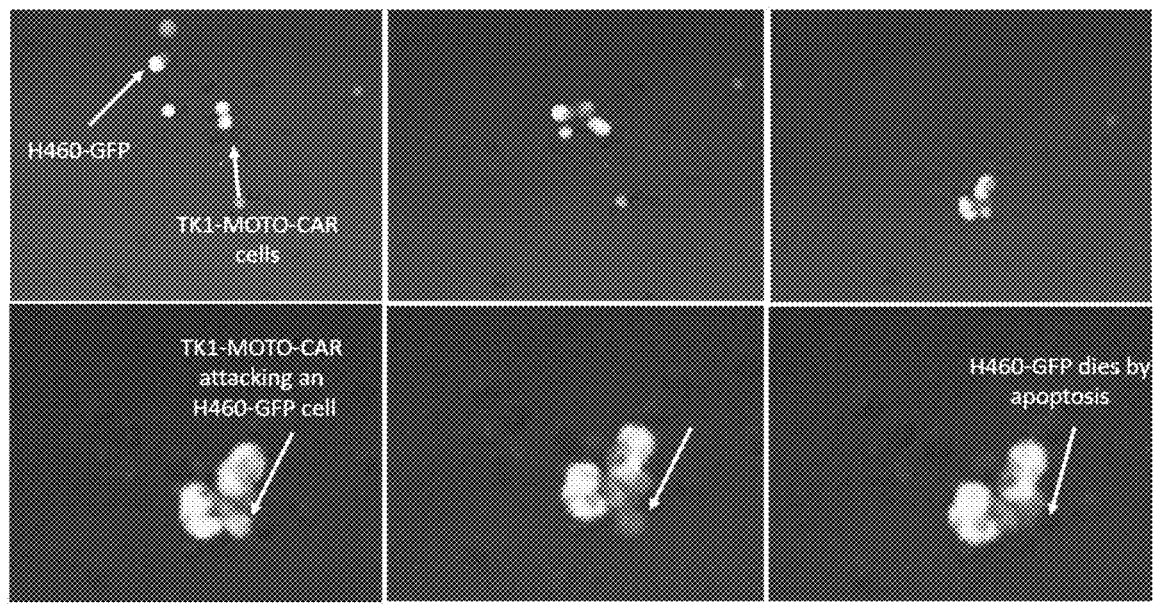

FIG. 32 presents six images of transduced macrophages expressing a chimeric receptor detecting, attacking, and inducing cell death in a lung cancer cell line (NCI-H460).

DETAILED DESCRIPTION

Described herein are chimeric receptors. Chimeric receptors comprise a cytoplasmic domain; a transmembrane domain; and an extracellular domain. In embodiments, the cytoplasmic domain comprises a cytoplasmic portion of a receptor that when activated polarizes a macrophage. In further embodiments, a wild-type protein comprising the cytoplasmic portion does not comprise the extracellular domain of the chimeric receptor. In embodiments, the binding of a ligand to the extracellular domain of the chimeric receptor activates the intracellular portion of the chimeric receptor. Activation of the intracellular portion of the chimeric receptor may polarize the macrophage into an M1 or M2 macrophage.

In certain embodiments, the cytoplasmic portion of the chimeric receptor may comprise a cytoplasmic domain from a toll-like receptor, myeloid differentiation primary response protein (MYD88) (SEQ ID NO:19), toll-like receptor 3 (TLR3) (SEQ ID NO:1), toll-like receptor 4 (TLR4) (SEQ ID NO:3), toll-like receptor 7 (TLR7) (SEQ ID NO:7), toll-like receptor 8 (TLR8) (SEQ ID NO:9), toll-like receptor 9 (TLR9) (SEQ ID NO:11), myelin and lymphocyte protein (MAL) (SEQ ID NO:21), interleukin-1 receptor-associated kinase 1 (IRAK1) (SEQ ID NO:23), low affinity immunoglobulin gamma Fc region receptor III-A (FCGR3A) (SEQ ID NO:15), low affinity immunoglobulin gamma Fc region receptor II-a (FCGR2A) (SEQ ID NO:13), high affinity immunoglobulin epsilon receptor subunit gamma (FCER1G) (SEQ ID NO:19), or sequences having at least 90% sequence identity to a cytoplasmic domain of any one of the foregoing. In certain embodiments, the cytoplasmic portion is not a cytoplasmic domain from a toll-like receptor, FCGR3A, IL-1 receptor, or IFN-gamma receptor. In embodiments, the cytosolic portion can be any polypeptide that, when activated, will result in the polarization of a macrophage.

In further embodiments, examples of ligands which bind to the extracellular domain may be, but are not limited to, Thymidine Kinase (TK1), Hypoxanthine-Guanine Phosphoribosyltransferase (HPRT), Receptor Tyrosine Kinase-Like Orphan Receptor 1 (ROR1), Mucin-16 (MUC-16), Epidermal Growth Factor Receptor vIII (EGFRvIII), Mesothelin, Human Epidermal Growth Factor Receptor 2 (HER2), Carcinoembryonic Antigen (CEA), B-Cell Maturation Antigen (BCMA), Glypican 3 (GPC3), Fibroblast Activation Protein (FAP), Erythropoietin-Producing Hepatocellular Carcinoma A2 (EphA2), Natural Killer Group 2D (NKG2D) ligands, Disialoganglioside 2 (GD2), CD19, CD20, CD30, CD33, CD123, CD133, CD138, and CD171. In certain embodiments, the ligand is not TK1 or HPRT.

Antibodies which may be adapted to generate extracellular domains of a chimeric receptor are well known in the art and are commercially available. Examples of commercially available antibodies include, but are not limited to: anti-HGPRT, clone 13H11.1 (EMD Millipore), anti-ROR1 (ab135669) (Abcam), anti-MUC1 [EP1024Y] (ab45167) (Abcam), anti-MUC16 [X75] (ab1107) (Abcam), anti-EGFRvIII [L8A4] (Absolute antibody), anti-Mesothelin [EPR2685(2)] (ab134109) (Abcam), HER2 [3B5] (ab16901) (Abcam), anti-CEA (LS-C84299-1000) (LifeSpan BioSciences), anti-BCMA (ab5972) (Abcam), anti-Glypican 3 [9C2] (ab129381) (Abcam), anti-FAP (ab53066) (Abcam), anti-EphA2 [RM-0051-8F21] (ab73254) (Abcam), anti-GD2 (LS-0546315) (LifeSpan BioSciences), anti-CD19 [2E2B6B10] (ab31947) (Abcam), anti-CD20 [EP459Y] (ab78237) (Abcam), anti-CD30 [EPR4102] (ab134080) (Abcam), anti-CD33 [SP266] (ab199432) (Abcam), anti-CD123 (ab53698) (Abcam), anti-CD133 (BioLegend), anti-CD123 (1A3H4) ab181789 (Abcam), and anti-CD171 (L1.1) (Invitrogen antibodies). Techniques for creating antibody fragments, such as ScFvs, from known antibodies are routine in the art. Further, generating sequences encoding such fragments and recombinantly including them in as part of a polynucleotide encoding a chimeric protein is also routine in the art.

In certain embodiments, the extracellular domain may comprise an antibody or a fragment there of that specifically binds to a ligand. Examples of antibodies and fragments thereof include, but are not limited to IgAs, IgDs, IgEs, IgGs, IgMs, Fab fragments, F(ab')$_2$ fragments, monovalent antibodies, ScFv fragments, scRv-Fc fragments, IgNARs, hcIgGs, VhH antibodies, nanobodies, and alphabodies. In additional embodiments, the extracellular domain may comprise any amino acid sequence that allows for the specific binding of a ligand, including, but not limited to, dimerization domains, receptors, binding pockets, etc.

In embodiments, the chimeric receptor may contain a linker. Without limitation, the linker may be located between the extracellular domain and the transmembrane domain of the chimeric receptor. Without limitation, the linker may be a G linker, a GS linker, a G4S linker, an EAAAK linker, a PAPAP linker, or an (Ala-Pro)$_n$ linker. Other examples of linkers are well known in the art.

In embodiments, the chimeric receptor may contain a hinge region. Without limitation, the hinge region may be located between the extracellular domain and the transmembrane domain of the chimeric receptor. In further embodiments, the hinge region may be located between a linker and the transmembrane domain. Without limitation, the linker may be a leucine rich repeat (LRR), or a hinge region from a toll-like receptor, an IgG, IgG4, CD8m or FcγIIIa-hing. In embodiments, cysteines in the hinge region may be replaced with serines. Other examples of hinge regions are well known in the art.

Chimeric receptors as described herein may comprise one or more of SEQ ID NOS:1, 3, 4, 5, 7, 9, 11, 13, 15, 17, 19, 21, 23, and 25-34, fragments of any of thereof, and/or polypeptides having at least 90% sequence identity to at least one of SEQ ID NOS:1, 3, 4, 5, 7, 9, 11, 13, 15, 17, 19, 21, 23, and 25-34 or fragments thereof. Examples of chimeric receptors include, but are not limited to, SEQ ID NOS:35-54, or a homologue or fragment thereof. In another embodiment, the polypeptide comprises an amino acid sequence selected from the group consisting of a polypeptide having at least 90% sequence identity to at least one of SEQ ID NOS:35-54.

Embodiments include nucleic acid sequences comprising a nucleic acid sequence encoding a chimeric receptor as described above. Examples of such nucleic acids may comprise one or more of SEQ ID NOS:2, 6, 8, 10, 12, 14, 16, 18, 20, 22, and 24, fragments of any of thereof, and/or nucleic acids having at least 90% sequence identity to at least one of SEQ ID NOS:2, 6, 8, 10, 12, 14, 16, 18, 20, 22, and 24 or fragments thereof. Further examples include nucleic acids encoding one or more of SEQ ID NOS:24-54 and fragments of any of thereof.

In embodiments, the chimeric receptors may be glycosylated, pegylated, and/or otherwise post-translationally modified. Further, the nucleic acid sequence may be part of a vector. By way of example, the vector may be a plasmid, phage, cosmid, artificial chromosome, viral vector, AAV vector, adenoviral vector, or lentiviral vector. In certain embodiments, a nucleic acid encoding a chimeric receptor may be operably linked to a promoter and/or other regulatory sequences (e.g., enhancers, silencers, insulators, locus control regions, cis-acting elements, etc.).

Further embodiments include cells comprising a chimeric receptor or nucleic acids encoding a chimeric receptor. Non-limiting examples of such cells include myeloid cells, myeloid progenitor cells, monocytes, neutrophils, basophils, eosinophils, megakaryocytes, T cells, B cells, natural killer cells, leukocytes, lymphocytes, dendritic cells, and macrophages.

Embodiments include methods of polarizing a macrophage by contacting a macrophage comprising a chimeric receptor with a ligand for the extracellular domain of the chimeric receptor; binding the ligand to the extracellular domain of the chimeric receptor. The binding of the ligand to the extracellular domain of the chimeric receptor activates the cytoplasmic portion and the activation of the cytoplasmic portion polarizes the macrophage.

Nucleotide, polynucleotide, or nucleic acid sequence will be understood according to the present disclosure as meaning both a double-stranded or single-stranded DNA or RNA in the monomeric and dimeric (so-called in tandem) forms and the transcription products of the DNAs or RNAs.

Aspects of the disclosure relate nucleotide sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning, and subcloning, it being possible for the sequences to be carried by vectors.

A nucleotide sequence fragment will be understood as designating any nucleotide fragment, and may include, by way of non-limiting examples, length of at least 8, 12, 20, 25, 50, 75, 100, 200, 300, 400, 500, 1000, or more, consecutive nucleotides of the sequence from which it originates.

A specific fragment of a nucleotide sequence will be understood as designating any nucleotide fragment of, having, after alignment and comparison with the corresponding wild-type sequence, at least one less nucleotide or base.

Homologous nucleotide sequence as used herein is understood as meaning a nucleotide sequence having at least a percentage identity with the bases of a nucleotide sequence of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%, this percentage being purely statistical and it being possible to distribute the differences between the two nucleotide sequences at random and over the whole of their length.

Specific homologous nucleotide sequences in the sense of the present disclosure is understood as meaning a homologous sequence having at least one sequence of a specific fragment, such as defined above. The "specific" homologous sequences can comprise, for example, the sequences corresponding to a genomic sequence or to the sequences of its fragments representative of variants of the genomic sequence. These specific homologous sequences can thus correspond to variations linked to mutations within the sequence and especially correspond to truncations, substitutions, deletions and/or additions of at least one nucleotide. The homologous sequences can likewise correspond to variations linked to the degeneracy of the genetic code.

The term "degree or percentage of sequence homology" refers to "degree or percentage of sequence identity between two sequences after optimal alignment" as defined in the present application.

Two nucleotide sequences are said to be "identical" if the sequence of amino-acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2: 482 (1981), by the homology alignment algorithm of Neddleman and Wunsch, *J. Mol. Biol.* 48: 443 (1970), by the search for similarity method of Pearson and Lipman, *Proc. Natl. Acad. Sci.* (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, the algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

In the BLAST N or BLAST P "BLAST 2 sequence," software which is available in the web site worldwideweb.ncbi.nlm.nih.gov/gorf/bl2.html, and habitually used by the inventors and in general by the skilled person for comparing and determining the identity between two sequences, gap cost which depends on the sequence length to be compared is directly selected by the software (i.e., 11.2 for substitution matrix BLOSUM-62 for length>85).

Complementary nucleotide sequence of a sequence as used herein is understood as meaning any DNA whose nucleotides are complementary to those of the sequences and whose orientation is reversed (antisense sequence).

Hybridization under conditions of stringency with a nucleotide sequence as used herein is understood as meaning hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments described above are advantageously the following.

The hybridization is carried out at a preferential temperature of 65° C. in the presence of SSC buffer, 1×SSC corresponding to 0.15 M NaCl and 0.05 M Na citrate. The washing steps, for example, can be the following: 2×SSC, at ambient temperature followed by two washes with 2×SSC, 0.5% SDS at 65° C.; 2×0.5×SSC, 0.5% SDS; at 65° C. for 10 minutes each.

The conditions of intermediate stringency, using, for example, a temperature of 42° C. in the presence of a 2×SSC buffer, or of less stringency, for example a temperature of 37° C. in the presence of a 2×SSC buffer, respectively require a globally less significant complementarity for the hybridization between the two sequences.

The stringent hybridization conditions described above for a polynucleotide with a size of approximately 350 bases will be adapted by the person skilled in the art for oligonucleotides of greater or smaller size, according to the teaching of Sambrook et al., 1989.

Among the nucleotide sequences described herein, are those which can be used as a primer or probe in methods allowing the homologous sequences to be obtained, these methods, such as the polymerase chain reaction (PCR), nucleic acid cloning, and sequencing, being well known to the person skilled in the art.

Among the nucleotide sequences are those which can be used as a primer or probe in methods allowing the presence of specific nucleic acids, one of their fragments, or one of their variants such as defined below to be determined. In embodiments, the nucleotide sequences may comprise fragments of SEQ ID NOS:2, 6, 8, 10, 12, 14, 16, 18, 20, 22, and 24 which encode a transmembrane domain, cytosolic domain, or a portion thereof. Further fragments may include nucleotide sequences encoding linkers, hinges, or fragments thereof such as nucleotides encoding one or more of SEQ ID NOS:26-34. Further fragments may include fragments of nucleotide sequences encoding one or more of SEQ ID NOS:35-54.

The nucleotide sequence fragments can be obtained, for example, by specific amplification, such as PCR, or after digestion with appropriate restriction enzymes of nucleotide sequences, these methods in particular being described in the work of Sambrook et al., 1989. Also, such fragments may be obtained with gene synthesis standard technology available from companies such as GENSCRIPT®. Such representative fragments can likewise be obtained by chemical synthesis according to methods well known to persons of ordinary skill in the art.

Modified nucleotide sequence will be understood as meaning any nucleotide sequence obtained by mutagenesis according to techniques well known to the person skilled in the art, and containing modifications with respect to a wild-type sequence, for example mutations in the regulatory and/or promoter sequences of polypeptide expression, especially leading to a modification of the rate of expression of the polypeptide or to a modulation of the replicative cycle.

Modified nucleotide sequence will likewise be understood as meaning any nucleotide sequence coding for a modified polypeptide such as defined below.

Disclosed are nucleotide sequences encoding a chimeric receptor, the nucleotide sequences comprising nucleotide sequences selected from SEQ ID NOS:2, 6, 8, 10, 12, 14, 16, 18, 20, 22, and 24 or one of their fragments. Such fragments may encode particular domains such as transmembrane domains or cytosolic domains or portions thereof. Further nucleotide sequences encoding a chimeric receptor may include nucleotide sequences encoding linkers, hinges, or fragments thereof such as nucleotides encoding one or more of SEQ ID NOS:26-34. Nucleotide sequences encoding a chimeric receptor may further nucleotide sequences encoding one or more of SEQ ID NOS:35-54 or fragments thereof.

Embodiments likewise relate to nucleotide sequences characterized in that they comprise a nucleotide sequence selected from: a) at least one of a nucleotide sequence of SEQ ID NOS:2, 6, 8, 10, 12, 14, 16, 18, 20, 22, and 24, a nucleotide sequence encoding at least one of SEQ ID NOS:25-54, or one of their fragments; b) a nucleotide sequence of a specific fragment of a sequence such as defined in a); c) a homologous nucleotide sequence having at least 80% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

Among the nucleotide sequences are the nucleotide sequences of SEQ ID NOS:2, 6, 8, 10, 12, 14, 16, 18, 20, 22, and 24, a nucleotide sequence encoding at least one of SEQ ID NOS:25-54, or fragments thereof and any nucleotide sequences which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the at least one of the sequences of SEQ ID NOS: 2, 6, 8, 10, 12, 14, 16, 18, 20, 22, and 24 a nucleotide sequence encoding at least one of SEQ ID NOS:25-54, or fragments thereof. The homologous sequences can comprise, for example, the sequences corresponding to the wild-type sequences. In the same manner, these specific homologous sequences can correspond to variations linked to mutations within the wild-type sequence and especially correspond to truncations, substitutions, deletions and/or additions of at least one nucleotide. As will be apparent to one of ordinary skill in the art, such homologues are easily created and identified using standard techniques and publicly available computer programs such as BLAST. As such, each homologue referenced above should be considered as set forth herein and fully described.

Embodiments comprise the chimeric receptors coded for by a nucleotide sequence described herein, or fragments thereof, whose sequence is represented by a fragment. Amino acid sequences corresponding to the polypeptides which can be coded for according to one of the three possible reading frames of at least one of the sequences of SEQ ID NOS:35-54.

Embodiments likewise relate to chimeric receptors, characterized in that they comprise a polypeptide selected from at least one of the amino acid sequences of SEQ ID NOS:1, 3, 5, 7, 9, 11, 13, 15, 17, 19, 21, 23, and 25-54, or one of their fragments.

Among the polypeptides, according to embodiments, are the polypeptides of amino acid sequence SEQ ID NOS:3, 5, 7, 9, 11, 13, 15, 17, 19, 21, 23, and 25-54, or fragments thereof or any other polypeptides which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with at least one of the sequences of SEQ ID NOS:1, 3, 5, 7, 9, 11, 13, 15, 17, 19, 21, 23, and 25-54 or fragments thereof. As will be apparent to one of ordinary skill in the art, such homologues are easily created and identified using standard techniques and publicly available computer programs such as BLAST. As such, each homologue referenced above should be considered as set forth herein and fully described.

Embodiments also relate to the polypeptides, characterized in that they comprise a polypeptide selected from: a) a specific fragment of at least 5 amino acids of a polypeptide of an amino acid sequence; b) a polypeptide homologous to a polypeptide such as defined in a); c) a specific biologically active fragment of a polypeptide such as defined in a) orb); and d) a polypeptide modified by a polypeptide such as defined in a), b) or c).

In the present description, the terms polypeptide, peptide and protein are interchangeable.

In embodiments, the chimeric receptors may be glycosylated, pegylated, and/or otherwise post-translationally modified. In further embodiments, glycosylation, pegylation, and/or other posttranslational modifications may occur in vivo or in vitro and/or may be performed using chemical techniques. In additional embodiments, any glycosylation, pegylation and/or other posttranslational modifications may be N-linked or O-linked.

In embodiments any one of the chimeric receptors may be enzymatically or functionally active such that, when the extracellular domain is bound by a ligand, a signal is transduced to polarize a macrophage.

As used herein, a "polarized macrophage" is a macrophage that correlates with an M1 or M2 macrophage phenotype. M1 polarized macrophages secrete IL-12 and IL-23. The determination of a macrophage as polarized to M1 may be performed by measuring the expression of IL-12 and/or IL-23 using a standard cytokine assay and comparing that expression to the expression by newly differentiated unpolarized macrophages. Alternatively, the determination can be made by determining if the cells are CD14+, CD80+, CD206+, and CDCD163−. M2 polarized macrophages secrete IL-10. The determination of a macrophage as polarized to M2 may be performed by measuring the expression of IL-10 using a standard cytokine assay and comparing that expression to the expression by newly differentiated unpolarized macrophages. Alternatively, the determination can be made by determining if the cells are CD14+, CD80−, CD206+, and CDCD163+

Aspects of the disclosure relate to chimeric receptors obtained by genetic recombination, or alternatively by chemical synthesis and that they may thus contain unnatural amino acids, as will be described below.

A "polypeptide fragment" according to the embodiments is understood as designating a polypeptide containing at least 5 consecutive amino acids, preferably 10 consecutive amino acids or 15 consecutive amino acids.

Herein, a specific polypeptide fragment is understood as designating the consecutive polypeptide fragment coded for by a specific fragment a nucleotide sequence.

"Homologous polypeptide" will be understood as designating the polypeptides having, with respect to the natural polypeptide, certain modifications such as, in particular, a deletion, addition, or substitution of at least one amino acid, a truncation, a prolongation, a chimeric fusion, and/or a mutation. Among the homologous polypeptides, those are preferred whose amino acid sequence has at least 80% or 90%, homology with the sequences of amino acids of polypeptides described herein.

"Specific homologous polypeptide" will be understood as designating the homologous polypeptides such as defined above and having a specific fragment of polypeptide polypeptides described herein.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. As will be apparent to one of ordinary skill in the art, such substitutions are easily created and identified using standard molecular biology techniques and publicly available computer programs such as BLAST. As such, each substitution referenced above should be considered as set forth herein and fully described.

These equivalent amino acids can be determined either by depending on their structural homology with the amino acids which they substitute, or on results of comparative tests of biological activity between the different polypeptides, which are capable of being carried out.

By way of nonlimiting example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

In a further embodiment, substitutions are limited to substitutions in amino acids not conserved among other proteins which have similar identified enzymatic activity. For example, one of ordinary skill in the art may align proteins of the same function in similar organisms and determine which amino acids are generally conserved among proteins of that function. One example of a program that may be used to generate such alignments is word-lwideweb.charite.de/bioinf/strap/ in conjunction with the databases provided by the NCBI.

Thus, according to one embodiment, substitutions or mutation may be made at positions that are generally conserved among proteins of that function. In a further embodiment, nucleic acid sequences may be mutated or substituted such that the amino acid they code for is unchanged (degenerate substitutions and/mutations) and/or mutated or substituted such that any resulting amino acid substitutions or mutation are made at positions that are generally conserved among proteins of that function.

The specific homologous polypeptides likewise correspond to polypeptides coded for by the specific homologous nucleotide sequences such as defined above and thus comprise in the present definition the polypeptides which are mutated or correspond to variants which can exist in wild-type sequences, and which especially correspond to truncations, substitutions, deletions, and/or additions of at least one amino acid residue.

"Specific biologically active fragment of a polypeptide" as used herein will be understood in particular as designating a specific polypeptide fragment, such as defined above, having at least one of the characteristics of polypeptides described herein. In certain embodiments the peptide is capable of behaving as chimeric antigen receptor that when activated polarizes a macrophage.

"Modified polypeptide" of a polypeptide as used herein is understood as designating a polypeptide obtained by genetic recombination or by chemical synthesis as will be described below, having at least one modification with respect to a wild-type sequence. These modifications may or may not be able to bear on amino acids at the origin of specificity, and/or of activity, or at the origin of the structural conformation, localization, and of the capacity of membrane insertion of the polypeptide as described herein. It will thus be possible to create polypeptides of equivalent, increased, or decreased activity, and of equivalent, narrower, or wider specificity. Among the modified polypeptides, it is necessary to mention the polypeptides in which up to 5 or more amino acids can be modified, truncated at the N- or C-terminal end, or even deleted or added.

The methods allowing the modulations on eukaryotic or prokaryotic cells to be demonstrated are well known to the person of ordinary skill in the art. It is likewise well understood that it will be possible to use the nucleotide sequences coding for the modified polypeptides for the modulations, for example through vectors and described below.

The preceding modified polypeptides can be obtained by using combinatorial chemistry, in which it is possible to systematically vary parts of the polypeptide before testing them on models, cell cultures or microorganisms for example, to select the compounds which are most active or have the properties sought.

Chemical synthesis likewise has the advantage of being able to use unnatural amino acids, or nonpeptide bonds.

Thus, in order to improve the duration of life of the polypeptides, it may be of interest to use unnatural amino acids, for example in D form, or else amino acid analogs, especially sulfur-containing forms, for example.

Finally, it will be possible to integrate the structure of the polypeptides, its specific or modified homologous forms, into chemical structures of polypeptide type or others. Thus, it may be of interest to provide at the N- and C-terminal ends compounds not recognized by proteases.

The nucleotide sequences coding for a polypeptide are likewise disclosed herein.

Embodiments likewise relates to nucleotide sequences utilizable as a primer or probe, characterized in that the sequences are selected from the nucleotide sequences described herein.

It is well understood that various embodiments likewise relate to specific polypeptides including chimeric receptors, coded for by nucleotide sequences, capable of being obtained by purification from natural polypeptides, by genetic recombination or by chemical synthesis by procedures well known to the person skilled in the art and such as described in particular below. In the same manner, the labeled or unlabeled mono- or polyclonal antibodies directed against the specific polypeptides coded for by the nucleotide sequences are also encompassed by this disclosure.

Embodiments additionally relate to the use of a nucleotide sequence as a primer or probe for the detection and/or the amplification of nucleic acid sequences.

The nucleotide sequences according to embodiments can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least 8 nucleotides, preferably of at least 12 nucleotides, and even more preferentially at least 20 nucleotides.

Other amplification techniques of the target nucleic acid can be advantageously employed as alternatives to PCR.

The nucleotide sequences described herein, in particular the primers, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); the TMA technique (Transcription Mediated Amplification).

The polynucleotides, including chimeric receptors, can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al. as well as by Stone et al. in 1996.

In the case where the target polynucleotide to be detected is possibly an RNA, for example an mRNA, it will be possible to use, prior to the employment of an amplification reaction with the aid of at least one primer or to the employment of a detection procedure with the aid of at least one probe, an enzyme of reverse transcriptase type in order to obtain a cDNA from the RNA contained in the biological sample. The cDNA obtained will thus serve as a target for the primer(s) or the probe(s) employed in the amplification or detection procedure.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

Embodiments also comprise the nucleotide sequences utilizable as a probe or primer, characterized in that they are labeled with a radioactive compound or with a nonradioactive compound.

The unlabeled nucleotide sequences can be used directly as probes or primers, although the sequences are generally labeled with a radioactive isotope ($^{32}P$, $^{35}S$, $^{3}H$, $^{125}I$) or with a nonradioactive molecule (biotin, acetylaminofluorene, digoxigenin, 5-bromodeoxyuridine, fluorescein) to obtain probes which are utilizable for numerous applications.

Examples of nonradioactive labeling of nucleotide sequences are described, for example, in French Patent No. 78.10975 or by Urdea et al. or by Sanchez-Pescador et al. in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

Various embodiments likewise comprise the nucleotide sequences or polypeptide sequences described herein, characterized in that they are immobilized on a support, covalently or noncovalently.

According to another advantageous mode of employing nucleotide sequences, the latter can be used immobilized on a support and can thus serve to capture, by specific hybridization, the target nucleic acid obtained from the biological sample to be tested. If necessary, the solid support is separated from the sample and the hybridization complex formed between the capture probe and the target nucleic acid is then detected with the aid of a second probe, a so-called detection probe, labeled with an easily detectable element.

Another aspect is a vector for the cloning and/or expression of a sequence, characterized in that it contains a nucleotide sequence described herein.

The vectors, characterized in that they contain the elements allowing the integration, expression and/or the secretion of the nucleotide sequences in a determined host cell, are likewise provided.

The vector may then contain a promoter, signals of initiation and termination of translation, as well as appropriate regions of regulation of transcription. It may be able to be maintained stably in the host cell and can optionally have particular signals specifying the secretion of the translated protein. These different elements may be chosen as a function of the host cell used. To this end, the nucleotide sequences described herein may be inserted into autonomous replication vectors within the chosen host, or integrated vectors of the chosen host.

Such vectors will be prepared according to the methods currently used by the person skilled in the art, and it will be possible to introduce the clones resulting therefrom into an appropriate host by standard methods, such as, for example, calcium phosphate precipitation, lipofection, electroporation, and thermal shock.

The vectors according are, for example, vectors of plasmid or viral origin. Examples of vectors for the expression of polypeptides described herein are plasmids, phages, cosmids, artificial chromosomes, viral vectors, AAV vectors, baculovirus vectors, adenoviral vectors, lentiviral vectors, retroviral vectors, chimeric viral vectors, and chimeric adenoviridae such as AD5/F35.

These vectors are useful for transforming host cells in order to clone or to express the nucleotide sequences described herein.

Embodiments likewise comprise the host cells transformed by a vector.

These cells can be obtained by the introduction into host cells of a nucleotide sequence inserted into a vector such as defined above, then the culturing of the cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as plants cells, such as *Arabidopsis* sp., and animal cells, in particular the cultures of mammalian cells (Edwards and Aruffo, 1993), for example, HEK 293, cells, HEK 293T cells, Chinese hamster ovary (CHO) cells, myeloid cells, myeloid progenitor cells, monocytes, neutrophils, basophils, eosinophils, megakaryocytes, T cells, B cells, natural killer cells, leukocytes, lymphocytes, dendritic cells, and macrophages, but likewise the cells of insects in which it is possible to use procedures employing baculoviruses, for example sf9 insect cells (Luckow, 1993).

Embodiments likewise relate to organisms comprising one of the transformed cells.

The obtainment of transgenic organisms expressing one or more of the nucleic acids or part of the nucleic acids may be carried out in, for example, rats, mice, or rabbits according to methods well known to the person skilled in the art, such as by viral or nonviral transfections. It will be possible to obtain the transgenic organisms expressing one or more of the genes by transfection of multiple copies of the genes under the control of a strong promoter of ubiquitous nature, or selective for one type of tissue. It will likewise be possible to obtain the transgenic organisms by homologous recombination in embryonic cell strains, transfer of these cell strains to embryos, selection of the affected chimeras at the level of the reproductive lines, and growth of the chimeras.

The transformed cells as well as the transgenic organisms are utilizable in procedures for preparation of recombinant polypeptides.

It is today possible to produce recombinant polypeptides in relatively large quantity by genetic engineering using the cells transformed by expression vectors or using transgenic organisms.

The procedures for preparation of a polypeptide, such as a chimeric receptor, in recombinant form, characterized in that they employ a vector and/or a cell transformed by a vector and/or a transgenic organism comprising one of the transformed cells are themselves comprised in in the present disclosure.

As used herein, "transformation" and "transformed" relate to the introduction of nucleic acids into a cell, whether prokaryotic or eukaryotic. Further, "transformation" and "transformed," as used herein, need not relate to growth control or growth deregulation.

Among the procedures for preparation of a polypeptide, such as a chimeric receptor, in recombinant form, the preparation procedures employing a vector, and/or a cell transformed by the vector and/or a transgenic organism comprising one of the transformed cells, containing a nucleotide sequence, such as those encoding a chimeric receptor.

A variant according, as used herein, may consist of producing a recombinant polypeptide fused to a "carrier" protein (chimeric protein). The advantage of this system is that it may allow stabilization of and/or a decrease in the proteolysis of the recombinant product, an increase in the solubility in the course of renaturation in vitro and/or a simplification of the purification when the fusion partner has an affinity for a specific ligand.

More particularly, embodiments relate to a procedure for preparation of a polypeptide comprising the following steps: a) culture of transformed cells under conditions allowing the expression of a recombinant polypeptide of nucleotide sequence; b) if need be, recovery of the recombinant polypeptide.

When the procedure for preparation of a polypeptide, such as a chimeric receptor, employs a transgenic organism, the recombinant polypeptide may then extracted from the organism or left in place.

Embodiments also relate to a polypeptide which is capable of being obtained by a procedure such as described previously.

Embodiments also comprise a procedure for preparation of a synthetic polypeptide, characterized in that it uses a sequence of amino acids of polypeptides.

This disclosure likewise relates to a synthetic polypeptide, such as a chimeric receptor, obtained by a procedure.

The polypeptides, such as chimeric receptors, can likewise be prepared by techniques which are conventional in the field of the synthesis of peptides. This synthesis can be carried out in homogeneous solution or in solid phase.

For example, recourse can be made to the technique of synthesis in homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

Recourse may also be made to the technique described by Merrifield.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids which are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

These hybrid molecules can be formed, in part, of a polypeptide carrier molecule or of fragments thereof, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen.

The polypeptides, including chimeric receptors, the antibodies described below and the nucleotide sequences encoding any of the foregoing can advantageously be employed in procedures for the polarization of a macrophage.

In embodiments, a nucleic acid sequence encoding a chimeric receptor is provided to a cell. The cell may then express the encoded chimeric receptor. The expressed chimeric receptor may be present on the surface of the cell or in the cytoplasm. In particular embodiments, the cell expressing the chimeric receptor is a macrophage. The macrophage expressed chimeric receptor may bind a ligand, and binding of the ligand may activate the chimeric receptor so as to induce polarization of the macrophage as previously described.

In embodiments, the cell provided with the nucleic acid sequence encoding a chimeric receptor may be isolated from a subject. After the cell is provided with the nucleic acid, the cell may be returned to the subject from whom it was obtained, for example by injection or transfusion. In other embodiments, the cell provided with the nucleic acid may be provided by a donor. After the donor cell is provided with the nucleic acid, the cell may then be provided to an individual other than the donor. Examples of donor cells include, but are not limited to primary cells from a subject and cells from a cell line.

In other embodiments, chimeric receptors may be introduced directly into cells. Any method of introducing a protein into cell may be used, including, but not limited to, microinjection, electroporation, membrane fusion, and the use of protein transduction domains. After the cell is provided with chimeric receptors, the cell may be returned to the subject from whom it was obtained, for example by injection or transfusion. In other embodiments, the cell provided with the chimeric receptors is provided by a donor. After the donor cell is provided with the nucleic acid, the cell may then be provided to an individual other than the donor. Examples of donor cells include, but are not limited to primary cells from a subject and cells from a cell line.

Embodiments likewise relates to polypeptides, such as chimeric receptors, labeled with the aid of an adequate label, such as, of the enzymatic, fluorescent or radioactive type.

The polypeptides allow monoclonal or polyclonal antibodies to be prepared which are characterized in that they specifically recognize the polypeptide. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, associated with an adjuvant of the immune response, and then purification of the specific antibodies contained in the serum of the immunized animals on an affinity column on which the polypeptide which has served as an antigen has previously been immobilized. The polyclonal antibodies can also be prepared by purification, on an affinity column on which a polypeptide has previously been immobilized, of the antibodies contained in the serum of an animal immunologically challenged by a chimeric receptor, or a polypeptide or fragment thereof.

In addition, antibodies can be used to prepare other forms of binding molecules, including, but not limited to, IgAs, IgDs, IgEs, IgGs, IgMs, Fab fragments, F(ab')2 fragments, monovalent antibodies, scFv fragments, scRv-Fc fragments, IgNARs, hcIgGs, VhH antibodies, nanobodies, and alphabodies.

Embodiments likewise relates to mono- or polyclonal antibodies or their fragments, or chimeric antibodies, or fragments thereof, characterized in that they are capable of specifically recognizing a polypeptide described herein or a ligand of a polypeptide and/or chimeric receptor.

It will likewise be possible for the antibodies to be labeled in the same manner as described previously for the nucleic probes, such as a labeling of enzymatic, fluorescent or radioactive type. It will be also be possible to include such antibodies and/or fragments thereof as part of a chimeric receptor. By way of non-limiting example, such an antibody or fragment thereof may make up a portion of the extracellular domain of a chimeric receptor.

Embodiments are additionally directed at a procedure for the detection and/or identification of chimeric receptor in a sample, characterized in that it comprises the following steps: a) contacting of the sample with a mono- or polyclonal (under conditions allowing an immunological reaction between the antibodies and the chimeric receptor possibly present in the biological sample); b) demonstration of the antigen-antibody complex possibly formed.

The embodiments are described in additional detail in the following illustrative examples. Although the examples may represent only selected embodiments, it should be understood that the following examples are illustrative and not limiting.

EXAMPLES

Example 1: Isolation of ScFv Fragments for Specific Ligands cDNA was purified from a monoclonal antibody hybridoma cell (CB 1) expressing an antibody specific to human TK1. The isolated cDNA was used to amplify the heavy and light chains of the CB 1 variable region via polymerase chain reaction (PCR) Sequences from the heavy and light chain were confirmed using NCBI Blast. CB 1 heavy and light chains were fused together via site overlap extension (SOE) PCR to form a single chain fragment variable (scFv) using a G4S linker. The G4S linker was codon optimized for yeast and humans using the Codon Optimization tool provided by IDT (https://www.idtdna.com/CodonOpt) in order to maximize protein expression. The CB 1 scFv was cut out using restriction enzymes and inserted into a pMP71 CAR vector.

TK-1 and HPRT-specific human scFv fragments were isolated from a yeast antibody library. TK-1 and HPRT proteins were isolated, His-tagged, and purified. TK-1 and HPRT protein were labeled with an anti-His biotinylated antibody and added to the library to select for TK-1 and HPRT-specific antibody clones. TK-1 and HPRT antibody clones were alternately stained with streptavidin or anti-biotin microbeads and enriched using a magnetic column. Two additional rounds of sorting and selection were performed to isolate TK-1 and HPRT specific antibodies. For the final selection, possible TK-1 and HPRT antibody clones and their respective proteins were sorted by fluorescence-activated cell sorting (FACS) by alternately labeling with fluorescently-conjugated anti-HA or anti-c-myc antibodies to isolate TK-1 and HPRT specific antibodies. High affinity clones were selected for chimeric receptor construction. Other human antibodies or humanized antibodies from other animals could be selected or altered to be TK-1 or HPRT specific by using phage display or other recombination methods.

Selected scFv clones were then combined with human IgG1 constant domains to create an antibody for use in applications such as Western blot or ELISA in order to confirm the binding specificity of the scFv. The antibody construct was inserted into the pPNL9 yeast secretion vector and YVH10 yeast were transformed with the construct and induced to produce the antibody. Other expression systems such as E. coli or mammalian systems could also be used to secrete antibodies.

Isolation and Characterization of Protein-Specific Antibody Fragments.

Referring to FIG. 26, 105 yeast were incubated with 2.5 ug of protein of interest labeled with the fluorescent tag APC. The higher left (red) peak indicates yeast population that was not binding to the protein of interest (negative control). The lower left (blue) peak on the left illustrates yeast not expressing their surface protein while the high (blue) peak on the right indicates binding of the expressed antibody fragment to the protein of interest.

Structural Consensus among Antibodies Defines the Antigen 5 Binding Site, PLoS Comput. Biol. 8(2): e1002388. doi:10.1371/journal.pcbi.1002388, Kunik V, Ashkenazi S, Ofran Y (2012). Paratome: An online tool for systematic identification of antigen binding regions in antibodies based on sequence or structure, Nucleic Acids Res. 2012 July; 40 (Web Server issue):W521-4. doi: 10.1093/nar/gks480. Epub 2012 Jun. 6.

Example 2: Creation of Chimeric Receptors

Construction of Chimeric Receptor Vectors:

The first step in the process is the design of the nucleotide sequences for synthetic chimeric receptor genes and the selection of appropriate lentiviral vectors. All the vector design are carried out in genious software version 9.1.6. The sequences are retrieved from the Uniprot and the Human Protein Reference Data base and NCBI as well.

Vectors are synthesized with a combination of recombinant DNA techniques and gene synthesis.

Sequences for the Single chain variable fragments are produced with a humanized antibody yeast display library or a phage display library. Nucleic acids encoding ScFv specific for each of TK1, HPRT, ROR1, MUC-16, EGFRvIII, Mesothelin, HER2, CEA, BCMA, GPC3, FAP, EphA2, NKG2D ligands, GD2, CD19, CD20, CD30, CD33, CD123, CD133, CD138, and CD171. All possible combinations of nucleic acids encoding chimeric receptors having at least one of each of a), b), c), d), and e), wherein a), b), c), d), and e) are:
a) an ScFv specific for TK1, HPRT, ROR1, MUC-16, EGFRvIII, Mesothelin, HER2, CEA, BCMA, GPC3, FAP, EphA2, NKG2D ligands, GD2, CD19, CD20, CD30, CD33, CD123, CD133, CD138, and CD171;
b) a GS linker or no GS linker;
c) A hinge region selected from an LRR 5 amino acid short hinge, a LRR long hinge, an IgG4 short hinge, an IgG 119 amino acid medium hinge, and IgG4 long hinge, a CD8 hinge, a CD8 hinge with cysteines converted to serines, and no hinge;
d) a transmembrane domain selected from the transmembrane domains of MYD88, TLR3, TLR4, TLR7, TLR8, TLR9, MAL, IRAK1, FCGR2A, FCGR3A, and FCER1G; and
e) a cytosolic domain selected from the cytosolic domains of MYD88, TLR3, TLR4, TLR7, TLR8, TLR9, MAL, IRAK1, FCGR2A, FCGR3A, and FCER1G.

The foregoing nucleic acids encoding chimeric receptors are synthesized with a combination of recombinant DNA techniques and gene synthesis.

Macrophages are genetically modified with an integrated gene delivery method via lentiviral-mediated gene transfer to provide the nucleic acids encoding chimeric receptors. A third generation lentiviral system from addgene is used to package our lentiviral vectors. pHIV-dTomato (#21374) and pUltra-chilli (#48687) are the gene transfer plasmids. pCMV-VSV-G (#8454), pMDLg/pRRE (#12251), pRSV-Rev (#12253), pHCMV-AmphoEnv (#15799) are the packaging plasmids. A lentiviral mediated gene transfer of human lymphocytes has been standardized previously getting efficiencies up to 50% transduction. HEK293T cells are transfected with the calcium phosphate method (SIGMA CAPHOS). Around 10 µg of each packaging plasmid and 20 ug of vector encoding the chimeric receptor are used per transfection. After 48-36 hours viral particles are harvested and sterile filtered. Viral titration are determined infecting HT1080 and U937 cells.

The analysis is performed by flow cytometry detecting a red fluorescent protein. After viral titration human monocytes are transduced using retronectin plates (Clonetech, T100B) and the spin infection method Previous to lentiviral transduction, monocytes are isolated from whole PBMNCs by negative selection and magnetic sorting using the Monocyte Isolation Kit II, human (MACS130-091-153). After monocyte isolation cells are split in 2 nunclon 6-well plates (Thermo, 145380) seeding 1.5×106 cells in each well for each vector. One plate is immediately transduced while the second plate is used for ex-vivo differentiation of monocytes to M1 macrophages. The M1 macrophages are produced using the media M1-Macrophage Generation Medium DFX (Promocell, C-28055). After 7 days, macrophages are transduced and activated at day 9 with LPS (500×) (Affimetryx, 00-4976-03) and IFN-γ (Promokine, C-60724). The transduction efficiency is analyzed by flow cytometry. Transduced cells are separated by cell sorting using a FACS Aria cell sorter. After cell sorting transduced monocytes are ex vivo cultured for a couple of days before differentiation while differentiated macrophages can last a month.

Example 3: Polarization of Macrophages Through Chimeric Receptors

The transduced macrophages prepared in Example 2 are separately exposed to TK1, HPRT, ROR1, MUC-16, EGFRvIII, Mesothelin, HER2, CEA, BCMA, GPC3, FAP, EphA2, NKG2D conjugated ligands, GD2, CD19, CD20, CD30, CD33, CD123, CD133, CD138, and CD171 and tested for polarization to the M1 phenotype by monitoring the secretion of IL-12 and IL-23 using a standard cytokine assay or by measuring RNA production. Macrophages bearing chimeric receptors are polarized to the M1 phenotype when exposed to the ligand specific for the particular chimeric receptor and determined by increased secretion of IL-12 and/or IL-23. Ligands other than the specific ligand for the specific chimeric receptor display no increase in IL-12 and/or IL-21.

Example 4: Production of Monocyte-Derived Macrophages and Transduction

After 7 days of differentiation monocyte-derived macrophages had undergone phenotype changes. These changes where compared between transduced and non-transduced cells. As can be observed in FIG. 27, transduced cells have a more aggressive phenotype similar to M1 or classically activated macrophages. FIG. 27 shows images of Non-transduced and transduced monocyte-derived macrophages at day 8 of differentiation. No Interferon gamma and LPS was added at this point. It can be observed that the phenotype of macrophages transduced with a chimeric receptor is different from non-transduced macrophages. Transduced cells displayed a classically activated or M1-like phenotype indicating macrophage activation. The altered phenotype may be a combined effect of the transduction process and the expression of the new synthetic receptor.

FIG. 28 provides confirmation of the insertion and expression of constructs encoding a chimeric receptor as was confirmed by the expression of dTomato 48-72 hours after transduction. This demonstrates the successful transduction of human monocyte-derived macrophages.

Example 5: Transduction Efficiency

After day 10 of differentiation the transduction efficiency was assessed and macrophages expressing the chimeric receptor were cell sorted. Lentiviral transduction is challenging in macrophages. However, using HIV-1 based systems with EF1-α promoters almost 30% macrophage transduction was achieved. Transductions of the cells at early stages of macrophage differentiation displayed different transduction efficiencies. Monocytes or macrophages in earlier stages of differentiation are easier to transduce. Adenoviral transduction with the chimeric adenovirus AD5/F35 has emerged as another alternative for macrophage transduction. FIG. 29 shows the results of macrophages that were transduced being cell sorted using a FACSAria system. Around 30% of macrophage transduction was achieved using the lentiviral approach. The left most plot shows a control wherein only 0.58% of cells show fluorescence which would indicate expression of dTomato. The right two plots show a transduction efficiency of 27.1 percent after transduction.

Example 6: Immunophenotyping of Transduced Macrophages

Immunophenotyping of macrophages transduced with vectors for the expression of a chimeric receptor was performed to identify the activation state of the transduced cells. It has been reported that modifications of the extracellular domain of TLR-4 may induce constant activation of its signaling domain (Gay et al., 2014). Constant activation of the TLR-4 signaling could lead to macrophage activation or M1 phenotype. It is not know if the construct which was used, which is based on TLR-4, is able to trigger a constant activation of the signaling through the TIR domain taken from TLR-4. However, after the transduction process, a change in the phenotype was observed and a change in the expression of cell surface markers in the macrophages. This is likely due to a combination of the lentiviral transduction and the expression of the chimeric receptor protein. Expression of CD14, CD80, D206 and low expression of CD163 were indicators of macrophage polarization towards the M1 phenotype. The expression of these cell surface markers in was observed in the transduced cells. FIG. 30 presents six scatter plots of fluorescence activated cell sorting demonstrating the retention of dye (Alexa 647), and the expression of CD80, CD163, CD206, and CD14 in macrophages transduced with a chimeric receptor.

FIG. 31. Presents a histogram of the relative expression levels of M1 cells surface markers in macrophages transduced with a vector to express a chimeric receptor.

Example 7: In-Vitro Toxicity of TK1 Targeting Chimeric Receptor Transduced Macrophages Against NCI-11460 Cells The tumoricidal activity of TK1 targeting chimeric receptor transduced macrophages was tested against NCI-H460-GFP cells. The E:T ratio used was 1:10. The analysis was performed with confocal microscopy. Detection of fluorescence was performed every 5 minutes during a 12 hour period. It was observed during time lapse that TK1 targeting chimeric receptor transduced macrophages migrate toward H460-GFP cells and attack them. After the synapsis, specific cell death is induced in the target cell. As demonstrated by the images in FIG. 32, TK1 targeting chimeric receptor transduced macrophages can detect, attack and induce cell death in lung cancer cell lines expressing TK1. NCI-H460 cells were modified to express GFP. The tumoricidal activity of TK1 targeting chimeric receptor transduced macrophages was detected with confocal microscopy as a loss of fluorescence in the target cell.

The disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims and their legal equivalents.

TABLE OF REFERENCES

1. Hanahan, D., & Weinberg, R. a. (2011). Hallmarks of cancer: the next generation. *Cell*, 144(5), 646-74. http://doi.org/10.1016/j.cell.2011.02.013
2. American Cancer Society. (2015). *Cancer Facts & FIGS.* 2015.
3. Hoyert, D. L., & Xu, J. (2012). *National Vital Statistics Reports Deaths: Preliminary Data for* 2011 (Vol. 61).
4. Kurahara, H., Shinchi, H., Mataki, Y., Maemura, K., Noma, H., Kubo, F., . . . Takao, S. (2011). Significance of M2-polarized tumor-associated macrophage in pancreatic cancer. *The Journal of Surgical Research*, 167(2), e211-9. http://doi.org/10.1016/j.jss.2009.05.026
5. Steidl, C., Lee, T., & Shah, S. (2010a). Tumor-associated macrophages and survival in classic Hodgkin's lymphoma. *The New England Journal of Medicine*, 875-885. Retrieved from http://www.nejm.org/doi/full/10.1056/NEJMoa0905680
6. Eiró, N., & Vizoso, F. J. (2012). Inflammation and cancer. *World Journal of Gastrointestinal Surgery*, 4(3), 62-72. http://doi.org/10.4240/wjgs.v4.i3.62
7. Kelly, P. M., Davison, R. S., Bliss, E., & McGee, J. O. (1988). Macrophages in human breast disease: a quantitative immunohistochemical study. *British Journal of Cancer*, 57(2), 174-7. Retrieved from http://www.pubmedcentral.nih.gov/articlerender.fcgi?artid=2246436&tool=pmcentrez&rendertype=abstract
8. Lewis, C., & Leek, R. (1995). Cytokine regulation of angiogenesis in breast cancer: the role of tumor-associated macrophages. *Journal of Leukocyte . . .* , 57 (May), 747-751. Retrieved from http://www.jleukbio.org/content/57/5/747.short
9. Mantovani, A., Biswas, S. K., Galdiero, M. R., Sica, A., & Locati, M. (2013). Macrophage plasticity and polarization in tissue repair and remodelling. *The Journal of Pathology*, 229(2), 176-85. http://doi.org/10.1002/path.4133
10. Porta, C., Rimoldi, M., Raes, G., Brys, L., Ghezzi, P., Di Liberto, D., . . . Sica, A. (2009). Tolerance and M2 (alternative) macrophage polarization are related processes orchestrated by p50 nuclear factor kappaB. *Proceedings of the National Academy of Sciences of the United States of America*, 106(35), 14978-83. http://doi.org/10.1073/pnas.0809784106
11. Sica, A., & Mantovani, A. (2012). Macrophage plasticity and polarization: in vivo veritas. *The Journal of Clinical Investigation*, 122(3), 787-796. http://doi.org/10.1172/JCI59643DS1
12. Anderson, C. F., & Mosser, D. M. (2002). A novel phenotype for an activated macrophage: the type 2 activated macrophage. *Journal of Leukocyte Biology*, 72(1), 101-6. Retrieved from http://www.ncbi.nlm.nih.gov/pubmed/12101268
13. Ghassabeh, G. H., De Baetselier, P., Brys, L., Noel, W., Van Ginderachter, J. a, Meerschaut, S., . . . Raes, G. (2006). Identification of a common gene signature for type II cytokine-associated myeloid cells elicited in vivo in different pathologic conditions. *Blood*, 108(2), 575-83. http://doi.org/10.1182/blood-2005-04-1485
14. Liao, X., Sharma, N., & Kapadia, F. (2011). Kruppel-like factor 4 regulates macrophage polarization. *The Journal of Clinical Investigation*, 121(7). http://doi.org/10.1172/JCI45444DS1
15. Davis, M. J., Tsang, T. M., Qiu, Y., Dayrit, J. K., Freij, J. B., Huffnagle, G. B., & Olszewski, M. A. (2013). Macrophage M1/M2 polarization dynamically adapts to changes in cytokine microenvironments in *Cryptococcus neoformans* infection. *mBio*, 4(3), e00264-13. http://doi.org/10.1128/mBio.00264-13
16. Mantovani, A., Sozzani, S., Locati, M., Allavena, P., & Sica, A. (2002). Macrophage polarization: tumor-associated macrophages as a paradigm for polarized M2 mononuclear phagocytes. *Trends in Immunology*, 23(11), 549-55. Retrieved from http://www.ncbi.nlm.nih.gov/pubmed/12401408
17. Edin, S., Wikberg, M. L., Dahlin, A. M., Rutegård, J., Oberg, A., Oldenborg, P.-A., & Palmqvist, R. (2012). The distribution of macrophages with a m1 or m2 phenotype in relation to prognosis and the molecular characteristics of colorectal cancer. *PloS One*, 7(10), e47045. http://doi.org/10.1371/journal.pone.0047045
18. Forssell, J., Oberg, A., Henriksson, M. L., Stenling, R., Jung, A., & Palmqvist, R. (2007). High macrophage infiltration along the tumor front correlates with improved survival in colon cancer. *Clinical Cancer Research*, 13(5), 1472-9. http://doi.org/10.1158/1078-0432.CCR-06-2073
19. Guiducci, C., Vicari, A. P., Sangaletti, S., Trinchieri, G., & Colombo, M. P. (2005). Redirecting in vivo elicited tumor infiltrating macrophages and dendritic cells towards tumor rejection. *Cancer Research*, 65(8), 3437-46. http://doi.org/10.1158/0008-5472.CAN-04-4262
20. Baccala, R., Hoebe, K., Kono, D. H., Beutler, B., & Theofilopoulos, A. N. (2007). TLR-dependent and TLR-independent pathways of type I interferon induction in systemic autoimmunity. *Nature Medicine*, 13(5), 543-51. http://doi.org/10.1038/nm1590
21. Banerjee, S., Xie, N., Cui, H., Tan, Z., Yang, S., Icyuz, M., . . . Liu, G. (2013). MicroRNA let-7c regulates macrophage polarization. *Journal of Immunology* (Baltimore, Md.: 1950), 190(12), 6542-9. http://doi.org/10.4049/jimmunol.1202496
22. Murray, P. J., Allen, J. E., Biswas, S. K., Fisher, E. A., Gilroy, D. W., Goerdt, S., . . . Wynn, T. A. (2014). Macrophage Activation and Polarization: Nomenclature and Experimental Guidelines. *Immunity*, 41(1), 14-20. http://doi.org/10.1016/j.immuni.2014.06.008
23. Hao, N.-B., Lü, M.-H., Fan, Y.-H., Cao, Y.-L., Zhang, Z.-R., & Yang, S.-M. (2012). Macrophages in tumor microenvironments and the progression of tumors. *Clinical & Developmental Immunology*, 2012, 948098. http://doi.org/10.1155/2012/948098
24. Sinha, P., Clements, V. K., & Ostrand-Rosenberg, S. (2005). Reduction of myeloid-derived suppressor cells and induction of M1 macrophages facilitate the rejection of established metastatic disease. *Journal of Immunology*, 174(2), 636-45. Retrieved from http://www.ncbi.nlm.nih.gov/pubmed/15634881
25. Bingle, L., Brown, N. J., & Lewis, C. E. (2002). The role of tumour-associated macrophages in tumour progression: implications for new anticancer therapies. *The Journal of Pathology*, 196(3), 254-65. http://doi.org/10.1002/path.1027
26. Herbeuval, J.-P., Lambert, C., Sabido, O., Cottier, M., Fournel, P., Dy, M., & Genin, C. (2003). Macrophages from cancer patients: analysis of TRAIL, TRAIL receptors, and colon tumor. *Journal of the National Cancer Institute*, 95(8), 611-21. Retrieved from http://www.ncbi.nlm.nih.gov/pubmed/12697854
27. Ma, J., Liu, L., Che, G., Yu, N., Dai, F., & You, Z. (2010). The M1 form of tumor-associated macrophages in non-small cell lung cancer is positively associated with survival time. *BMC Cancer*, 10, 112. http://doi.org/10.1186/1471-2407-10-112
28. Ohri, C. M., Shikotra, A., Green, R. H., Waller, D. a, & Bradding, P. (2009). Macrophages within NSCLC tumour islets are predominantly of a cytotoxic M1 phenotype associated with extended survival. *The European Respiratory Journal*, 33(1), 118-26. http://doi.org/10.1183/09031936.00065708
29. Urban, J. L., Shepard, H. M., Rothstein, J. L., Sugarman, B. J., & Schreiber, H. (1986). Tumor necrosis factor: a potent effector molecule for tumor cell killing by activated macrophages. *Proceedings of the National Academy of Sciences of the United States of America*, 83(14), 5233-7. Retrieved from http://www.pubmedcentral.nih.gov/articlerender.fcgi?artid=323925&tool=pmcentrez&rendertype=abstract
30. Wong, S.-C., Puaux, A.-L., Chittezhath, M., Shalova, I., Kajiji, T. S., Wang, X., . . . Biswas, S. K. (2010). Macrophage polarization to a unique phenotype driven by B cells. *European Journal of Immunology*, 40(8), 2296-307. http://doi.org/10.1002/eji.200940288
31. Hardison, S. E., Herrera, G., Young, M. L., Hole, C. R., Wozniak, K. L., & Wormley, F. L. (2012). Protective immunity against pulmonary cryptococcosis is associated with STAT1-mediated classical macrophage activation. *Journal of Immunology* (Baltimore, Md.: 1950), 189(8), 4060-8. http://doi.org/10.4049/jimmunol.1103455
32. Wang, Y.-C., He, F., Feng, F., Liu, X.-W., Dong, G.-Y., Qin, H.-Y., . . . Han, H. (2010). Notch signaling determines the M1 versus M2 polarization of macrophages in antitumor immune responses. *Cancer Research*, 70(12), 4840-9. http://doi.org/10.1158/0008-5472.CAN-10-0269
33. Cai, X., Yin, Y., Li, N., Zhu, D., Zhang, J., Zhang, C.-Y., & Zen, K. (2012). Re-polarization of tumor-associated macrophages to pro-inflammatory M1 macrophages by microRNA-155. *Journal of Molecular Cell Biology*, 4(5), 341-3. http://doi.org/10.1093/jmcb/mjs044
34. Wei, Y., Nazari-Jahantigh, M., Chan, L., Zhu, M., Heyll, K., Corbalán-Campos, J., . . . Schober, A. (2013). The microRNA-342-5p fosters inflammatory macrophage activation through an Akt1- and microRNA-155-dependent pathway during atherosclerosis. *Circulation*, 127 (15), 1609-19. http://doi org/10.1161/CIRCULATIONAHA.112.000736
35. Squadrito, M. L., Etzrodt, M., De Palma, M., & Pittet, M. J. (2013). MicroRNA-mediated control of macrophages and its implications for cancer. *Trends in Immunology*, 34(7), 350-9. http://doi.org/10.1016/j.it.2013.02.003
36. Biswas, S. K., Gangi, L., Paul, S., Schioppa, T., Saccani, A., Sironi, M., . . . Sica, A. (2006). A distinct and unique transcriptional program expressed by tumor-associated macrophages (defective NF-kappaB and enhanced IRF-3/STAT1 activation). *Blood*, 107(5), 2112-22. http://doi.org/10.1182/blood-2005-01-0428
37. Steidl, C., Lee, T., & Shah, S. (2010b). Tumor-associated macrophages and survival in classic Hodgkin's lymphoma. *The New England Journal of Medicine*, 362(10), 875-885. Retrieved from http://www.nejm.org/doi/full/10.1056/NEJMoa0905680
38. Lin, E. Y., Li, J.-F., Gnatovskiy, L., Deng, Y., Zhu, L., Grzesik, D. a, . . . Pollard, J. W. (2006). Macrophages regulate the angiogenic switch in a mouse model of breast cancer. *Cancer Research*, 66(23), 11238-46. http://doi.org/10.1158/0008-5472.CAN-06-1278
39. Hagemann, T., Wilson, J., Burke, F., Kulbe, H., Li, N. F., Plüddemann, A., . . . Balkwill, F. R. (2006). Ovarian cancer cells polarize macrophages toward a tumor-associated phenotype. *The Journal of Immunology*, 176(8), 5023-32. Retrieved from http://www.ncbi.nlm.nih.gov/pubmed/16585599
40. Hagemann, T., Lawrence, T., McNeish, I., Charles, K. a, Kulbe, H., Thompson, R. G., . . . Balkwill, F. R. (2008). "Re-educating" tumor-associated macrophages by targeting NF-kappaB. *The Journal of Experimental Medicine*, 205(6), 1261-8. http://doi.org/10.1084/jem.20080108
41. Mandal, P., Pratt, B. T., Barnes, M., McMullen, M. R., & Nagy, L. E. (2011). Molecular mechanism for adiponectin-dependent M2 macrophage polarization: link between the metabolic and innate immune activity of full-length adiponectin. *The Journal of Biological Chemistry*, 286(15), 13460-9. http://doi.org/10.1074/jbc.M110.204644
42. Mantovani, A., Allavena, P., Sica, A., & Balkwill, F. (2008). Cancer-related inflammation. *Nature*, 454(7203), 436-44. http://doi.org/10.1038/nature07205
43. Cortez-Retamozo, V., Etzrodt, M., Newton, A., Rauch, P. J., Chudnovskiy, A., Berger, C., . . . Pittet, M. J. (2012). Origins of tumor-associated macrophages and neutrophils. *Proceedings of the National Academy of Sciences of the United States of America*, 109(7), 2491-6. http://doi.org/10.1073/pnas.1113744109
44. Hercus, T. R., Thomas, D., Guthridge, M. A., Ekert, P. G., King-Scott, J., Parker, M. W., & Lopez, A. F. (2009). The granulocyte-macrophage colony-stimulating factor receptor: linking its structure to cell signaling and its role in disease. *Blood*, 114(7), 1289-98. http://doi.org/10.1182/blood-2008-12-164004
45. Smith, H. O., Stephens, N. D., Qualls, C. R., Fligelman, T., Wang, T., Lin, C.-Y., . . . Pollard, J. W. (2013). The clinical significance of inflammatory cytokines in primary cell culture in endometrial carcinoma. *Molecular Oncology*, 7(1), 41-54. http://doi.org/10.1016/j.molonc.2012.07.002
46. West, R. B., Rubin, B. P., Miller, M. A., Subramanian, S., Kaygusuz, G., Montgomery, K., . . . van de Rijn, M. (2006). A landscape effect in tenosynovial giant-cell tumor from activation of CSF1 expression by a translocation in a minority of tumor cells. *Proceedings of the National Academy of Sciences of the United States of America*, 103(3), 690-5. http://doi.org/10.1073/pnas.0507321103
47. Lin, E. Y., & Pollard, J. W. (2007). Tumor-associated macrophages press the angiogenic switch in breast cancer. *Cancer Research*, 67(11), 5064-6. http://doi.org/10.1158/0008-5472.CAN-07-0912
48. Dalton, H. J., Armaiz-Pena, G. N., Gonzalez-Villasana, V., Lopez-Berestein, G., Bar-Eli, M., & Sood, A. K. (2014). Monocyte subpopulations in angiogenesis. *Cancer Research*, 74(5), 1287-93. http://doi.org/10.1158/0008-5472.CAN-13-2825
49. Saccani, A., Schioppa, T., Porta, C., Biswas, S. K., Nebuloni, M., Vago, L., . . . Sica, A. (2006). p50 nuclear factor-kappaB overexpression in tumor-associated macrophages inhibits M1 inflammatory responses and antitumor resistance. *Cancer Research*, 66(23), 11432-40. http://doi.org/10.1158/0008-5472.CAN-06-1867
50. Gazzaniga, S., Bravo, A. I., Guglielmotti, A., van Rooijen, N., Maschi, F., Vecchi, A., . . . Wainstok, R. (2007). Targeting tumor-associated macrophages and inhibition of MCP-1 reduce angiogenesis and tumor growth in a human melanoma xenograft. *The Journal of Investigative Dermatology*, 127(8), 2031-41. http://doi.org/10.1038/sj.jid.5700827
51. Luo, Y., Zhou, H., & Krueger, J. (2006). Targeting tumor-associated macrophages as a novel strategy against breast cancer. *Journal of Clinical Investigation*, 116(8), 2132-2141. http://doi.org/10.1172/JCI27648.2132
52. Zeisberger, S. M., Odermatt, B., Marty, C., Zehnder-Fjallman, a H. M., Ballmer-Hofer, K., & Schwendener, R. a. (2006). Clodronate-liposome-mediated depletion of tumour-associated macrophages: a new and highly effective antiangiogenic therapy approach. *British Journal of Cancer*, 95(3), 272-81. http://doi.org/10.1038/sj.bjc.6603240
53. Bettencourt-Dias, M., Giet, R., Sinka, R., Mazumdar, a, Lock, W. G., Balloux, F., . . . Glover, D. M. (2004).

Genome-wide survey of protein kinases required for cell cycle progression. *Nature*, 432(7020), 980-7. http://doi.org/10.1038/nature03160

54. Geschwind, J. H., Vali, M., & Wahl, R. (2006). Effects of 3 bromopyruvate (hexokinase 2 inhibitor) on glucose uptake in lewis rats using 2-(F-18) fluoro-2-deoxy-d-glucose. In 2006 *Gastrointestinal Cancers Symposium* (pp. 12-14).

55. Wolf, A., Agnihotri, S., Micallef, J., Mukherjee, J., Sabha, N., Cairns, R., . . . Guha, A. (2011). Hexokinase 2 is a key mediator of aerobic glycolysis and promotes tumor growth in human glioblastoma multiforme. *The Journal of Experimental Medicine*, 208(2), 313-26. http://doi.org/10.1084/jem.20101470

56. Blagih, J., & Jones, R. G. (2012). Polarizing macrophages through reprogramming of glucose metabolism. *Cell Metabolism*, 15(6), 793-5. http://doi.org/10.1016/j.cmet.2012.05.008

57. Haschemi, A., Kosma, P., Gille, L., Evans, C. R., Burant, C. F., Starkl, P., . . . Wagner, O. (2012). The sedoheptulose kinase CARKL directs macrophage polarization through control of glucose metabolism. *Cell Metabolism*, 15(6), 813-26. http://doi.org/10.1016/j.cmet.2012.040.023

58. Arranz, A., Doxaki, C., Vergadi, E., Martinez de la Torre, Y., Vaporidi, K., Lagoudaki, E. D., . . . Tsatsanis, C. (2012). Akt1 and Akt2 protein kinases differentially contribute to macrophage polarization. *Proceedings of the National Academy of Sciences of the United States of America*, 109(24), 9517-22. http://doi.org/10.1073/pnas.1119038109

59. Jones, R. G., & Thompson, C. B. (2007). Revving the engine: signal transduction fuels T cell activation. *Immunity*, 27(2), 173-8. http://doi.org/10.1016/j.immuni.2007.07.008

60. Shu, C. J., Guo, S., Kim, Y. J., Shelly, S. M., Nijagal, A., Ray, P., . . . Witte, O. N. (2005). Visualization of a primary anti-tumor immune response by positron emission tomography. *Proceedings of the National Academy of Sciences of the United States of America*, 102(48), 17412-7. http://doi.org/10.1073/pnas.0508698102

61. Van Ginderachter, J. A., Movahedi, K., Hassanzadeh Ghassabeh, G., Meerschaut, S., Beschin, A., Raes, G., & De Baetselier, P. (2006). Classical and alternative activation of mononuclear phagocytes: Picking the best of both worlds for tumor promotion. *Immunobiology*, 211(6), 487-501. Retrieved from http://www.sciencedirect.com/science/article/pii/S0171298506000829

62. Mills, C. D., Shearer, J., Evans, R., & Caldwell, M. D. (1992). Macrophage arginine metabolism and the inhibition or stimulation of cancer. *Journal of Immunology* (Baltimore, Md.: 1950), 149(8), 2709-14. Retrieved from http://www.ncbi.nlm.nih.gov/pubmed/1401910

63. Ji, Y., Sun, S., Xu, A., Bhargava, P., Yang, L., Lam, K. S. L., . . . Qi, L. (2012). Activation of natural killer T cells promotes M2 Macrophage polarization in adipose tissue and improves systemic glucose tolerance via interleukin-4 (IL-4)/STAT6 protein signaling axis in obesity. *The Journal of Biological Chemistry*, 287(17), 13561-71. http://doi.org/10.1074/jbc.M112.350066

64. Andreesen, R., Scheibenbogen, C., & Brugger, W. (1990). Adoptive transfer of tumor cytotoxic macrophages generated in vitro from circulating blood monocytes: a new approach to cancer immunotherapy. *Cancer Research*, 7450-7456. Retrieved from http://cancerres.aacrjournals.org/content/50/23/7450. short 65. Korbelik, M., Naraparaju, V. R., & Yamamoto, N. (1997). Macrophage-directed immunotherapy as adjuvant to photodynamic therapy of cancer. *British Journal of Cancer*, 75(2), 202-7. Retrieved from http://www.pubmedcentral.nih.gov/articlerender.fcgi?artid=2063270&tool=pmcentrez&rendertype=abstract 66. Ellem, K. A. O., Rourke, M. G. E. O., Johnson, G. R., Parry, G., Misko, I. S., Schmidt, C. W., . . . Mulligan, R. C. (1997). A case report: immune responses and clinical course of the first human use of granulocyte/macrophage-colony-stimulating-factor-transduced autologous melanoma. *Cancer Immunology, Immunotherapy*, 10-20. Retrieved from http://www.springerlink.com/index/JQ4EB21E4C7ADMT7.pdf 67. Gast, G. de, & Klümpen, H. (2000). immunotherapy with subcutaneous granulocyte macrophage colony-stimulating factor, low-dose interleukin 2, and interferon Î± in progressive metastatic melanoma. *Clinical Cancer Research*. Retrieved from http://clincancerres.aacrjournals.org/content/6/4/1267. short 68. Hill, H., Jr, T. C., & Sabel, M. (2002). Immunotherapy with Interleukin 12 and Granulocyte-Macrophage Colony-stimulating Factor-encapsulated Microspheres Coinduction of Innate and Adaptive Antitumor. *Cancer Research*. Retrieved from http://cancerres.aacrjournals.org/content/62/24/7254.short 69. Lokshin, A., Mayotte, J., & Levitt, M. (1995). Mechanism of Interferon Beta-Induced Squamous Differentiation and Programmed Cell Death in Human Non-Small-Cell Lung Cancer Cell Lines. *Journal of the National Cancer Institute*, 87, 206-212. Retrieved from http://jnci.oxfordjournals.org/content/87/3/206.short 70. Johns, T., & Mackay, I. (1992). Antiproliferative potencies of interferons on melanoma cell lines and xenografts: higher efficacy of interferon Î². *Journal of the National Cancer Institute*, (type II), 1185-1190. Retrieved from http://jncioxfordjournals.org/content/84/15/1185

71. Qin, X.-Q., Runkel, L., Deck, C., DeDios, C., & Barsoum, J. (1997). Interferon-beta induces S phase accumulation selectively in human transformed cells. *Journal of Interferon & Cytokine Research*, 17(6), 355-367. http://doi.org/10.1089/jir.1997.17.355

72. Zhang, F., Lu, W., & Dong, Z. (2002). Tumor-infiltrating macrophages are involved in suppressing growth and metastasis of human prostate cancer cells by INF-β gene therapy in nude mice. *Clinical Cancer Research*, 2942-2951. Retrieved from http://clincancerres.aacrjournals.org/content/8/9/2942. short 73. Simpson, K. D., Templeton, D. J., & Cross, J. V. (2012). Macrophage Migration Inhibitory Factor Promotes Tumor Growth and Metastasis by Inducing Myeloid-Derived Suppressor Cells in the Tumor Microenvironment. *The Journal of Immunology*. http://doi org/10.4049/jimmunol.1201161

74. Sanford, D. E., Belt, B. A., Panni, R. Z., Mayer, A., Deshpande, A. D., Carpenter, D., . . . Linehan, D. C. (2013). Inflammatory monocyte mobilization decreases patient survival in pancreatic cancer: a role for targeting the CCL2/CCR2 axis. *Clinical Cancer Research: An Official Journal of the American Association for Cancer Research*, 19(13), 3404-15. http://doi.org/10.1158/1078-0432.CCR-13-0525

75. Schmall, A., Al-Tamari, H. M., Herold, S., Kampschulte, M., Weigert, A., Wietelmann, A., . . . Savai, R. (2014). Macrophage and Cancer Cell Crosstalk via CCR2 and CX3CR1 is a Fundamental Mechanism Driving Lung Cancer. *American Journal of Respiratory and Critical Care Medicine*. http://doi.org/10.1164/rccm 0.201406-1137OC 76. Kimura, Y. N., Watari, K., Fotovati, A., Hosoi, F., Yasumoto, K., Izumi, H., . . . Ono, M. (2007). Inflammatory stimuli from macrophages and cancer cells synergistically promote tumor growth and angiogenesis. *Cancer Science*, 98(12), 2009-18. http://doi.org/10.1111/j.1349-7006.2007.00633.x 77. Chen, H., Li, P., Yin, Y., Cai, X., Huang, Z., Chen, J., . . . Zhang, J. (2010). The promotion of type 1 T helper cell responses to cationic polymers in vivo via toll-like receptor-4 mediated IL-12 secretion. *Biomaterials*, 31(32), 8172-80. http://doi.org/10.1016/j.biomaterials.2010.07.056

78. Rogers, T. L., & Holen, I. (2011). Tumour macrophages as potential targets of bisphosphonates. *Journal of Translational Medicine*, 9(1), 177. http://doi.org/10.1186/1479-5876-9-177

79. Junankar, S., Shay, G., Jurczyluk, J., Ali, N., Down, J., Pocock, N., . . . Rogers, M. J. (2015). Real-time intravital imaging establishes tumor-associated macrophages as the extraskeletal target of bisphosphonate action in cancer. *Cancer Discovery*, 5(1), 35-42. http://doi.org/10.1158/2159-8290.CD-14-0621

80. Huang, Z., Yang, Y., Jiang, Y., Shao, J., Sun, X., Chen, J., . . . Zhang, J. (2013). Anti-tumor immune responses of tumor-associated macrophages via toll-like receptor 4 triggered by cationic polymers. *Biomaterials*, 34(3), 746-55. http://doi.org/10.1016/j.biomaterials.2012.09.062

81. Q. He, T. Fornander, H. Johansson et al., "Thymidine kinase 1 in serum predicts increased risk of distant or loco-regional recurrence following surgery in patients with early breast cancer," *Anticancer Research*, vol. 26, no. 6, pp. 4753-4759, 2006.

82. K., L. O'Neill, M. Hoper, and G. W. Odling-Smee, "Can thymidine kinase levels in breast tumors predict disease recurrence?" Journal of the National Cancer Institute, vol. 84, no. 23, pp. 1825-1828, 1992.

What is claimed is:

1. A method of administering a monocyte or macrophage cell to a subject, the method comprising:
    administering to the subject a monocyte or macrophage cell comprising a plasmid encoding a chimeric receptor;
    wherein the chimeric receptor comprises:
        a cytoplasmic domain;
        a transmembrane domain; and
        an extracellular ligand binding domain;
        wherein the binding of a ligand to the extracellular ligand binding domain activates the cytoplasmic portion; and
        wherein activation of the cytoplasmic portion provides a signal for polarization to an M2 macrophage.

2. The method according to claim 1, wherein the extracellular domain is an antibody or fragment thereof specific for the ligand.

3. The method according to claim 2, wherein the extracellular ligand binding domain comprises a ScFv.

4. The method according to claim 1, wherein the chimeric receptor further comprises a linker between the transmembrane domain and the extracellular ligand binding domain.

5. The method according to claim 4, wherein the linker is a GS linker.

6. The method according to claim 4, wherein the chimeric receptor further comprises a hinge region between the transmembrane domain and the linker.

7. The method according to claim 1, wherein the chimeric receptor further comprises a hinge region between the transmembrane domain and the extracellular ligand binding domain.

8. The method according to claim 1, wherein the cell was isolated from the subject.

9. The method according to claim 1, wherein the subject is suffering from inflammation or an autoimmune disorder.

10. The method according to claim 1, wherein administration of the cell to the subject decreases an immune response, promotes tissue repair, and/or promotes angiogenesis in the subject.

11. The method according to claim 1, wherein administration of the cell reduces inflammation in the subject.

12. The method according to claim 1, wherein administration of the cell suppresses T cell responses in the subject.

* * * * *

SEQUENCE LISTING

<160> NUMBER OF SEQ ID NOS: 54

<210> SEQ ID NO 1
<211> LENGTH: 904
<212> TYPE: PRT
<213> ORGANISM: Homo sapiens

<400> SEQUENCE: 1

```
Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
```

```
                    245                 250                 255
Asn Ser Gln Leu Ser Thr Thr Ser Asn Thr Thr Phe Leu Gly Leu Lys
            260                 265                 270
Trp Thr Asn Leu Thr Met Leu Asp Leu Ser Tyr Asn Leu Asn Val
        275                 280                 285
Val Gly Asn Asp Ser Phe Ala Trp Leu Pro Gln Leu Glu Tyr Phe Phe
    290                 295                 300
Leu Glu Tyr Asn Ile Gln His Leu Phe Ser His Ser Leu His Gly
305                 310                 315                 320
Leu Phe Asn Val Arg Tyr Leu Asn Leu Lys Arg Ser Phe Thr Lys Gln
            325                 330                 335
Ser Ile Ser Leu Ala Ser Leu Pro Lys Ile Asp Asp Phe Ser Phe Gln
        340                 345                 350
Trp Leu Lys Cys Leu Glu His Leu Asn Met Glu Asp Asn Asp Ile Pro
    355                 360                 365
Gly Ile Lys Ser Asn Met Phe Thr Gly Leu Ile Asn Leu Lys Tyr Leu
    370                 375                 380
Ser Leu Ser Asn Ser Phe Thr Ser Leu Arg Thr Leu Thr Asn Glu Thr
385                 390                 395                 400
Phe Val Ser Leu Ala His Ser Pro Leu His Ile Leu Asn Leu Thr Lys
            405                 410                 415
Asn Lys Ile Ser Lys Ile Glu Ser Asp Ala Phe Ser Trp Leu Gly His
        420                 425                 430
Leu Glu Val Leu Asp Leu Gly Leu Asn Glu Ile Gly Gln Glu Leu Thr
    435                 440                 445
Gly Gln Glu Trp Arg Gly Leu Glu Asn Ile Phe Glu Ile Tyr Leu Ser
    450                 455                 460
Tyr Asn Lys Tyr Leu Gln Leu Thr Arg Asn Ser Phe Ala Leu Val Pro
465                 470                 475                 480
Ser Leu Gln Arg Leu Met Leu Arg Arg Val Ala Leu Lys Asn Val Asp
            485                 490                 495
Ser Ser Pro Ser Pro Phe Gln Pro Leu Arg Asn Leu Thr Ile Leu Asp
        500                 505                 510
Leu Ser Asn Asn Asn Ile Ala Asn Ile Asn Asp Asp Met Leu Glu Gly
    515                 520                 525
Leu Glu Lys Leu Glu Ile Leu Asp Leu Gln His Asn Asn Leu Ala Arg
    530                 535                 540
Leu Trp Lys His Ala Asn Pro Gly Gly Pro Ile Tyr Phe Leu Lys Gly
545                 550                 555                 560
Leu Ser His Leu His Ile Leu Asn Leu Glu Ser Asn Gly Phe Asp Glu
            565                 570                 575
Ile Pro Val Glu Val Phe Lys Asp Leu Phe Glu Leu Lys Ile Ile Asp
        580                 585                 590
Leu Gly Leu Asn Asn Leu Asn Thr Leu Pro Ala Ser Val Phe Asn Asn
    595                 600                 605
Gln Val Ser Leu Lys Ser Leu Asn Leu Gln Lys Asn Leu Ile Thr Ser
    610                 615                 620
Val Glu Lys Lys Val Phe Gly Pro Ala Phe Arg Asn Leu Thr Glu Leu
625                 630                 635                 640
Asp Met Arg Phe Asn Pro Phe Asp Cys Thr Cys Glu Ser Ile Ala Trp
            645                 650                 655
Phe Val Asn Trp Ile Asn Glu Thr His Thr Asn Ile Pro Glu Leu Ser
        660                 665                 670
```

Ser His Tyr Leu Cys Asn Thr Pro Pro His Tyr His Gly Phe Pro Val
            675                 680                 685

Arg Leu Phe Asp Thr Ser Ser Cys Lys Asp Ser Ala Pro Phe Glu Leu
        690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
        755                 760                 765

Trp Val Trp Glu His Phe Ser Ser Met Glu Lys Glu Asp Gln Ser Leu
770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Val Phe Leu Glu Glu Ile Pro Asp Tyr Lys Leu Asn His Ala Leu
850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900

<210> SEQ ID NO 2
<211> LENGTH: 2715
<212> TYPE: DNA
<213> ORGANISM: Homo sapiens

<400> SEQUENCE: 2
atgagacaga ctttgccttg tatctacttt tggggggggcc ttttgcccctt tgggatgctg      60 tgtgcatcct ccaccaccaa gtgcactgtt agccatgaag ttgctgactg cagccacctg     120
aagttgactc aggtacccga tgatctaccc acaaacataa cagtgttgaa ccttacccat     180
aatcaactca agagattacc agccgccaac ttcacaaggt atagccagct aactagcttg     240
gatgtaggat taacaccat ctcaaaactg gagccagaat tgtgccagaa acttcccatg     300
ttaaaagttt tgaacctcca gcacaatgag ctatctcaac tttctgataa aaccttgcc      360 ttctgcacga atttgactga actccatctc atgtccaact caatccagaa aattaaaaat     420
aatccctttg tcaagcagaa gaatttaatc acattagatc tgtctcataa tggcttgtca     480
tctacaaaat taggaactca ggttcagctg gaaaatctcc aagagcttct attatcaaac     540
aataaaattc aagcgctaaa aagtgaagaa ctggatatct tgccaattc atctttaaaa      600 aaattagagt tgtcatcgaa tcaaattaaa gagttttctc agggtgttt tcacgcaatt      660 ggaagattat ttggcctctt tctgaacaat gtccagctgg gtcccagcct acagagaag      720 ctatgtttgg aattagcaaa cacaagcatt cggaatctgt ctctgagtaa cagccagctg     780

-continued

```
tccaccacca gcaatacaac tttcttggga ctaaagtgga caaatctcac tatgctcgat      840
cttcctaca acaacttaaa tgtggttggt aacgattcct ttgcttggct tccacaacta       900
gaatatttct tcctagagta taataatata cagcatttgt tttctcactc tttgcacggg      960
cttttcaatg tgaggtacct gaatttgaaa cggtctttta ctaaacaaag tatttccctt     1020
gcctcactcc ccaagattga tgattttct tttcagtggc taaaatgttt ggagcacctt      1080
aacatggaag ataatgatat ccaggcata aaaagcaata tgttcacagg attgataaac      1140
ctgaaatact taagtctatc caactccttt acaagtttgc gaactttgac aaatgaaaca    1200
tttgtatcac ttgctcattc tcccttacac atactcaacc taaccaagaa taaaatctca    1260
aaaatagaga gtgatgcttt ctcttggttg ggccacctag aagtacttga cctgggcctt    1320
aatgaaattg gcaagaact cacaggccag gaatggagag gtctagaaaa tattttcgaa    1380
atctatcttt cctacaacaa gtacctgcag ctgactagga actcctttgc cttggtccca   1440
agccttcaac gactgatgct ccgaaggtg gcccttaaaa atgtggatag ctctccttca    1500
ccattccagc ctcttcgtaa cttgaccatt ctggatctaa gcaacaacaa catagccaac   1560
ataaatgatg acatgttgga gggtcttgag aaactagaaa ttctcgattt gcagcataac   1620
aacttagcac ggctctggaa acacgcaaac cctggtggtc ccatttattt cctaaagggt   1680
ctgtctcacc tccacatcct taacttggag tccaacggct ttgacgagat cccagttgag   1740
gtcttcaagg atttattga actaaagatc atcgatttag gattgaataa tttaaacaca    1800
cttccagcat ctgtctttaa taatcaggtg tctctaaagt cattgaacct tcagaagaat   1860
ctcataacat ccgttgagaa aaggttttc gggccagctt tcaggaaacct gactgagtta   1920
gatatgcgct ttaatccctt tgattgcacg tgtgaaagta ttgcctggtt tgttaattgg   1980
attaacgaga cccataccaa catccctgag ctgtcaagcc actaccttg caacactcca    2040
cctcactatc atgggttccc agtgagactt tttgatacat catcttgcaa agacagtgcc   2100
ccctttgaac tcttttcat gatcaatacc agtatcctgt tgatttttat ctttattgta    2160
cttctcatcc actttgaggg ctggaggata tcttttttatt ggaatgtttc agtcatcga   2220
gttcttggtt tcaaagaaat agacagacag acagaacagt tgaatatgc agcatatata    2280
attcatgcct ataaagataa ggattgggtc tgggaacatt tctcttcaat ggaaaaggaa   2340
gaccaatctc tcaaatttg tctggaagaa agggactttg aggcgggtgt ttttgaacta   2400
gaagcaattg ttaacagcat caaaagaagc agaaaaatta ttttgttat aacacaccat    2460
ctattaaaag acccattatg caaagattc aaggtacatc atgcagttca acaagctatt    2520
gaacaaaatc tggattccat tatattggtt ttccttgagg agattccaga ttataaactg   2580
aaccatgcac tctgtttgcg aagaggaatg tttaaatctc actgcatctt gaactggcca   2640
gttcagaaag aacggatagg tgcctttcgt cataaattgc aagtagcact tggatccaaa   2700
aactctgtac attaa                                                     2715
```

<210> SEQ ID NO 3
<211> LENGTH: 839
<212> TYPE: PRT
<213> ORGANISM: Homo sapiens

<400> SEQUENCE: 3

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val

```
                     20                  25                  30
        Val Pro Asn Ile Thr Tyr Gln Cys Met Glu Leu Asn Phe Tyr Lys Ile
                     35                  40                  45
        Pro Asp Asn Leu Pro Phe Ser Thr Lys Asn Leu Asp Leu Ser Phe Asn
                     50                  55                  60
        Pro Leu Arg His Leu Gly Ser Tyr Ser Phe Phe Ser Phe Pro Glu Leu
        65                  70                  75                  80
        Gln Val Leu Asp Leu Ser Arg Cys Glu Ile Gln Thr Ile Glu Asp Gly
                            85                  90                  95
        Ala Tyr Gln Ser Leu Ser His Leu Ser Thr Leu Ile Leu Thr Gly Asn
                        100                 105                 110
        Pro Ile Gln Ser Leu Ala Leu Gly Ala Phe Ser Gly Leu Ser Ser Leu
                        115                 120                 125
        Gln Lys Leu Val Ala Val Glu Thr Asn Leu Ala Ser Leu Glu Asn Phe
                    130                 135                 140
        Pro Ile Gly His Leu Lys Thr Leu Lys Glu Leu Asn Val Ala His Asn
        145                 150                 155                 160
        Leu Ile Gln Ser Phe Lys Leu Pro Glu Tyr Phe Ser Asn Leu Thr Asn
                            165                 170                 175
        Leu Glu His Leu Asp Leu Ser Ser Asn Lys Ile Gln Ser Ile Tyr Cys
                        180                 185                 190
        Thr Asp Leu Arg Val Leu His Gln Met Pro Leu Leu Asn Leu Ser Leu
                    195                 200                 205
        Asp Leu Ser Leu Asn Pro Met Asn Phe Ile Gln Pro Gly Ala Phe Lys
                210                 215                 220
        Glu Ile Arg Leu His Lys Leu Thr Leu Arg Asn Asn Phe Asp Ser Leu
        225                 230                 235                 240
        Asn Val Met Lys Thr Cys Ile Gln Gly Leu Ala Gly Leu Glu Val His
                            245                 250                 255
        Arg Leu Val Leu Gly Glu Phe Arg Asn Glu Gly Asn Leu Glu Lys Phe
                        260                 265                 270
        Asp Lys Ser Ala Leu Glu Gly Leu Cys Asn Leu Thr Ile Glu Glu Phe
                    275                 280                 285
        Arg Leu Ala Tyr Leu Asp Tyr Tyr Leu Asp Asp Ile Ile Asp Leu Phe
                290                 295                 300
        Asn Cys Leu Thr Asn Val Ser Ser Phe Ser Leu Val Ser Val Thr Ile
        305                 310                 315                 320
        Glu Arg Val Lys Asp Phe Ser Tyr Asn Phe Gly Trp Gln His Leu Glu
                            325                 330                 335
        Leu Val Asn Cys Lys Phe Gly Gln Phe Pro Thr Leu Lys Leu Lys Ser
                        340                 345                 350
        Leu Lys Arg Leu Thr Phe Thr Ser Asn Lys Gly Gly Asn Ala Phe Ser
                    355                 360                 365
        Glu Val Asp Leu Pro Ser Leu Glu Phe Leu Asp Leu Ser Arg Asn Gly
                370                 375                 380
        Leu Ser Phe Lys Gly Cys Cys Ser Gln Ser Asp Phe Gly Thr Thr Ser
        385                 390                 395                 400
        Leu Lys Tyr Leu Asp Leu Ser Phe Asn Gly Val Ile Thr Met Ser Ser
                            405                 410                 415
        Asn Phe Leu Gly Leu Glu Gln Leu Glu His Leu Asp Phe Gln His Ser
                        420                 425                 430
        Asn Leu Lys Gln Met Ser Glu Phe Ser Val Phe Leu Ser Leu Arg Asn
                    435                 440                 445
```

Leu Ile Tyr Leu Asp Ile Ser His Thr His Thr Arg Val Ala Phe Asn
450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                485                 490                 495

Asn Leu Thr Phe Leu Asp Leu Ser Gln Cys Gln Leu Glu Gln Leu Ser
                500                 505                 510

Pro Thr Ala Phe Asn Ser Leu Ser Ser Leu Gln Val Leu Asn Met Ser
                515                 520                 525

His Asn Asn Phe Phe Ser Leu Asp Thr Phe Pro Tyr Lys Cys Leu Asn
530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
                580                 585                 590

Trp Ile Lys Asp Gln Arg Gln Leu Leu Val Glu Val Glu Arg Met Glu
595                 600                 605

Cys Ala Thr Pro Ser Asp Lys Gln Gly Met Pro Val Leu Ser Leu Asn
610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
                660                 665                 670

Ile Tyr Asp Ala Phe Val Ile Tyr Ser Ser Gln Asp Glu Asp Trp Val
                675                 680                 685

Arg Asn Glu Leu Val Lys Asn Leu Glu Glu Gly Val Pro Pro Phe Gln
690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
                740                 745                 750

Ile Ala Gln Thr Trp Gln Phe Leu Ser Ser Arg Ala Gly Ile Ile Phe
                755                 760                 765

Ile Val Leu Gln Lys Val Glu Lys Thr Leu Leu Arg Gln Gln Val Glu
770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
                820                 825                 830

Trp Gln Glu Ala Thr Ser Ile
                835

<210> SEQ ID NO 4
<211> LENGTH: 23

```
<212> TYPE: PRT
<213> ORGANISM: Homo sapiens

<400> SEQUENCE: 4

Ile Gly Val Ser Val Leu Ser Val Leu Val Ser Val Val Ala Val
1               5                   10                  15

Leu Val Tyr Lys Phe Tyr Phe
            20

<210> SEQ ID NO 5
<211> LENGTH: 183
<212> TYPE: PRT
<213> ORGANISM: Homo sapiens

<400> SEQUENCE: 5

His Leu Met Leu Leu Ala Gly Cys Ile Lys Tyr Gly Arg Gly Glu Asn
1               5                   10                  15

Ile Tyr Asp Ala Phe Val Ile Tyr Ser Ser Gln Asp Glu Asp Trp Val
            20                  25                  30

Arg Asn Glu Leu Val Lys Asn Leu Glu Glu Gly Val Pro Pro Phe Gln
        35                  40                  45

Leu Cys Leu His Tyr Arg Asp Phe Ile Pro Gly Val Ala Ile Ala Ala
    50                  55                  60

Asn Ile Ile His Glu Gly Phe His Lys Ser Arg Lys Val Ile Val Val
65                  70                  75                  80

Val Ser Gln His Phe Ile Gln Ser Arg Trp Cys Ile Phe Glu Tyr Glu
                85                  90                  95

Ile Ala Gln Thr Trp Gln Phe Leu Ser Ser Arg Ala Gly Ile Ile Phe
            100                 105                 110

Ile Val Leu Gln Lys Val Glu Lys Thr Leu Leu Arg Gln Gln Val Glu
        115                 120                 125

Leu Tyr Arg Leu Leu Ser Arg Asn Thr Tyr Leu Glu Trp Glu Asp Ser
    130                 135                 140

Val Leu Gly Arg His Ile Phe Trp Arg Arg Leu Arg Lys Ala Leu Leu
145                 150                 155                 160

Asp Gly Lys Ser Trp Asn Pro Glu Gly Thr Val Gly Thr Gly Cys Asn
                165                 170                 175

Trp Gln Glu Ala Thr Ser Ile
            180

<210> SEQ ID NO 6
<211> LENGTH: 2520
<212> TYPE: DNA
<213> ORGANISM: Homo sapiens

<400> SEQUENCE: 6
atgatgtctg cctcgcgcct ggctgggact ctgatcccag ccatggcctt cctctcctgc      60
gtgagaccag aaagctggga gccctgcgtg gaggtggttc ctaatattac ttatcaatgc     120
atggagctga atttctacaa aatccccgac aacctcccct tctcaaccaa gaacctggac     180
ctgagctttt atcccctgag gcatttaggc agctatagct tcttcagttt cccagaactg     240
caggtgctga tttatccag gtgtgaaatc cagacaattg aagatggggc atatcagagc     300
ctaagccacc tctctacctt aatattgaca ggaaacccca tccagagttt agccctggga     360 gcctttctg actatcaag tttacagaag ctggtggctg tggagacaaa tctagcatct     420
ctagagaact tccccattgg acatctcaaa actttgaaag aacttaatgt ggctcacaat     480
```

| | | |
|---|---|---|
| cttatccaat ctttcaaatt acctgagtat ttttctaatc tgaccaatct agagcacttg | 540 | |
| gacctttcca gcaacaagat tcaaagtatt tattgcacag acttgcgggt tctacatcaa | 600 | |
| atgcccctac tcaatctctc tttagacctg tccctgaacc ctatgaactt tatccaacca | 660 | |
| ggtgcattta agaaaattag gcttcataag ctgactttaa gaataatttt tgatagttta | 720 | |
| aatgtaatga aaacttgtat tcaaggtctg gctggtttag aagtccatcg tttggttctg | 780 | |
| ggagaattta gaaatgaagg aaacttggaa aagtttgaca atctgctct agagggcctg | 840 | |
| tgcaatttga ccattgaaga attccgatta gcatacttag actactacct cgatgatatt | 900 | |
| attgacttat ttaattgttt gacaaatgtt tcttcatttt ccctggtgag tgtgactatt | 960 | |
| gaaagggtaa aagactttc ttataatttc ggatggcaac atttagaatt agttaactgt | 1020 | |
| aaatttggac agtttcccac attgaaactc aaatctctca aaaggcttac tttcacttcc | 1080 | |
| aacaaaggtg ggaatgcttt ttcagaagtt gatctaccaa gccttgagtt tctagatctc | 1140 | |
| agtagaaatg gcttgagttt caaaggttgc tgttctcaaa gtgattttgg gacaaccagc | 1200 | |
| ctaaagtatt tagatctgag cttcaatggt gttattacca tgagttcaaa cttcttgggc | 1260 | |
| ttagaacaac tagaacatct ggatttccag cattccaatt tgaaacaaat gagtgagttt | 1320 | |
| tcagtattcc tatcactcag aaacctcatt taccttgaca tttctcatac tcacaccaga | 1380 | |
| gttgcttca atggcatctt caatggcttg tccagtctcg aagtcttgaa atggctggc | 1440 | |
| aattctttcc aggaaaactt ccttccagat atcttcacag agctgagaaa cttgaccttc | 1500 | |
| ctggacctct ctcagtgtca actggagcag ttgtctccaa cagcatttaa ctcactctcc | 1560 | |
| agtcttcagg tactaaatat gagccacaac aacttctttt cattggatac gtttccttat | 1620 | |
| aagtgtctga actccctcca ggttcttgat tacagtctca atcacataat gacttccaaa | 1680 | |
| aaacaggaac tacagcattt tccaagtagt ctagctttct taaatcttac tcagaatgac | 1740 | |
| tttgcttgta cttgtgaaca ccagagtttc ctgcaatgga tcaaggacca gaggcagctc | 1800 | |
| ttggtggaag ttgaacgaat ggaatgtgca acaccttcag ataagcaggg catgcctgtg | 1860 | |
| ctgagtttga atatcacctg tcagatgaat aagaccatca ttggtgtgtc ggtcctcagt | 1920 | |
| gtgcttgtag tatctgttgt agcagttctg gtctataagt tctatttca cctgatgctt | 1980 | |
| cttgctggct gcataaagta tggtagaggt gaaaacatct atgatgcctt tgttatctac | 2040 | |
| tcaagccagg atgaggactg ggtaaggaat gagctagtaa agaatttaga agaaggggtg | 2100 | |
| cctccatttc agctctgcct tcactacaga gactttattc ccggtgtggc cattgctgcc | 2160 | |
| aacatcatcc atgaaggttt ccataaaagc cgaaaggtga ttgttgtggt gtcccagcac | 2220 | |
| ttcatccaga gccgctggtg tatctttgaa tatgagattg ctcagacctg gcagtttctg | 2280 | |
| agcagtcgtg ctggtatcat cttcattgtc ctgcagaagg tggagaagac cctgctcagg | 2340 | |
| cagcaggtgg agctgtaccg ccttctcagc aggaacactt acctggagtg ggaggacagt | 2400 | |
| gtcctggggc ggcacatctt ctggagacga ctcagaaaag ccctgctgga tggtaaatca | 2460 | |
| tggaatccag aaggaacagt gggtacagga tgcaattggc aggaagcaac atctatctga | 2520 | |

<210> SEQ ID NO 7
<211> LENGTH: 1049
<212> TYPE: PRT
<213> ORGANISM: Homo sapiens

<400> SEQUENCE: 7

Met Val Phe Pro Met Trp Thr Leu Lys Arg Gln Ile Leu Ile Leu Phe
1               5                   10                  15

```
Asn Ile Ile Leu Ile Ser Lys Leu Leu Gly Ala Arg Trp Phe Pro Lys
             20                  25                  30
Thr Leu Pro Cys Asp Val Thr Leu Asp Val Pro Lys Asn His Val Ile
             35                  40                  45
Val Asp Cys Thr Asp Lys His Leu Thr Glu Ile Pro Gly Gly Ile Pro
 50                  55                  60
Thr Asn Thr Thr Asn Leu Thr Leu Thr Ile Asn His Ile Pro Asp Ile
 65                  70                  75                  80
Ser Pro Ala Ser Phe His Arg Leu Asp His Leu Val Glu Ile Asp Phe
             85                  90                  95
Arg Cys Asn Cys Val Pro Ile Pro Leu Gly Ser Lys Asn Asn Met Cys
            100                 105                 110
Ile Lys Arg Leu Gln Ile Lys Pro Arg Ser Phe Ser Gly Leu Thr Tyr
            115                 120                 125
Leu Lys Ser Leu Tyr Leu Asp Gly Asn Gln Leu Leu Glu Ile Pro Gln
            130                 135                 140
Gly Leu Pro Pro Ser Leu Gln Leu Leu Ser Leu Glu Ala Asn Asn Ile
145                 150                 155                 160
Phe Ser Ile Arg Lys Glu Asn Leu Thr Glu Leu Ala Asn Ile Glu Ile
            165                 170                 175
Leu Tyr Leu Gly Gln Asn Cys Tyr Tyr Arg Asn Pro Cys Tyr Val Ser
            180                 185                 190
Tyr Ser Ile Glu Lys Asp Ala Phe Leu Asn Leu Thr Lys Leu Lys Val
            195                 200                 205
Leu Ser Leu Lys Asp Asn Asn Val Thr Ala Val Pro Thr Val Leu Pro
            210                 215                 220
Ser Thr Leu Thr Glu Leu Tyr Leu Tyr Asn Asn Met Ile Ala Lys Ile
225                 230                 235                 240
Gln Glu Asp Asp Phe Asn Asn Leu Asn Gln Leu Gln Ile Leu Asp Leu
            245                 250                 255
Ser Gly Asn Cys Pro Arg Cys Tyr Asn Ala Pro Phe Pro Cys Ala Pro
            260                 265                 270
Cys Lys Asn Asn Ser Pro Leu Gln Ile Pro Val Asn Ala Phe Asp Ala
            275                 280                 285
Leu Thr Glu Leu Lys Val Leu Arg Leu His Ser Asn Ser Leu Gln His
            290                 295                 300
Val Pro Pro Arg Trp Phe Lys Asn Ile Asn Lys Leu Gln Glu Leu Asp
305                 310                 315                 320
Leu Ser Gln Asn Phe Leu Ala Lys Glu Ile Gly Asp Ala Lys Phe Leu
            325                 330                 335
His Phe Leu Pro Ser Leu Ile Gln Leu Asp Leu Ser Phe Asn Phe Glu
            340                 345                 350
Leu Gln Val Tyr Arg Ala Ser Met Asn Leu Ser Gln Ala Phe Ser Ser
            355                 360                 365
Leu Lys Ser Leu Lys Ile Leu Arg Ile Arg Gly Tyr Val Phe Lys Glu
            370                 375                 380
Leu Lys Ser Phe Asn Leu Ser Pro Leu His Asn Leu Gln Asn Leu Glu
385                 390                 395                 400
Val Leu Asp Leu Gly Thr Asn Phe Ile Lys Ile Ala Asn Leu Ser Met
            405                 410                 415
Phe Lys Gln Phe Lys Arg Leu Lys Val Ile Asp Leu Ser Val Asn Lys
            420                 425                 430
Ile Ser Pro Ser Gly Asp Ser Ser Glu Val Gly Phe Cys Ser Asn Ala
```

-continued

```
            435                 440                 445
Arg Thr Ser Val Glu Ser Tyr Glu Pro Gln Val Leu Glu Gln Leu His
450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                    485                 490                 495

Thr Leu Asp Leu Ser Lys Asn Ser Ile Phe Phe Val Lys Ser Ser Asp
                500                 505                 510

Phe Gln His Leu Ser Phe Leu Lys Cys Leu Asn Leu Ser Gly Asn Leu
            515                 520                 525

Ile Ser Gln Thr Leu Asn Gly Ser Glu Phe Gln Pro Leu Ala Glu Leu
        530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
                580                 585                 590

Lys Asn Leu Lys Val Leu Gln Lys Leu Met Met Asn Asp Asn Asp Ile
            595                 600                 605

Ser Ser Ser Thr Ser Arg Thr Met Glu Ser Glu Ser Leu Arg Thr Leu
        610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
                645                 650                 655

Ile Ser Lys Asn Ser Leu Ser Phe Leu Pro Ser Gly Val Phe Asp Gly
                660                 665                 670

Met Pro Pro Asn Leu Lys Asn Leu Ser Leu Ala Lys Asn Gly Leu Lys
            675                 680                 685

Ser Phe Ser Trp Lys Lys Leu Gln Cys Leu Lys Asn Leu Glu Thr Leu
        690                 695                 700

Asp Leu Ser His Asn Gln Leu Thr Thr Val Pro Glu Arg Leu Ser Asn
705                 710                 715                 720

Cys Ser Arg Ser Leu Lys Asn Leu Ile Leu Lys Asn Asn Gln Ile Arg
                725                 730                 735

Ser Leu Thr Lys Tyr Phe Leu Gln Asp Ala Phe Gln Leu Arg Tyr Leu
                740                 745                 750

Asp Leu Ser Ser Asn Lys Ile Gln Met Ile Gln Lys Thr Ser Phe Pro
            755                 760                 765

Glu Asn Val Leu Asn Asn Leu Lys Met Leu Leu Leu His His Asn Arg
        770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
                820                 825                 830

Cys Glu Leu Asp Leu Thr Asn Leu Ile Leu Phe Ser Leu Ser Ile Ser
            835                 840                 845

Val Ser Leu Phe Leu Met Val Met Met Thr Ala Ser His Leu Tyr Phe
        850                 855                 860
```

```
Trp Asp Val Trp Tyr Ile Tyr His Phe Cys Lys Ala Lys Ile Lys Gly
865                 870                 875                 880
Tyr Gln Arg Leu Ile Ser Pro Asp Cys Cys Tyr Asp Ala Phe Ile Val
                885                 890                 895
Tyr Asp Thr Lys Asp Pro Ala Val Thr Glu Trp Val Leu Ala Glu Leu
            900                 905                 910
Val Ala Lys Leu Glu Asp Pro Arg Glu Lys His Phe Asn Leu Cys Leu
        915                 920                 925
Glu Glu Arg Asp Trp Leu Pro Gly Gln Pro Val Leu Glu Asn Leu Ser
    930                 935                 940
Gln Ser Ile Gln Leu Ser Lys Lys Thr Val Phe Val Met Thr Asp Lys
945                 950                 955                 960
Tyr Ala Lys Thr Glu Asn Phe Lys Ile Ala Phe Tyr Leu Ser His Gln
                965                 970                 975
Arg Leu Met Asp Glu Lys Val Asp Val Ile Leu Ile Phe Leu Glu
            980                 985                 990
Lys Pro Phe Gln Lys Ser Lys Phe  Leu Gln Leu Arg Lys  Arg Leu Cys
        995                 1000                1005
Gly Ser  Ser Val Leu Glu Trp  Pro Thr Asn Pro Gln  Ala His Pro
    1010                1015                1020
Tyr Phe  Trp Gln Cys Leu Lys  Asn Ala Leu Ala Thr  Asp Asn His
    1025                1030                1035
Val Ala  Tyr Ser Gln Val Phe  Lys Glu Thr Val
    1040                1045

<210> SEQ ID NO 8
<211> LENGTH: 3150
<212> TYPE: DNA
<213> ORGANISM: Homo sapiens

<400> SEQUENCE: 8
atggtgtttc caatgtggac actgaagaga caaattctta tccttttttaa cataatccta      60 atttccaaac tccttggggc tagatggttt cctaaaactc tgccctgtga tgtcactctg     120
gatgttccaa agaaccatgt gatcgtggac tgcacagaca agcatttgac agaaattcct     180
ggaggtattc ccacgaacac cacgaacctc accctcacca ttaaccacat accagacatc     240
tccccagcgt cctttcacag actggaccat ctggtagaga tcgatttcag atgcaactgt     300
gtacctattc cactggggtc aaaaaacaac atgtgcatca gaggctgca gattaaaccc      360 agaagcttta gtggactcac ttatttaaaa tcccttttacc tggatggaaa ccagctacta     420
gagataccgc agggcctccc gcctagctta cagcttctca gccttgaggc aacaacatc      480 ttttccatca gaaagagaa tctaacgaaa ctggccaaca tagaaatact ctacctgggc      540
caaaactgtt attatcgaaa tccttgttat gtttcatatt caatagagaa agatgccttc     600
ctaaacttga caaagttaaa agtgctctcc ctgaaagata caatgtcac agccgtccct      660 actgttttgc catctacttt aacagaacta tatctctaca caacatgat tgcaaaaatc      720 caagaagatg attttaataa cctcaaccaa ttacaaattc ttgacctaag tggaaattgc     780
cctcgttgtt ataatgcccc atttccttgt gcgccgtgta aaaataattc ccctacag       840 atccctgtaa atgcttttga tgcgctgaca gaattaaaag ttttacgtct acacagtaac      900
tctcttcagc atgtgccccc aagatggttt aagaacatca acaaactcca ggaactggat      960
ctgtcccaaa acttcttggc caagaaaatt ggggatgcta aatttctgca ttttctcccc    1020
```

```
agcctcatcc aattggatct gtctttcaat tttgaacttc aggtctatcg tgcatctatg    1080
aatctatcac aagcattttc ttcactgaaa agcctgaaaa ttctgcggat cagaggatat    1140
gtctttaaag agttgaaaag ctttaacctc tcgccattac ataatcttca aaatcttgaa    1200
gttcttgatc ttggcactaa ctttataaaa attgctaacc tcagcatgtt taaacaattt    1260
aaaagactga aagtcataga tctttcagtg aataaaatat caccttcagg agattcaagt    1320
gaagttggct tctgctcaaa tgccagaact tctgtagaaa gttatgaacc ccaggtcctg    1380
gaacaattac attatttcag atatgataag tatgcaagga gttgcagatt caaaaacaaa    1440
gaggcttctt tcatgtctgt taatgaaagc tgctacaagt atgggcagac cttggatcta    1500
agtaaaaata gtatatttt tgtcaagtcc tctgattttc agcatctttc tttcctcaaa    1560
tgcctgaatc tgtcaggaaa tctcattagc caaactctta atggcagtga attccaacct    1620
ttagcagagc tgagatattt ggacttctcc aacaaccggc ttgatttact ccattcaaca    1680
gcatttgaag agcttcacaa actggaagtt ctggatataa gcagtaatag ccattatttt    1740
caatcagaag gaattactca tatgctaaac tttaccaaga acctaaaggt tctgcagaaa    1800
ctgatgatga acgacaatga catctcttcc tccaccagca ggaccatgga gagtgagtct    1860
cttagaactc tggaattcag aggaaatcac ttagatgttt tatggagaga aggtgataac    1920
agatacttac aattattcaa gaatctgcta aaattagagg aattagacat ctctaaaaat    1980
tccctaagtt tcttgccttc tggagttttt gatggtatgc ctccaaatct aaagaatctc    2040
tctttggcca aaaatgggct caaatctttc agttggaaga aactccagtg tctaaagaac    2100
ctggaaactt tggacctcag ccacaaccaa ctgaccactg tccctgagag attatccaac    2160
tgttccagaa gcctcaagaa tctgattctt aagaataatc aaatcaggag tctgacgaag    2220
tattttctac aagatgcctt ccagttgcga tatctggatc tcagctcaaa taaaatccag    2280
atgatccaaa agaccagctt cccagaaaat gtcctcaaca atctgaagat gttgcttttg    2340
catcataatc ggtttctgtg cacctgtgat gctgtgtggt ttgtctggtg ggttaaccat    2400
acggaggtga ctattcctta cctggccaca gatgtgactt gtgtggggcc aggagcacac    2460
aagggccaaa gtgtgatctc cctggatctg tacacctgtg agttagatct gactaacctg    2520
attctgttct cactttccat atctgtatct ctctttctca tggtgatgat gacagcaagt    2580
cacctctatt tctgggatgt gtggtatatt taccatttct gtaaggccaa gataaagggg    2640
tatcagcgtc taatatcacc agactgttgc tatgatgctt ttattgtgta tgacactaaa    2700
gacccagctg tgaccgagtg ggttttggct gagctggtgg ccaaactgga agacccaaga    2760
gagaaacatt ttaatttatg tctcgaggaa agggactggt taccagggca gccagttctg    2820
gaaaaccttt cccagagcat acagcttagc aaaaagacag tgtttgtgat gacagacaag    2880
tatgcaaaga ctgaaaattt taagatagca ttttacttgt cccatcagag gctcatggat    2940 gaaaagttg atgtgattat cttgatattt cttgagaagc cctttcagaa gtccaagttc    3000
ctccagctcc ggaaaaggct ctgtgggagt tctgtccttg agtggccaac aaacccgcaa    3060
gctcacccat acttctggca gtgtctaaag aacgccctgg ccacagacaa tcatgtggcc    3120
tatagtcagg tgttcaagga aacggtctag                                    3150
```

<210> SEQ ID NO 9
<211> LENGTH: 1041
<212> TYPE: PRT
<213> ORGANISM: Homo sapiens

<400> SEQUENCE: 9

-continued

```
Met Glu Asn Met Phe Leu Gln Ser Ser Met Leu Thr Cys Ile Phe Leu
1               5                   10                  15

Leu Ile Ser Gly Ser Cys Glu Leu Cys Ala Glu Asn Phe Ser Arg
            20                  25                  30

Ser Tyr Pro Cys Asp Glu Lys Lys Gln Asn Asp Ser Val Ile Ala Glu
            35                  40                  45

Cys Ser Asn Arg Arg Leu Gln Glu Val Pro Gln Thr Val Gly Lys Tyr
50                  55                  60

Val Thr Glu Leu Asp Leu Ser Asp Asn Phe Ile Thr His Ile Thr Asn
65                  70                  75                  80

Glu Ser Phe Gln Gly Leu Gln Asn Leu Thr Lys Ile Asn Leu Asn His
                85                  90                  95

Asn Pro Asn Val Gln His Gln Asn Gly Asn Pro Gly Ile Gln Ser Asn
                100                 105                 110

Gly Leu Asn Ile Thr Asp Gly Ala Phe Leu Asn Leu Lys Asn Leu Arg
            115                 120                 125

Glu Leu Leu Leu Glu Asp Asn Gln Leu Pro Gln Ile Pro Ser Gly Leu
130                 135                 140

Pro Glu Ser Leu Thr Glu Leu Ser Leu Ile Gln Asn Asn Ile Tyr Asn
145                 150                 155                 160

Ile Thr Lys Glu Gly Ile Ser Arg Leu Ile Asn Leu Lys Asn Leu Tyr
                165                 170                 175

Leu Ala Trp Asn Cys Tyr Phe Asn Lys Val Cys Glu Lys Thr Asn Ile
            180                 185                 190

Glu Asp Gly Val Phe Glu Thr Leu Thr Asn Leu Glu Leu Leu Ser Leu
            195                 200                 205

Ser Phe Asn Ser Leu Ser His Val Pro Pro Lys Leu Pro Ser Ser Leu
210                 215                 220

Arg Lys Leu Phe Leu Ser Asn Thr Gln Ile Lys Tyr Ile Ser Glu Glu
225                 230                 235                 240

Asp Phe Lys Gly Leu Ile Asn Leu Thr Leu Leu Asp Leu Ser Gly Asn
            245                 250                 255

Cys Pro Arg Cys Phe Asn Ala Pro Phe Pro Cys Val Pro Cys Asp Gly
            260                 265                 270

Gly Ala Ser Ile Asn Ile Asp Arg Phe Ala Phe Gln Asn Leu Thr Gln
            275                 280                 285

Leu Arg Tyr Leu Asn Leu Ser Ser Thr Ser Leu Arg Lys Ile Asn Ala
        290                 295                 300

Ala Trp Phe Lys Asn Met Pro His Leu Lys Val Leu Asp Leu Glu Phe
305                 310                 315                 320

Asn Tyr Leu Val Gly Glu Ile Ala Ser Gly Ala Phe Leu Thr Met Leu
            325                 330                 335

Pro Arg Leu Glu Ile Leu Asp Leu Ser Phe Asn Tyr Ile Lys Gly Ser
            340                 345                 350

Tyr Pro Gln His Ile Asn Ile Ser Arg Asn Phe Ser Lys Leu Leu Ser
        355                 360                 365

Leu Arg Ala Leu His Leu Arg Gly Tyr Val Phe Gln Glu Leu Arg Glu
        370                 375                 380

Asp Asp Phe Gln Pro Leu Met Gln Leu Pro Asn Leu Ser Thr Ile Asn
385                 390                 395                 400

Leu Gly Ile Asn Phe Ile Lys Gln Ile Asp Phe Lys Leu Phe Gln Asn
                405                 410                 415
```

```
Phe Ser Asn Leu Glu Ile Ile Tyr Leu Ser Glu Asn Arg Ile Ser Pro
            420                 425                 430

Leu Val Lys Asp Thr Arg Gln Ser Tyr Ala Asn Ser Ser Ser Phe Gln
            435                 440                 445

Arg His Ile Arg Lys Arg Arg Ser Thr Asp Phe Glu Phe Asp Pro His
            450                 455                 460

Ser Asn Phe Tyr His Phe Thr Arg Pro Leu Ile Lys Pro Gln Cys Ala
465                 470                 475                 480

Ala Tyr Gly Lys Ala Leu Asp Leu Ser Leu Asn Ser Ile Phe Phe Ile
                485                 490                 495

Gly Pro Asn Gln Phe Glu Asn Leu Pro Asp Ile Ala Cys Leu Asn Leu
            500                 505                 510

Ser Ala Asn Ser Asn Ala Gln Val Leu Ser Gly Thr Glu Phe Ser Ala
            515                 520                 525

Ile Pro His Val Lys Tyr Leu Asp Leu Thr Asn Asn Arg Leu Asp Phe
            530                 535                 540

Asp Asn Ala Ser Ala Leu Thr Glu Leu Ser Asp Leu Glu Val Leu Asp
545                 550                 555                 560

Leu Ser Tyr Asn Ser His Tyr Phe Arg Ile Ala Gly Val Thr His His
                565                 570                 575

Leu Glu Phe Ile Gln Asn Phe Thr Asn Leu Lys Val Leu Asn Leu Ser
            580                 585                 590

His Asn Asn Ile Tyr Thr Leu Thr Asp Lys Tyr Asn Leu Glu Ser Lys
            595                 600                 605

Ser Leu Val Glu Leu Val Phe Ser Gly Asn Arg Leu Asp Ile Leu Trp
610                 615                 620

Asn Asp Asp Asp Asn Arg Tyr Ile Ser Ile Phe Lys Gly Leu Lys Asn
625                 630                 635                 640

Leu Thr Arg Leu Asp Leu Ser Leu Asn Arg Leu Lys His Ile Pro Asn
                645                 650                 655

Glu Ala Phe Leu Asn Leu Pro Ala Ser Leu Thr Glu Leu His Ile Asn
            660                 665                 670

Asp Asn Met Leu Lys Phe Phe Asn Trp Thr Leu Leu Gln Gln Phe Pro
            675                 680                 685

Arg Leu Glu Leu Leu Asp Leu Arg Gly Asn Lys Leu Leu Phe Leu Thr
            690                 695                 700

Asp Ser Leu Ser Asp Phe Thr Ser Ser Leu Arg Thr Leu Leu Leu Ser
705                 710                 715                 720

His Asn Arg Ile Ser His Leu Pro Ser Gly Phe Leu Ser Glu Val Ser
                725                 730                 735

Ser Leu Lys His Leu Asp Leu Ser Asn Leu Leu Lys Thr Ile Asn
            740                 745                 750

Lys Ser Ala Leu Glu Thr Lys Thr Thr Thr Lys Leu Ser Met Leu Glu
            755                 760                 765

Leu His Gly Asn Pro Phe Glu Cys Thr Cys Asp Ile Gly Asp Phe Arg
            770                 775                 780

Arg Trp Met Asp Glu His Leu Asn Val Lys Ile Pro Arg Leu Val Asp
785                 790                 795                 800

Val Ile Cys Ala Ser Pro Gly Asp Gln Arg Gly Lys Ser Ile Val Ser
                805                 810                 815

Leu Glu Leu Thr Thr Cys Val Ser Asp Val Thr Ala Val Ile Leu Phe
            820                 825                 830

Phe Phe Thr Phe Phe Ile Thr Thr Met Val Met Leu Ala Ala Leu Ala
```

His His Leu Phe Tyr Trp Asp Val Trp Phe Ile Tyr Asn Val Cys Leu
835                 840                 845
            850                 855                 860

Ala Lys Val Lys Gly Tyr Arg Ser Leu Ser Thr Ser Gln Thr Phe Tyr
865                 870                 875                 880

Asp Ala Tyr Ile Ser Tyr Asp Thr Lys Asp Ala Ser Val Thr Asp Trp
                885                 890                 895

Val Ile Asn Glu Leu Arg Tyr His Leu Glu Glu Ser Arg Asp Lys Asn
            900                 905                 910

Val Leu Leu Cys Leu Glu Glu Arg Asp Trp Asp Pro Gly Leu Ala Ile
            915                 920                 925

Ile Asp Asn Leu Met Gln Ser Ile Asn Gln Ser Lys Lys Thr Val Phe
930                 935                 940

Val Leu Thr Lys Lys Tyr Ala Lys Ser Trp Asn Phe Lys Thr Ala Phe
945                 950                 955                 960

Tyr Leu Ala Leu Gln Arg Leu Met Asp Glu Asn Met Asp Val Ile Ile
                965                 970                 975

Phe Ile Leu Leu Glu Pro Val Leu Gln His Ser Gln Tyr Leu Arg Leu
            980                 985                 990

Arg Gln Arg Ile Cys Lys Ser Ser  Ile Leu Gln Trp Pro  Asp Asn Pro
            995                 1000                1005

Lys Ala  Glu Gly Leu Phe Trp  Gln Thr Leu Arg Asn  Val Val Leu
1010                1015                1020

Thr Glu  Asn Asp Ser Arg Tyr  Asn Asn Met Tyr Val  Asp Ser Ile
1025                1030                1035

Lys Gln  Tyr
1040

<210> SEQ ID NO 10
<211> LENGTH: 3126
<212> TYPE: DNA
<213> ORGANISM: Homo sapiens

<400> SEQUENCE: 10

```
atggaaaaca tgttccttca gtcgtcaatg ctgacctgca ttttcctgct aatatctggt      60
tcctgtgagt tatgcgccga agaaaatttt tctagaagct atccttgtga tgagaaaaag     120
caaaatgact cagttattgc agagtgcagc aatcgtcgac tacaggaagt cccccaaacg     180
gtgggcaaat atgtgacaga actagacctg tctgataatt tcatcacaca cataacgaat     240
gaatcatttc aagggctgca aaatctcact aaaataaatc taaaccacaa ccccaatgta     300
cagcaccaga acggaaatcc cggtatacaa tcaaatggct gaatatcac agacggggca     360 ttcctcaacc taaaaaacct aagggagtta ctgcttgaag acaaccagtt accccaaata     420
ccctctggtt tgccagagtc tttgacagaa cttagtctaa ttcaaaacaa tatatacaac     480
ataactaaag agggcatttc aagacttata aacttgaaaa atctctattt ggcctggaac     540
tgctatttta acaaagtttg cgagaaaact aacatagaag atggagtatt tgaaacgctg     600
acaaatttgg agttgctatc actatctttc aattctcttt cacacgtgcc acccaaactg     660
ccaagctccc tacgcaaact ttttctgagc aacacccaga tcaaatacat tagtgaagaa     720
gatttcaagg gattgataaa tttaacatta ctagatttaa gcgggaactg tccgaggtgc     780
ttcaatgccc catttccatg cgtgccttgt gatggtggtg cttcaattaa tatagatcgt     840
tttgcttttc aaaacttgac ccaacttcga tacctaaacc tctctagcac ttccctcagg     900
```

```
aagattaatg ctgcctggtt taaaaatatg cctcatctga aggtgctgga tcttgaattc      960
aactatttag tgggagaaat agcctctggg gcattttttaa cgatgctgcc ccgcttagaa    1020
atacttgact tgtcttttaa ctatataaag gggagttatc cacagcatat taatatttcc    1080
agaaacttct ctaaactttt gtctctacgg gcattgcatt taagaggtta tgtgttccag    1140
gaactcagag aagatgattt ccagcccctg atgcagcttc caaacttatc gactatcaac    1200
ttgggtatta atttttattaa gcaaatcgat ttcaaacttt tccaaaattt ctccaatctg   1260
gaaattattt acttgtcaga aaacagaata tcaccgttgg taaaagatac ccggcagagt   1320
tatgcaaata gttcctcttt tcaacgtcat atccggaaac gacgctcaac agattttgag   1380
tttgacccac attcgaactt ttatcatttc acccgtcctt taataaagcc acaatgtgct    1440
gcttatggaa aagccttaga tttaagcctc aacagtattt tcttcattgg gccaaaccaa   1500
tttgaaaatc ttcctgacat tgcctgttta aatctgtctg caaatagcaa tgctcaagtg   1560
ttaagtggaa ctgaattttc agccattcct catgtcaaat atttggattt gacaaacaat   1620
agactagact ttgataatgc tagtgctctt actgaattgt ccgacttgga agttctagat   1680
ctcagctata attcacacta tttcagaata gcaggcgtaa cacatcatct agaatttatt   1740
caaaatttca caaatctaaa agttttaaac ttgagccaca acaacattta tactttaaca   1800
gataagtata acctggaaag caagtccctg gtagaattag ttttcagtgg caatcgcctt   1860
gacattttgt ggaatgatga tgacaacagg tatatctcca ttttcaaagg tctcaagaat   1920
ctgacacgtc tggatttatc ccttaatagg ctgaagcaca tcccaaatga agcattcctt   1980
aatttgccag cgagtctcac tgaactacat ataaatgata atatgttaaa gttttttaac   2040
tggacattac tccagcagtt tcctcgtctc gagttgcttg acttacgtgg aaacaaacta   2100
ctctttttaa ctgatagcct atctgacttt acatcttccc ttcggacact gctgctgagt   2160
cataacagga tttcccacct accctctggc tttctttctg aagtcagtag tctgaagcac   2220
ctcgatttaa gttccaatct gctaaaaaca atcaacaaat ccgcacttga aactaagacc   2280
accaccaaat tatctatgtt ggaactacac ggaaacccct ttgaatgcac ctgtgacatt   2340
ggagatttcc gaagatggat ggatgaacat ctgaatgtca aaattcccag actggtagat   2400
gtcatttgtg ccagtcctgg ggatcaaaga gggaagagta ttgtgagtct ggagctaaca   2460
acttgtgttt cagatgtcac tgcagtgata ttattttttct tcacgttctt tatcaccacc   2520
atggttatgt tggctgccct ggctcaccat ttgttttact gggatgtttg gtttatatat    2580
aatgtgtgtt tagctaaggt aaaaggctac aggtctcttt ccacatccca aactttctat   2640
gatgcttaca tttcttatga caccaaagat gcctctgtta ctgactgggt gataaatgag   2700
ctgcgctacc accttgaaga gagccgagac aaaaacgttc tcctttgtct agaggagagg   2760
gattgggacc cgggattggc catcatcgac aacctcatgc agagcatcaa ccaaagcaag   2820
aaaacagtat ttgttttaac caaaaaatat gcaaaaagct ggaactttaa acagcttttt   2880
tacttggctt tgcagaggct aatggatgag aacatggatg tgattatatt tatcctgctg   2940
gagccagtgt tacagcattc tcagtatttg aggctacggc agcggatctg taagagctcc   3000
atcctccagt ggcctgacaa cccgaaggca gaaggcttgt tttggcaaac tctgagaaat   3060
gtggtcttga ctgaaaatga ttcacggtat aacaatatgt atgtcgattc cattaagcaa   3120
tactaa                                                               3126
```

<210> SEQ ID NO 11
<211> LENGTH: 1032

<212> TYPE: PRT
<213> ORGANISM: Homo sapiens

<400> SEQUENCE: 11

```
Met Gly Phe Cys Arg Ser Ala Leu His Pro Leu Ser Leu Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
        195                 200                 205

Asn Asn Leu Thr Val Val Pro Arg Asn Leu Pro Ser Ser Leu Glu Tyr
    210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
        275                 280                 285

Leu Val Leu Lys Asp Ser Ser Leu Ser Trp Leu Asn Ala Ser Trp Phe
    290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
        355                 360                 365

Leu Asp Met His Gly Ile Phe Phe Arg Ser Leu Asp Glu Thr Thr Leu
    370                 375                 380

Arg Pro Leu Ala Arg Leu Pro Met Leu Gln Thr Leu Arg Leu Gln Met
385                 390                 395                 400
```

```
Asn Phe Ile Asn Gln Ala Gln Leu Gly Ile Phe Arg Ala Phe Pro Gly
            405                 410                 415

Leu Arg Tyr Val Asp Leu Ser Asp Asn Arg Ile Ser Gly Ala Ser Glu
            420                 425                 430

Leu Thr Ala Thr Met Gly Glu Ala Asp Gly Gly Glu Lys Val Trp Leu
            435                 440                 445

Gln Pro Gly Asp Leu Ala Pro Ala Pro Val Asp Thr Pro Ser Ser Glu
450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
            485                 490                 495

His Leu Gln Cys Leu Arg Leu Ser His Asn Cys Ile Ser Gln Ala Val
            500                 505                 510

Asn Gly Ser Gln Phe Leu Pro Leu Thr Gly Leu Gln Val Leu Asp Leu
            515                 520                 525

Ser His Asn Lys Leu Asp Leu Tyr His Glu His Ser Phe Thr Glu Leu
            530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
            565                 570                 575

Leu Arg His Leu Ser Leu Ala His Asn Asn Ile His Ser Gln Val Ser
            580                 585                 590

Gln Gln Leu Cys Ser Thr Ser Leu Arg Ala Leu Asp Phe Ser Gly Asn
            595                 600                 605

Ala Leu Gly His Met Trp Ala Glu Gly Asp Leu Tyr Leu His Phe Phe
            610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
            645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Gln
            675                 680                 685

Leu Lys Ala Leu Thr Asn Gly Ser Leu Pro Ala Gly Thr Arg Leu Arg
            690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
            725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
            755                 760                 765

Ala Phe Met Asp Phe Leu Leu Glu Val Gln Ala Ala Val Pro Gly Leu
            770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
            805                 810                 815
```

Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
        835                 840                 845

Leu Cys Leu Ala Trp Leu Pro Trp Arg Gly Arg Gln Ser Gly Arg Asp
    850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
        900                 905                 910

Trp Leu Pro Gly Lys Thr Leu Phe Glu Asn Leu Trp Ala Ser Val Tyr
    915                 920                 925

Gly Ser Arg Lys Thr Leu Phe Val Leu Ala His Thr Asp Arg Val Ser
    930                 935                 940

Gly Leu Leu Arg Ala Ser Phe Leu Leu Ala Gln Gln Arg Leu Leu Glu
945                 950                 955                 960

Asp Arg Lys Asp Val Val Val Leu Val Ile Leu Ser Pro Asp Gly Arg
                965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
                995                 1000                1005

Leu Gly Met Ala Leu Thr Arg Asp Asn His His Phe Tyr Asn Arg
        1010                1015                1020

Asn Phe Cys Gln Gly Pro Thr Ala Glu
    1025                1030

<210> SEQ ID NO 12
<211> LENGTH: 3099
<212> TYPE: DNA
<213> ORGANISM: Homo sapiens

<400> SEQUENCE: 12 atgggttct gccgcagcgc cctgcacccg ctgtctctcc tggtgcaggc catcatgctg     60
gccatgaccc tggccctggg taccttgcct gccttcctac cctgtgagct ccagccccac    120
ggcctggtga actgcaactg ctgttcctg aagtctgtgc cccacttctc catggcagca    180
ccccgtggca atgtcaccag cctttccttg tcctccaacc gcatccacca cctccatgat    240
tctgactttg cccacctgcc cagcctgcgg catctcaacc tcaagtggaa ctgcccgccg    300
gttggcctca gccccatgca cttccctgc cacatgacca tcgagcccag caccttcttg    360
gctgtgccca ccctggaaga gctaaacctg agctacaaca catcatgac tgtgcctgcg    420 ctgcccaaat ccctcatatc cctgtccctc agccatacca catcctgat gctagactct    480 gccagcctcg ccggcctgca tgccctgcgc ttcctattca tggacggcaa ctgttattac    540
aagaacccct gcaggcaggc actggaggtg gccccgggtg ccctccttgg cctgggcaac    600
ctcacccacc tgtcactcaa gtacaacaac ctcactgtgg tgccccgcaa cctgccttcc    660
agcctggagt atctgctgtt gtcctacaac cgcatcgtca actggcgcc tgaggacctg    720 gccaatctga ccgccctgcg tgtgctcgat gtgggcggaa attgccgccg ctgcgaccac    780
gctcccaacc cctgcatgga gtgccctcgt cacttccccc agctacatcc cgatccttc    840 agccacctga gccgtcttga aggcctggtg ttgaaggaca gttctctctc ctggctgaat    900

```
gccagttggt tccgtgggct gggaaacctc cgagtgctgg acctgagtga aacttcctc     960 tacaaatgca tcactaaaac caaggccttc cagggcctaa cacagctgcg caagcttaac    1020
ctgtccttca attaccaaaa gagggtgtcc tttgcccacc tgtctctggc cccttccttc    1080
gggagcctgg tcgccctgaa ggagctggac atgcacggca tcttcttccg ctcactcgat    1140
gagaccacgc tccggccact ggcccgcctg cccatgctcc agactctgcg tctgcagatg    1200
aacttcatca accaggccca gctcggcatc ttcaggccct ccctggcct gcgctacgtg     1260 gacctgtcgg acaaccgcat cagcggagct cggagctga cagccaccat ggggggaggca    1320 gatggagggg agaaggtctg gctgcagcct ggggaccttg ctccggcccc agtggacact    1380
cccagctctg aagacttcag gcccaactgc agcaccctca acttcacctt ggatctgtca    1440
cggaacaacc tggtgaccgt gcagccggag atgtttgccc agctctcgca cctgcagtgc    1500
ctgcgcctga ccacaactg catctcgcag gcagtcaatg ctcccagtt cctgccgctg      1560 accggtctgc aggtgctaga cctgtcccac aataagctgg acctctacca cgagcactca    1620
ttcacggagc taccgcgact ggaggccctg gacctcagct acaacagcca gcccttggc    1680 atgcagggcg tgggccacaa cttcagcttc gtggctcacc tgcgcaccct cgcgcacctc    1740
agcctggccc acaacaacat ccacagccaa gtgtcccagc agctctgcag tacgtcgctg    1800
cgggccctgg acttcagcgg caatgcactg ggccatatgt gggccgaggg agacctctat   1860
ctgcacttct ccaaggcct gagcggtttg atctggctgg acttgtccca gaaccgcctg     1920
cacaccctcc tgccccaaac cctgcgcaac ctccccaaga gcctacaggt gctgcgtctc    1980
cgtgacaatt acctggcctt cttttaagtgg tggagcctcc acttcctgcc caaactggaa   2040
gtcctcgacc tggcaggaaa ccagctgaag gccctgacca atggcagcct gctgctggc    2100 acccggctcc ggaggctgga tgtcagctgc aacagcatca gcttcgtggc ccccggcttc    2160
ttttccaagg ccaaggagct gcgagagctc aaccttagcg ccaacgccct caagacagtg   2220
gaccactcct ggtttgggcc cctggcgagt gccctgcaaa tactagatgt aagcgccaac    2280
cctctgcact gcgcctgtgg ggcggccttt atggacttcc tgctggaggt gcaggctgcc    2340
gtgcccggtc tgcccagccg ggtgaagtgt ggcagtccgg ccagctcca gggcctcagc    2400 atctttgcac aggacctgcg cctctgcctg gatgaggccc tctcctggga ctgtttcgcc    2460
ctctcgctgc tggctgtggc tctgggcctg gtgtgccca tgctgcatca cctctgtggc    2520
tgggacctct ggtactgctt ccacctgtgc ctggcctggc ttccctggcg ggggcggcaa   2580
agtgggcgag atgaggatgc cctgccctac gatgccttcg tggtcttcga caaaacgcag   2640
agcgcagtgg cagactgggt gtacaacgag cttcggggc agctggagga gtgccgtggg   2700
cgctgggcac tccgcctgtg cctggaggaa cgcgactggc tgcctggcaa aaccctcttt    2760
gagaacctgt gggcctcggt ctatggcagc cgcaagacgc tgtttgtgct ggcccacacg   2820
gaccgggtca gtggtctctt gcgcgccagc ttcctgctgg cccagcagcg cctgctggag   2880
gaccgcaagg acgtcgtggt gctggtgatc ctgagccctg acggccgccg ctcccgctac    2940
gtgcggctgc gccagcgcct ctgccgccag agtgtcctcc tctggcccca ccagcccagt    3000
ggtcagcgca gcttctgggc ccagctgggc atggccctga ccaggggacaa ccaccacttc    3060 tataaccgga acttctgcca gggacccacg gccgaatag                            3099
```

<210> SEQ ID NO 13
<211> LENGTH: 317
<212> TYPE: PRT

<213> ORGANISM: Homo sapiens

<400> SEQUENCE: 13

| | | | | | | | | | | | | | | | |
|---|---|---|---|---|---|---|---|---|---|---|---|---|---|---|---|
| Met | Thr | Met | Glu | Thr | Gln | Met | Ser | Gln | Asn | Val | Cys | Pro | Arg | Asn | Leu |
| 1 | | | | 5 | | | | | 10 | | | | | 15 | |
| Trp | Leu | Leu | Gln | Pro | Leu | Thr | Val | Leu | Leu | Leu | Ala | Ser | Ala | Asp | |
| | | | 20 | | | | | 25 | | | | | 30 | | |
| Ser | Gln | Ala | Ala | Ala | Pro | Pro | Lys | Ala | Val | Leu | Lys | Leu | Glu | Pro | Pro |
| | | 35 | | | | | 40 | | | | | 45 | | | |
| Trp | Ile | Asn | Val | Leu | Gln | Glu | Asp | Ser | Val | Thr | Leu | Thr | Cys | Gln | Gly |
| | 50 | | | | | 55 | | | | | 60 | | | | |
| Ala | Arg | Ser | Pro | Glu | Ser | Asp | Ser | Ile | Gln | Trp | Phe | His | Asn | Gly | Asn |
| 65 | | | | | 70 | | | | | 75 | | | | | 80 |
| Leu | Ile | Pro | Thr | His | Thr | Gln | Pro | Ser | Tyr | Arg | Phe | Lys | Ala | Asn | Asn |
| | | | | 85 | | | | | 90 | | | | | 95 | |
| Asn | Asp | Ser | Gly | Glu | Tyr | Thr | Cys | Gln | Thr | Gly | Gln | Thr | Ser | Leu | Ser |
| | | | 100 | | | | | 105 | | | | | 110 | | |
| Asp | Pro | Val | His | Leu | Thr | Val | Leu | Ser | Glu | Trp | Leu | Val | Leu | Gln | Thr |
| | | 115 | | | | | 120 | | | | | 125 | | | |
| Pro | His | Leu | Glu | Phe | Gln | Glu | Gly | Glu | Thr | Ile | Met | Leu | Arg | Cys | His |
| | 130 | | | | | 135 | | | | | 140 | | | | |
| Ser | Trp | Lys | Asp | Lys | Pro | Leu | Val | Lys | Val | Thr | Phe | Phe | Gln | Asn | Gly |
| 145 | | | | | 150 | | | | | 155 | | | | | 160 |
| Lys | Ser | Gln | Lys | Phe | Ser | His | Leu | Asp | Pro | Thr | Phe | Ser | Ile | Pro | Gln |
| | | | | 165 | | | | | 170 | | | | | 175 | |
| Ala | Asn | His | Ser | His | Ser | Gly | Asp | Tyr | His | Cys | Thr | Gly | Asn | Ile | Gly |
| | | | 180 | | | | | 185 | | | | | 190 | | |
| Tyr | Thr | Leu | Phe | Ser | Ser | Lys | Pro | Val | Thr | Ile | Thr | Val | Gln | Val | Pro |
| | | 195 | | | | | 200 | | | | | 205 | | | |
| Ser | Met | Gly | Ser | Ser | Ser | Pro | Met | Gly | Ile | Ile | Val | Ala | Val | Val | Ile |
| | 210 | | | | | 215 | | | | | 220 | | | | |
| Ala | Thr | Ala | Val | Ala | Ala | Ile | Val | Ala | Ala | Val | Val | Ala | Leu | Ile | Tyr |
| 225 | | | | | 230 | | | | | 235 | | | | | 240 |
| Cys | Arg | Lys | Lys | Arg | Ile | Ser | Ala | Asn | Ser | Thr | Asp | Pro | Val | Lys | Ala |
| | | | | 245 | | | | | 250 | | | | | 255 | |
| Ala | Gln | Phe | Glu | Pro | Pro | Gly | Arg | Gln | Met | Ile | Ala | Ile | Arg | Lys | Arg |
| | | | 260 | | | | | 265 | | | | | 270 | | |
| Gln | Leu | Glu | Glu | Thr | Asn | Asn | Asp | Tyr | Glu | Thr | Ala | Asp | Gly | Gly | Tyr |
| | | 275 | | | | | 280 | | | | | 285 | | | |
| Met | Thr | Leu | Asn | Pro | Arg | Ala | Pro | Thr | Asp | Asp | Lys | Asn | Ile | Tyr | |
| | 290 | | | | | 295 | | | | | 300 | | | | |
| Leu | Thr | Leu | Pro | Pro | Asn | Asp | His | Val | Asn | Ser | Asn | Asn | | | |
| 305 | | | | | 310 | | | | | 315 | | | | | |

<210> SEQ ID NO 14
<211> LENGTH: 954
<212> TYPE: DNA
<213> ORGANISM: Homo sapiens

<400> SEQUENCE: 14

```
atgactatgg agacccaaat gtctcagaat gtatgtccca gaaacctgtg gctgcttcaa      60
ccattgacag ttttgctgct gctggcttct gcagacagtc aagctgcagc tcccccaaag     120
gctgtgctga acttgagcc ccgtggatc aacgtgctcc aggaggactc tgtgactctg      180
acatgccagg gggctcgcag ccctgagagc gactccattc agtggttcca caatgggaat     240
```

```
ctcattccca cccacacgca gcccagctac aggttcaagg ccaacaacaa tgacagcggg      300
gagtacacgt gccagactgg ccagaccagc ctcagcgacc ctgtgcatct gactgtgctt      360
tccgaatggc tggtgctcca gacccctcac ctggagttcc aggagggaga accatcatg       420 ctgaggtgcc acagctggaa ggacaagcct ctggtcaagg tcacattctt ccagaatgga      480
aaatcccaga aattctccca tttggatccc accttctcca tcccacaagc aaaccacagt      540
cacagtggtg attaccactg cacaggaaac ataggctaca cgctgttctc atccaagcct      600
gtgaccatca ctgtccaagt gcccagcatg ggcagctctt caccaatggg gatcattgtg      660
gctgtggtca ttgcgactgc tgtagcagcc attgttgctg ctgtagtggc cttgatctac      720
tgcaggaaaa agcggatttc agccaattcc actgatcctg tgaaggctgc ccaatttgag      780
ccacctggac gtcaaatgat tgccatcaga aagagacaac ttgaagaaac caacaatgac      840
tatgaaacag ctgacggcgg ctacatgact ctgaacccca gggcacctac tgacgatgat      900
aaaaacatct acctgactct tcctcccaac gaccatgtca acagtaataa ctaa            954
```

<210> SEQ ID NO 15
<211> LENGTH: 254
<212> TYPE: PRT
<213> ORGANISM: Homo sapiens

<400> SEQUENCE: 15

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 16
<211> LENGTH: 765
<212> TYPE: DNA
<213> ORGANISM: Homo sapiens

<400> SEQUENCE: 16

```
atgtggcagc tgctcctccc aactgctctg ctacttctag tttcagctgg catgcggact    60
gaagatctcc caaaggctgt ggtgttcctg gagcctcaat ggtacagggt gctcgagaag   120
gacagtgtga ctctgaagtg ccagggagcc tactcccctg aggacaattc cacacagtgg   180
tttcacaatg agagcctcat ctcaagccag gcctcgagct acttcattga cgctgccaca   240
gtcgacgaca gtggagagta caggtgccag acaaacctct ccaccctcag tgacccggtg   300
cagctagaag tccatatcgg ctggctgttg ctccaggccc tcggtgggt gttcaaggag    360
gaagaccta ttcacctgag gtgtcacagc tggaagaaca ctgctctgca taaggtcaca    420
tatttacaga atggcaaagg caggaagtat tttcatcata attctgactt ctacattcca   480
aaagccacac tcaaagacag cggctcctac ttctgcaggg ggcttttgg gagtaaaaat    540
gtgtcttcag agactgtgaa catcaccatc actcaaggtt tggcagtgtc aaccatctca   600
tcattctttc cacctgggta ccaagtctct ttctgcttgg tgatggtact ccttttgca    660
gtggacacag gactatattt ctctgtgaag acaaacattc gaagctcaac aagagactgg   720
aaggaccata atttaaatg gagaaaggac cctcaagaca aatga                    765
```

<210> SEQ ID NO 17
<211> LENGTH: 86
<212> TYPE: PRT
<213> ORGANISM: Homo sapiens

<400> SEQUENCE: 17

```
Met Ile Pro Ala Val Leu Leu Leu Leu Val Glu Gln Ala
1               5                   10                  15
Ala Ala Leu Gly Glu Pro Gln Leu Cys Tyr Ile Leu Asp Ala Ile Leu
            20                  25                  30
Phe Leu Tyr Gly Ile Val Leu Thr Leu Leu Tyr Cys Arg Leu Lys Ile
        35                  40                  45
Gln Val Arg Lys Ala Ala Ile Thr Ser Tyr Glu Lys Ser Asp Gly Val
    50                  55                  60
Tyr Thr Gly Leu Ser Thr Arg Asn Gln Glu Thr Tyr Glu Thr Leu Lys
65                  70                  75                  80
His Glu Lys Pro Pro Gln
                85
```

<210> SEQ ID NO 18
<211> LENGTH: 261
<212> TYPE: DNA
<213> ORGANISM: Homo sapiens

<400> SEQUENCE: 18

```
atgattccag cagtggtctt gctcttactc cttttggttg aacaagcagc ggccctggga    60
gagcctcagc tctgctatat cctggatgcc atcctgtttc tgtatggaat tgtcctcacc   120
ctcctctact gtcgactgaa gatccaagtg cgaaaggcag ctataaccag ctatgagaaa   180
tcagatggtg tttacacggg cctgagcacc aggaaccagg agacttacga gactctgaag   240
catgagaaac caccacagta g                                             261
```

<210> SEQ ID NO 19
<211> LENGTH: 296
<212> TYPE: PRT
<213> ORGANISM: Homo sapiens

<400> SEQUENCE: 19

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
        195                 200                 205

Ser Glu Leu Ile Glu Lys Arg Cys Arg Arg Met Val Val Val Val Ser
    210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Leu Ile Pro Ile Lys
                245                 250                 255

Tyr Lys Ala Met Lys Lys Glu Phe Pro Ser Ile Leu Arg Phe Ile Thr
            260                 265                 270

Val Cys Asp Tyr Thr Asn Pro Cys Thr Lys Ser Trp Phe Trp Thr Arg
        275                 280                 285

Leu Ala Lys Ala Leu Ser Leu Pro
    290                 295

<210> SEQ ID NO 20
<211> LENGTH: 954
<212> TYPE: DNA
<213> ORGANISM: Homo sapiens

<400> SEQUENCE: 20
atgcgacccg accgcgctga ggctccagga ccgcccgcca tggctgcagg aggtcccggc     60
gcggggtctg cggccccggt ctcctccaca tcctcccttc ccctggctgc tctcaacatg    120
cgagtgcggc gccgcctgtc tctgttcttg aacgtgcgga cacaggtggc ggccgactgg    180

```
accgcgctgg cggaggagat ggactttgag tacttggaga tccggcaact ggagacacaa    240
gcggacccca ctggcaggct gctggacgcc tggcagggac gccctggcgc ctctgtaggc    300
cgactgctcg agctgcttac caagctgggc cgcgacgacg tgctgctgga gctgggaccc    360
agcattgagg aggattgcca aaagtatatc ttgaagcagc agcaggagga ggctgagaag    420
cctttacagg tggccgctgt agacagcagt gtcccacgga cagcagagct ggcgggcatc    480
accacacttg atgacccct gggcatatg cctgagcgtt tcgatgcctt catctgctat    540
tgccccagcg acatccagtt tgtgcaggag atgatccggc aactggaaca gacaaactat    600
cgactgaagt tgtgtgtgtc tgaccgcgat gtcctgcctg cacctgtgt ctggtctatt    660 gctagtgagc tcatcgaaaa gaggttggct agaaggccac ggggtgggtg ccgccggatg    720
gtggtggttg tctctgatga ttacctgcag agcaaggaat gtgacttcca gaccaaattt    780
gcactcagcc tctctccagg tgcccatcag aagcgactga tccccatcaa gtacaaggca    840
atgaagaaag agttccccag catcctgagg ttcatcactg tctgcgacta caccaacccc    900
tgcaccaaat cttggttctg gactcgcctt gccaaggcct tgtccctgcc ctga          954
```

<210> SEQ ID NO 21
<211> LENGTH: 153
<212> TYPE: PRT
<213> ORGANISM: Homo sapiens

<400> SEQUENCE: 21

```
Met Ala Pro Ala Ala Thr Gly Gly Ser Thr Leu Pro Ser Gly Phe
1               5                   10                  15

Ser Val Phe Thr Thr Leu Pro Asp Leu Leu Phe Ile Phe Glu Phe Ile
                20                  25                  30

Phe Gly Gly Leu Val Trp Ile Leu Val Ala Ser Ser Leu Val Pro Trp
            35                  40                  45

Pro Leu Val Gln Gly Trp Val Met Phe Val Ser Val Phe Cys Phe Val
        50                  55                  60

Ala Thr Thr Thr Leu Ile Ile Leu Tyr Ile Ile Gly Ala His Gly Gly
65                  70                  75                  80

Glu Thr Ser Trp Val Thr Leu Asp Ala Ala Tyr His Cys Thr Ala Ala
                85                  90                  95

Leu Phe Tyr Leu Ser Ala Ser Val Leu Glu Ala Leu Ala Thr Ile Thr
            100                 105                 110

Met Gln Asp Gly Phe Thr Tyr Arg His Tyr His Glu Asn Ile Ala Ala
        115                 120                 125

Val Val Phe Ser Tyr Ile Ala Thr Leu Leu Tyr Val Val His Ala Val
    130                 135                 140

Phe Ser Leu Ile Arg Trp Lys Ser Ser
145                 150
```

<210> SEQ ID NO 22
<211> LENGTH: 462
<212> TYPE: DNA
<213> ORGANISM: Homo sapiens

<400> SEQUENCE: 22

```
atggccccg cagcggcgac ggggggcagc accctgccca gtggcttctc ggtcttcacc    60
acctcgcccg acttgctctt catctttgag tttatcttcg ggggcctggt gtggatcctg    120
gtggcctcct ccctggtgcc ctggcccctg gtccagggct gggtgatgtt cgtgtctgtg    180
```

```
ttctgcttcg tggccaccac caccttgatc atcctgtaca taattggagc ccacggtgga    240
gagacttcct gggtcacctt ggacgcagcc taccactgca ccgctgccct cttttacctc    300
agcgcctcag tcctggaggc cctggccacc atcacgatgc aagacggctt cacctacagg    360
cactaccatg aaaacattgc tgccgtggtg ttctcctaca tagccactct gctctacgtg    420
gtccatgcgg tgttctcttt aatcagatgg aagtcttcat aa                        462
```

<210> SEQ ID NO 23
<211> LENGTH: 712
<212> TYPE: PRT
<213> ORGANISM: Homo sapiens

<400> SEQUENCE: 23

```
Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
                20                  25                  30

Val Met Asp Ala Leu Glu Pro Ala Asp Trp Cys Gln Phe Ala Ala Leu
            35                  40                  45

Ile Val Arg Asp Gln Thr Glu Leu Arg Leu Cys Glu Arg Ser Gly Gln
        50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
        275                 280                 285

Gly Phe Leu Pro Asn Gly Ser Leu Glu Asp Arg Leu His Cys Gln Thr
    290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
```

```
                    325                 330                 335
Ile His Gly Asp Ile Lys Ser Ser Asn Val Leu Leu Asp Glu Arg Leu
                340                 345                 350

Thr Pro Lys Leu Gly Asp Phe Gly Leu Ala Arg Phe Ser Arg Phe Ala
            355                 360                 365

Gly Ser Ser Pro Ser Gln Ser Ser Met Val Ala Arg Thr Gln Thr Val
        370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Leu Glu
                405                 410                 415

Thr Leu Ala Gly Gln Arg Ala Val Lys Thr His Gly Ala Arg Thr Lys
                420                 425                 430

Tyr Leu Lys Asp Leu Val Glu Glu Ala Glu Ala Gly Val Ala
                435                 440                 445

Leu Arg Ser Thr Gln Ser Thr Leu Gln Ala Gly Leu Ala Ala Asp Ala
                450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gly Gln Leu
                485                 490                 495

Ala Cys Cys Cys Leu His Arg Arg Ala Lys Arg Arg Pro Pro Met Thr
                500                 505                 510

Gln Val Tyr Glu Arg Leu Glu Lys Leu Gln Ala Val Val Ala Gly Val
                515                 520                 525

Pro Gly His Ser Glu Ala Ala Ser Cys Ile Pro Pro Ser Pro Gln Glu
                530                 535                 540

Asn Ser Tyr Val Ser Ser Thr Gly Arg Ala His Ser Gly Ala Ala Pro
545                 550                 555                 560

Trp Gln Pro Leu Ala Ala Pro Ser Gly Ala Ser Ala Gln Ala Ala Glu
                565                 570                 575

Gln Leu Gln Arg Gly Pro Asn Gln Pro Val Glu Ser Asp Glu Ser Leu
                580                 585                 590

Gly Gly Leu Ser Ala Ala Leu Arg Ser Trp His Leu Thr Pro Ser Cys
                595                 600                 605

Pro Leu Asp Pro Ala Pro Leu Arg Glu Ala Gly Cys Pro Gln Gly Asp
                610                 615                 620

Thr Ala Gly Glu Ser Ser Trp Gly Ser Gly Pro Gly Ser Arg Pro Thr
625                 630                 635                 640

Ala Val Glu Gly Leu Ala Leu Gly Ser Ala Ser Ser Ser Glu
                645                 650                 655

Pro Pro Gln Ile Ile Ile Asn Pro Ala Arg Gln Lys Met Val Gln Lys
                660                 665                 670

Leu Ala Leu Tyr Glu Asp Gly Ala Leu Asp Ser Leu Gln Leu Leu Ser
                675                 680                 685

Ser Ser Ser Leu Pro Gly Leu Gly Leu Glu Gln Asp Arg Gln Gly Pro
                690                 695                 700

Glu Glu Ser Asp Glu Phe Gln Ser
705                 710

<210> SEQ ID NO 24
<211> LENGTH: 2139
<212> TYPE: DNA
<213> ORGANISM: Homo sapiens
```

<400> SEQUENCE: 24

```
atggccgggg ggccgggccc gggggagccc gcagccccg gcgcccagca cttcttgtac      60
gaggtgccgc cctgggtcat gtgccgcttc tacaaagtga tggacgccct ggagcccgcc    120
gactggtgcc agttcgccgc cctgatcgtg cgcgaccaga ccgagctgcg gctgtgcgag    180
cgctccgggc agcgcacggc cagcgtcctg tggccctgga tcaaccgcaa cgcccgtgtg    240
gccgacctcg tgcacatcct cacgcacctg cagctgctcc gtgcgcggga catcatcaca    300
gcctggcacc ctcccgcccc gcttccgtcc ccaggcacca ctgccccgag gcccagcagc    360
atccctgcac ccgccgaggc cgaggcctgg agccccgga agttgccatc ctcagcctcc    420
accttcctct ccccagcttt tccaggctcc cagacccatt cagggcctga gctcggcctg    480
gtcccaagcc ctgcttccct gtggcctcca ccgccatctc cagccccttc ttctaccaag    540
ccaggcccag agagctcagt gtccctcctg cagggagccc gcccctttcc gttttgctgg    600
cccctctgtg agatttcccg gggcacccac aacttctcgg aggagctcaa gatcggggag    660
ggtggctttg ggtgcgtgta ccgggcggtg atgaggaaca cggtgtatgc tgtgaagagg    720
ctgaaggaga cgctgacct ggagtggact gcagtgaagc agagcttcct gaccgaggtg    780
gagcagctgt ccaggtttcg tcacccaaac attgtggact ttgctggcta ctgtgctcag    840
aacggcttct actgcctggt gtacggcttc ctgcccaacg ctccctgga ggaccgtctc    900
cactgccaga cccaggcctg cccacctctc tcctggcctc agcgactgga catccttctg    960
ggtacagccc gggcaattca gtttctacat caggacagcc ccagcctcat ccatggagac   1020
atcaagagtt ccaacgtcct tctggatgag aggctgacac ccaagctggg agactttggc   1080
ctggcccggt tcagccgctt tgccgggtcc agccccagcc agagcagcat ggtggcccgg   1140
acacagacag tgcggggcac cctggcctac ctgcccgagg agtacatcaa gacgggaagg   1200
ctggctgtgg acacggacac cttcagctt gggggtggtag tgctagagac cttggctggt   1260
cagagggctg tgaagacgca cggtgccagg accaagtatc tgaaagacct ggtggaagag   1320
gaggctgagg aggctggagt ggctttgaga agcacccaga gcacactgca agcaggtctg   1380
gctgcagatg cctgggctgc tcccatcgcc atgcagatct acaagaagca cctggacccc   1440
aggcccgggc cctgcccacc tgagctgggc ctgggcctgg ccagctggc ctgctgctgc   1500
ctgcaccgcc gggccaaaag gaggcctcct atgacccagt gtacgagag ctagagaag   1560
ctgcaggcag tggtggcggg ggtgcccggg cattcggagg ccgccagctg catccccct   1620
tccccgcagg agaactccta cgtgtccagc actggcagag cccacagtgg ggctgctcca   1680
tggcagcccc tggcagcgcc atcaggagcc agtgcccagg cagcagagca gctgcagaga   1740
ggccccaacc agcccgtgga gagtgacgag agcctaggcg gcctctctgc tgccctgcgc   1800
tcctggcact tgactccaag ctgccctctg acccagcac ccctcaggga ggccggctgt   1860
cctcagggggg acacggcagg agaatcgagc tgggggagtg gccaggatc ccggcccaca   1920
gccgtggaag gactggccct tggcagctct gcatcatcgt cgtcagagcc accgcagatt   1980
atcatcaacc ctgcccgaca gaagatggtc cagaagctgg ccctgtacga ggatggggcc   2040
ctggacagcc tgcagctgct gtcgtccagc tccctcccag gcttgggcct ggaacaggac   2100
aggcaggggc ccgaagaaag tgatgaattt cagagctga                         2139
```

<210> SEQ ID NO 25
<211> LENGTH: 257
<212> TYPE: PRT

<213> ORGANISM: Artificial Sequence
<220> FEATURE:
<223> OTHER INFORMATION: ScFv fragment

<400> SEQUENCE: 25

Met Ser Arg Gly Gln Ile Val Leu Ser Gln Ser Pro Ala Ile Leu Ser
1               5                   10                  15

Ala Ser Pro Gly Glu Lys Val Thr Met Thr Cys Arg Ala Ser Ser Ser
            20                  25                  30

Val Ser Tyr Met His Phe Tyr Gln Gln Lys Pro Gly Ser Ser Pro Lys
        35                  40                  45

Pro Trp Ile Tyr Ala Thr Ser Asn Leu Ala Ser Gly Val Pro Ala Arg
    50                  55                  60

Phe Ser Gly Ser Gly Ser Gly Thr Ser Phe Ser Leu Thr Ile Ser Arg
65                  70                  75                  80

Val Glu Ala Glu Asp Ala Ala Thr Tyr Tyr Cys Gln Gln Trp Ser Ser
                85                  90                  95

Asn Pro Pro Thr Phe Gly Ser Gly Thr Lys Leu Glu Ile Lys Ser Gly
            100                 105                 110

Gly Gly Gly Ser Gly Gly Gly Gly Ser Gly Gly Gly Ser Met Ala
        115                 120                 125

Val Val Thr Gly Val Asn Ser Glu Val Gln Leu Gln Gln Ser Gly Ala
        130                 135                 140

Glu Leu Val Lys Pro Gly Ala Ser Val Lys Leu Ser Cys Thr Ala Ser
145                 150                 155                 160

Gly Phe Asn Ile Lys Asp Thr Tyr Ile His Trp Val Lys Gln Arg Pro
            165                 170                 175

Glu Gln Gly Leu Glu Trp Ile Gly Arg Ile Asp Pro Ala Asn Gly Asn
        180                 185                 190

Thr Lys Tyr Asp Pro Lys Phe Gln Gly Lys Ala Thr Ile Thr Thr Asp
    195                 200                 205

Thr Ser Phe Asn Thr Ala Tyr Leu Gln Leu Ser Ser Leu Thr Ser Glu
        210                 215                 220

Asp Thr Ala Val Tyr Tyr Cys Ala Lys Val Gly Tyr Gly His Trp Tyr
225                 230                 235                 240

Phe Asp Val Trp Gly Ala Gly Thr Thr Val Thr Val Ser Ser Val Asp
            245                 250                 255

Leu

<210> SEQ ID NO 26
<211> LENGTH: 5
<212> TYPE: PRT
<213> ORGANISM: Artificial Sequence
<220> FEATURE:
<223> OTHER INFORMATION: Short hinge linker

<400> SEQUENCE: 26

Met Asn Lys Thr Ile
1               5

<210> SEQ ID NO 27
<211> LENGTH: 55
<212> TYPE: PRT
<213> ORGANISM: Artificial Sequence
<220> FEATURE:
<223> OTHER INFORMATION: Long hinge linker

<400> SEQUENCE: 27

```
Asn Asp Phe Ala Cys Thr Cys Glu His Gln Ser Phe Leu Gln Trp Ile
1               5                   10                  15

Lys Asp Gln Arg Gln Leu Leu Val Glu Val Glu Arg Met Glu Cys Ala
            20                  25                  30

Thr Pro Ser Asp Lys Gln Gly Met Pro Val Leu Ser Leu Asn Ile Thr
        35                  40                  45

Cys Gln Met Asn Lys Thr Ile
    50                  55

<210> SEQ ID NO 28
<211> LENGTH: 327
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

-continued

Leu Ser Leu Ser Leu Gly Lys
              325

<210> SEQ ID NO 29
<211> LENGTH: 12
<212> TYPE: PRT
<213> ORGANISM: Homo sapiens

<400> SEQUENCE: 29

Glu Ser Lys Tyr Gly Pro Pro Cys Pro Pro Cys Pro
1               5                   10

<210> SEQ ID NO 30
<211> LENGTH: 119
<212> TYPE: PRT
<213> ORGANISM: Homo sapiens

<400> SEQUENCE: 30

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 31
<211> LENGTH: 228
<212> TYPE: PRT
<213> ORGANISM: Homo sapiens

<400> SEQUENCE: 31

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

```
Val Tyr Thr Leu Pro Pro Ser Gln Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
                180                 185                 190

Val Asp Lys Ser Arg Trp Gln Gln Gly Asn Val Phe Ser Cys Ser Val
                195                 200                 205

Met His Glu Ala Leu His Asn His Tyr Thr Gln Lys Ser Leu Ser Leu
210                 215                 220

Ser Leu Gly Lys
225

<210> SEQ ID NO 32
<211> LENGTH: 235
<212> TYPE: PRT
<213> ORGANISM: Homo sapiens

<400> SEQUENCE: 32

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
                130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 33
<211> LENGTH: 68
<212> TYPE: PRT
<213> ORGANISM: Artificial Sequence
```

```
<220> FEATURE:
<223> OTHER INFORMATION: Mutated CD8 hinge

<400> SEQUENCE: 33

Ser Ala Leu Ser Asn Ser Ile Met Tyr Phe Ser His Phe Val Pro Val
1               5                   10                  15

Phe Leu Pro Ala Lys Pro Thr Thr Thr Pro Ala Pro Arg Pro Pro Thr
            20                  25                  30

Pro Ala Pro Thr Ile Ala Ser Gln Pro Leu Ser Leu Arg Pro Glu Ala
        35                  40                  45

Ser Arg Pro Ala Ala Gly Gly Ala Val His Thr Arg Gly Leu Asp Phe
    50                  55                  60

Ala Ser Asp Ile
65

<210> SEQ ID NO 34
<211> LENGTH: 15
<212> TYPE: PRT
<213> ORGANISM: Artificial Sequence
<220> FEATURE:
<223> OTHER INFORMATION: GS linker

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 496
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<220> FEATURE:
<221> NAME/KEY: MISC_FEATURE
<222> LOCATION: (19)..(275)
<223> OTHER INFORMATION: TK1-ScFv
<220> FEATURE:
<221> NAME/KEY: MISC_FEATURE
<222> LOCATION: (276)..(290)
<223> OTHER INFORMATION: GS-Linker
<220> FEATURE:
<221> NAME/KEY: MISC_FEATURE
<222> LOCATION: (291)..(313)
<223> OTHER INFORMATION: TLR4-Transmembrane domain
<220> FEATURE:
<221> NAME/KEY: MISC_FEATURE
<222> LOCATION: (314)..(496)
<223> OTHER INFORMATION: TLR4-Cytosolic domain

<400> SEQUENCE: 35

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95
```

```
            Ser Arg Val Glu Ala Glu Asp Ala Ala Thr Tyr Tyr Cys Gln Gln Trp
                    100                 105                 110

Ser Ser Asn Pro Pro Thr Phe Gly Ser Gly Thr Lys Leu Glu Ile Lys
                    115                 120                 125

Ser Gly Gly Gly Ser Gly Gly Gly Ser Gly Gly Gly Ser
                    130                 135                 140

Met Ala Val Val Thr Gly Val Asn Ser Glu Val Gln Leu Gln Gln Ser
            145                 150                 155                 160

Gly Ala Glu Leu Val Lys Pro Gly Ala Ser Val Lys Leu Ser Cys Thr
                        165                 170                 175

Ala Ser Gly Phe Asn Ile Lys Asp Thr Tyr Ile His Trp Val Lys Gln
                        180                 185                 190

Arg Pro Glu Gln Gly Leu Glu Trp Ile Gly Arg Ile Asp Pro Ala Asn
                        195                 200                 205

Gly Asn Thr Lys Tyr Asp Pro Lys Phe Gln Gly Lys Ala Thr Ile Thr
                        210                 215                 220

Thr Asp Thr Ser Phe Asn Thr Ala Tyr Leu Gln Leu Ser Ser Leu Thr
            225                 230                 235                 240

Ser Glu Asp Thr Ala Val Tyr Tyr Cys Ala Lys Val Gly Tyr Gly His
                        245                 250                 255

Trp Tyr Phe Asp Val Trp Gly Ala Gly Thr Thr Val Thr Val Ser Ser
                        260                 265                 270

Val Asp Leu Gly Gly Gly Gly Ser Gly Gly Gly Gly Ser Gly Gly Gly
                        275                 280                 285

Gly Ser Ile Gly Val Ser Val Leu Ser Val Leu Val Val Ser Val Val
                        290                 295                 300

Ala Val Leu Val Tyr Lys Phe Tyr Phe His Leu Met Leu Leu Ala Gly
            305                 310                 315                 320

Cys Ile Lys Tyr Gly Arg Gly Glu Asn Ile Tyr Asp Ala Phe Val Ile
                        325                 330                 335

Tyr Ser Ser Gln Asp Glu Asp Trp Val Arg Asn Glu Leu Val Lys Asn
                        340                 345                 350

Leu Glu Glu Gly Val Pro Pro Phe Gln Leu Cys Leu His Tyr Arg Asp
                        355                 360                 365

Phe Ile Pro Gly Val Ala Ile Ala Ala Asn Ile His Glu Gly Phe
                        370                 375                 380

His Lys Ser Arg Lys Val Ile Val Val Ser Gln His Phe Ile Gln
            385                 390                 395                 400

Ser Arg Trp Cys Ile Phe Glu Tyr Glu Ile Ala Gln Thr Trp Gln Phe
                        405                 410                 415

Leu Ser Ser Arg Ala Gly Ile Ile Phe Ile Val Leu Gln Lys Val Glu
                        420                 425                 430

Lys Thr Leu Leu Arg Gln Gln Val Glu Leu Tyr Arg Leu Leu Ser Arg
                        435                 440                 445

Asn Thr Tyr Leu Glu Trp Glu Asp Ser Val Leu Gly Arg His Ile Phe
                        450                 455                 460

Trp Arg Arg Leu Arg Lys Ala Leu Leu Asp Gly Lys Ser Trp Asn Pro
            465                 470                 475                 480

Glu Gly Thr Val Gly Thr Gly Cys Asn Trp Gln Glu Ala Thr Ser Ile
                        485                 490                 495

<210> SEQ ID NO 36
<211> LENGTH: 500
```

```
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<220> FEATURE:
<221> NAME/KEY: MISC_FEATURE
<222> LOCATION: (19)..(275)
<223> OTHER INFORMATION: TK1-ScFv
<220> FEATURE:
<221> NAME/KEY: MISC_FEATURE
<222> LOCATION: (276)..(290)
<223> OTHER INFORMATION: GS-Linker
<220> FEATURE:
<221> NAME/KEY: MISC_FEATURE
<222> LOCATION: (291)..(295)
<223> OTHER INFORMATION: LRR Short Hinge
<220> FEATURE:
<221> NAME/KEY: MISC_FEATURE
<222> LOCATION: (296)..(318)
<223> OTHER INFORMATION: TLR4 transmembrane domain
<220> FEATURE:
<221> NAME/KEY: MISC_FEATURE
<222> LOCATION: (319)..(500)
<223> OTHER INFORMATION: TLR4 cytosolic domain

<400> SEQUENCE: 36
```

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser

```
                260                 265                 270
Val Asp Leu Gly Gly Gly Ser Gly Gly Gly Ser Gly Gly Gly
            275                 280                 285

Gly Ser Met Asn Lys Thr Ile Ile Gly Val Ser Val Leu Ser Val Leu
            290                 295                 300

Val Val Ser Val Val Ala Val Leu Val Tyr Lys Phe Tyr Phe His Leu
305                 310                 315                 320

Met Leu Leu Ala Gly Cys Ile Lys Tyr Gly Arg Gly Glu Asn Ile Tyr
                325                 330                 335

Asp Ala Phe Val Ile Tyr Ser Ser Gln Asp Glu Asp Trp Val Arg Asn
            340                 345                 350

Glu Leu Val Lys Asn Leu Glu Glu Gly Val Pro Pro Phe Gln Leu Cys
            355                 360                 365

Leu His Tyr Arg Asp Phe Ile Pro Gly Val Ala Ile Ala Ala Asn Ile
            370                 375                 380

Ile His Glu Gly Phe His Lys Ser Arg Lys Val Ile Val Val Val Ser
385                 390                 395                 400

Gln His Phe Ile Gln Ser Arg Trp Cys Ile Phe Glu Tyr Glu Ile Ala
                405                 410                 415

Gln Thr Trp Gln Phe Leu Ser Ser Arg Ala Gly Ile Ile Phe Ile Val
            420                 425                 430

Leu Gln Lys Val Glu Lys Thr Leu Leu Arg Gln Gln Val Glu Leu Tyr
            435                 440                 445

Arg Leu Leu Ser Arg Asn Thr Tyr Leu Glu Trp Glu Asp Ser Val Leu
            450                 455                 460

Gly Arg His Ile Phe Trp Arg Arg Leu Arg Lys Ala Leu Leu Asp Gly
465                 470                 475                 480

Lys Ser Trp Asn Pro Glu Gly Thr Val Gly Thr Gly Cys Asn Trp Gln
                485                 490                 495

Glu Ala Thr Ser
            500

<210> SEQ ID NO 37
<211> LENGTH: 551
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Singal peptide
<220> FEATURE:
<221> NAME/KEY: MISC_FEATURE
<222> LOCATION: (19)..(275)
<223> OTHER INFORMATION: TK1-ScFv
<220> FEATURE:
<221> NAME/KEY: MISC_FEATURE
<222> LOCATION: (269)..(551)
<223> OTHER INFORMATION: TLR4 cytosolic domain
<220> FEATURE:
<221> NAME/KEY: MISC_FEATURE
<222> LOCATION: (276)..(290)
<223> OTHER INFORMATION: GS-Linker
<220> FEATURE:
<221> NAME/KEY: MISC_FEATURE
<222> LOCATION: (291)..(345)
<223> OTHER INFORMATION: LRR long hinge
<220> FEATURE:
<221> NAME/KEY: MISC_FEATURE
<222> LOCATION: (346)..(368)
<223> OTHER INFORMATION: TLR4 transmembrane domain
```

```
<400> SEQUENCE: 37

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Ser Gly Gly Gly Ser Gly Gly Gly
        275                 280                 285

Gly Ser Asn Asp Phe Ala Cys Thr Cys Glu His Gln Ser Phe Leu Gln
    290                 295                 300

Trp Ile Lys Asp Gln Arg Gln Leu Leu Val Glu Val Glu Arg Met Glu
305                 310                 315                 320

Cys Ala Thr Pro Ser Asp Lys Gln Gly Met Pro Val Leu Ser Leu Asn
                325                 330                 335

Ile Thr Cys Gln Met Asn Lys Thr Ile Ile Gly Val Ser Val Leu Ser
            340                 345                 350

Val Leu Val Val Ser Val Val Ala Val Leu Val Tyr Lys Phe Tyr Phe
        355                 360                 365

His Leu Met Leu Leu Ala Gly Cys Ile Lys Tyr Gly Arg Gly Glu Asn
370                 375                 380

Ile Tyr Asp Ala Phe Val Ile Tyr Ser Ser Gln Asp Glu Asp Trp Val
385                 390                 395                 400

Arg Asn Glu Leu Val Lys Asn Leu Glu Glu Gly Val Pro Pro Phe Gln
                405                 410                 415
```

```
Leu Cys Leu His Tyr Arg Asp Phe Ile Pro Gly Val Ala Ile Ala Ala
                420                 425                 430

Asn Ile Ile His Glu Gly Phe His Lys Ser Arg Lys Val Ile Val Val
                435                 440                 445

Val Ser Gln His Phe Ile Gln Ser Arg Trp Cys Ile Phe Glu Tyr Glu
            450                 455                 460

Ile Ala Gln Thr Trp Gln Phe Leu Ser Ser Arg Ala Gly Ile Ile Phe
465                 470                 475                 480

Ile Val Leu Gln Lys Val Glu Lys Thr Leu Leu Arg Gln Gln Val Glu
                485                 490                 495

Leu Tyr Arg Leu Leu Ser Arg Asn Thr Tyr Leu Glu Trp Glu Asp Ser
                500                 505                 510

Val Leu Gly Arg His Ile Phe Trp Arg Arg Leu Arg Lys Ala Leu Leu
                515                 520                 525

Asp Gly Lys Ser Trp Asn Pro Glu Gly Thr Val Gly Thr Gly Cys Asn
                530                 535                 540

Trp Gln Glu Ala Thr Ser Ile
545                 550

<210> SEQ ID NO 38
<211> LENGTH: 508
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(302)
<223> OTHER INFORMATION: IgG4 short hinge
<220> FEATURE:
<221> NAME/KEY: MISC_FEATURE
<222> LOCATION: (303)..(325)
<223> OTHER INFORMATION: TLR4 transmembrane domain
<220> FEATURE:
<221> NAME/KEY: MISC_FEATURE
<222> LOCATION: (326)..(508)
<223> OTHER INFORMATION: TLR4 cytosolic domain

<400> SEQUENCE: 38

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
                20                  25                  30

Leu Ser Ala Ser Pro Gly Glu Lys Val Thr Met Thr Cys Arg Ala Ser
            35                  40                  45

Ser Ser Val Ser Tyr Met His Phe Tyr Gln Gln Lys Pro Gly Ser Ser
        50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95
```

-continued

```
Ser Arg Val Glu Ala Glu Asp Ala Ala Thr Tyr Tyr Cys Gln Gln Trp
             100                 105                 110

Ser Ser Asn Pro Pro Thr Phe Gly Ser Gly Thr Lys Leu Glu Ile Lys
             115                 120                 125

Ser Gly Gly Gly Gly Ser Gly Gly Gly Gly Ser Gly Gly Gly Gly Ser
             130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                 165                 170                 175

Ala Ser Gly Phe Asn Ile Lys Asp Thr Tyr Ile His Trp Val Lys Gln
             180                 185                 190

Arg Pro Glu Gln Gly Leu Glu Trp Ile Gly Arg Ile Asp Pro Ala Asn
             195                 200                 205

Gly Asn Thr Lys Tyr Asp Pro Lys Phe Gln Gly Lys Ala Thr Ile Thr
             210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                 245                 250                 255

Trp Tyr Phe Asp Val Trp Gly Ala Gly Thr Thr Val Thr Val Ser Ser
             260                 265                 270

Val Asp Leu Gly Gly Gly Gly Ser Gly Gly Gly Gly Ser Gly Gly Gly
             275                 280                 285

Gly Ser Glu Ser Lys Tyr Gly Pro Pro Cys Pro Pro Cys Pro Ile Gly
             290                 295                 300

Val Ser Val Leu Ser Val Leu Val Val Ser Val Ala Val Leu Val Val
305                 310                 315                 320

Tyr Lys Phe Tyr Phe His Leu Met Leu Leu Ala Gly Cys Ile Lys Tyr
                 325                 330                 335

Gly Arg Gly Glu Asn Ile Tyr Asp Ala Phe Val Ile Tyr Ser Ser Gln
             340                 345                 350

Asp Glu Asp Trp Val Arg Asn Glu Leu Val Lys Asn Leu Glu Glu Gly
             355                 360                 365

Val Pro Pro Phe Gln Leu Cys Leu His Tyr Arg Asp Phe Ile Pro Gly
370                 375                 380

Val Ala Ile Ala Ala Asn Ile Ile His Glu Gly Phe His Lys Ser Arg
385                 390                 395                 400

Lys Val Ile Val Val Ser Gln His Phe Ile Gln Ser Arg Trp Cys
                 405                 410                 415

Ile Phe Glu Tyr Glu Ile Ala Gln Thr Trp Gln Phe Leu Ser Ser Arg
             420                 425                 430

Ala Gly Ile Ile Phe Ile Val Leu Gln Lys Val Glu Lys Thr Leu Leu
             435                 440                 445

Arg Gln Gln Val Glu Leu Tyr Arg Leu Leu Ser Arg Asn Thr Tyr Leu
             450                 455                 460

Glu Trp Glu Asp Ser Val Leu Gly Arg His Ile Phe Trp Arg Arg Leu
465                 470                 475                 480

Arg Lys Ala Leu Leu Asp Gly Lys Ser Trp Asn Pro Glu Gly Thr Val
                 485                 490                 495

Gly Thr Gly Cys Asn Trp Gln Glu Ala Thr Ser Ile
             500                 505
```

-continued

```
<210> SEQ ID NO 39
<211> LENGTH: 615
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(409)
<223> OTHER INFORMATION: IgG4 medium hinge
<220> FEATURE:
<221> NAME/KEY: MISC_FEATURE
<222> LOCATION: (410)..(432)
<223> OTHER INFORMATION: TLR4 transmembrane domain
<220> FEATURE:
<221> NAME/KEY: MISC_FEATURE
<222> LOCATION: (433)..(615)
<223> OTHER INFORMATION: TLR4 cytosolic domain

<400> SEQUENCE: 39

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
```

```
                245                 250                 255
Trp Tyr Phe Asp Val Trp Gly Ala Gly Thr Thr Val Thr Val Ser Ser
            260                 265                 270
Val Asp Leu Gly Gly Gly Gly Ser Gly Gly Gly Gly Ser Gly Gly Gly
        275                 280                 285
Gly Ser Glu Ser Lys Tyr Gly Pro Pro Cys Pro Pro Cys Pro Gly Gln
    290                 295                 300
Pro Arg Glu Pro Gln Val Tyr Thr Leu Pro Pro Ser Gln Glu Glu Met
305                 310                 315                 320
Thr Lys Asn Gln Val Ser Leu Thr Cys Leu Val Lys Gly Phe Tyr Pro
                325                 330                 335
Ser Asp Ile Ala Val Glu Trp Glu Ser Asn Gly Gln Pro Glu Asn Asn
            340                 345                 350
Tyr Lys Thr Thr Pro Pro Val Leu Asp Ser Asp Gly Ser Phe Phe Leu
        355                 360                 365
Tyr Ser Arg Leu Thr Val Asp Lys Ser Arg Trp Gln Glu Gly Asn Val
    370                 375                 380
Phe Ser Cys Ser Val Met His Glu Ala Leu His Asn His Tyr Thr Gln
385                 390                 395                 400
Lys Ser Leu Ser Leu Ser Leu Gly Lys Ile Gly Val Ser Val Leu Ser
                405                 410                 415
Val Leu Val Val Ser Val Ala Val Leu Val Tyr Lys Phe Tyr Phe
            420                 425                 430
His Leu Met Leu Leu Ala Gly Cys Ile Lys Tyr Gly Arg Gly Glu Asn
        435                 440                 445
Ile Tyr Asp Ala Phe Val Ile Tyr Ser Ser Gln Asp Glu Asp Trp Val
    450                 455                 460
Arg Asn Glu Leu Val Lys Asn Leu Glu Glu Gly Val Pro Pro Phe Gln
465                 470                 475                 480
Leu Cys Leu His Tyr Arg Asp Phe Ile Pro Gly Val Ala Ile Ala Ala
                485                 490                 495
Asn Ile Ile His Glu Gly Phe His Lys Ser Arg Lys Val Ile Val Val
            500                 505                 510
Val Ser Gln His Phe Ile Gln Ser Arg Trp Cys Ile Phe Glu Tyr Glu
        515                 520                 525
Ile Ala Gln Thr Trp Gln Phe Leu Ser Ser Arg Ala Gly Ile Ile Phe
    530                 535                 540
Ile Val Leu Gln Lys Val Glu Lys Thr Leu Leu Arg Gln Gln Val Glu
545                 550                 555                 560
Leu Tyr Arg Leu Leu Ser Arg Asn Thr Tyr Leu Glu Trp Glu Asp Ser
                565                 570                 575
Val Leu Gly Arg His Ile Phe Trp Arg Arg Leu Arg Lys Ala Leu Leu
            580                 585                 590
Asp Gly Lys Ser Trp Asn Pro Glu Gly Thr Val Gly Thr Gly Cys Asn
        595                 600                 605
Trp Gln Glu Ala Thr Ser Ile
    610                 615

<210> SEQ ID NO 40
<211> LENGTH: 724
<212> TYPE: PRT
<213> ORGANISM: Artificial Sequence
<220> FEATURE:
<223> OTHER INFORMATION: Chimeric antigen receptor
<220> FEATURE:
```

```
<221> NAME/KEY: SIGNAL
<222> LOCATION: (1)..(18)
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(518)
<223> OTHER INFORMATION: IgG4 long hinge
<220> FEATURE:
<221> NAME/KEY: MISC_FEATURE
<222> LOCATION: (519)..(541)
<223> OTHER INFORMATION: TLR4 transmembrane domain
<220> FEATURE:
<221> NAME/KEY: MISC_FEATURE
<222> LOCATION: (542)..(724)
<223> OTHER INFORMATION: TLR4 cytosolic domain

<400> SEQUENCE: 40
```

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Ser Gly Gly Gly Ser Gly Gly Gly
        275                 280                 285

```
Gly Ser Glu Ser Lys Tyr Gly Pro Cys Pro Cys Pro Ala Pro
290                 295             300

Pro Val Ala Gly Pro Ser Val Phe Leu Phe Pro Pro Lys Pro Lys Asp
305                 310             315                 320

Thr Leu Met Ile Ser Arg Thr Pro Glu Val Thr Cys Val Val Val Asp
                325             330              335

Val Ser Gln Glu Asp Pro Glu Val Gln Phe Asn Trp Tyr Val Asp Gly
            340             345             350

Val Glu Val His Asn Ala Lys Thr Lys Pro Arg Glu Glu Gln Phe Gln
                355             360             365

Ser Thr Tyr Arg Val Val Ser Val Leu Thr Val Leu His Gln Asp Trp
370             375             380

Leu Asn Gly Lys Glu Tyr Lys Cys Lys Val Ser Asn Lys Gly Leu Pro
385             390             395             400

Ser Ser Ile Glu Lys Thr Ile Ser Lys Ala Lys Gly Gln Pro Arg Glu
                405             410             415

Pro Gln Val Tyr Thr Leu Pro Pro Ser Gln Glu Glu Met Thr Lys Asn
            420             425             430

Gln Val Ser Leu Thr Cys Leu Val Lys Gly Phe Tyr Pro Ser Asp Ile
                435             440             445

Ala Val Glu Trp Glu Ser Asn Gly Gln Pro Glu Asn Asn Tyr Lys Thr
450             455             460

Thr Pro Pro Val Leu Asp Ser Asp Gly Ser Phe Phe Leu Tyr Ser Arg
465             470             475             480

Leu Thr Val Asp Lys Ser Arg Trp Gln Glu Gly Asn Val Phe Ser Cys
                485             490             495

Ser Val Met His Glu Ala Leu His Asn His Tyr Thr Gln Lys Ser Leu
            500             505             510

Ser Leu Ser Leu Gly Lys Ile Gly Val Ser Val Leu Ser Val Leu Val
            515             520             525

Val Ser Val Val Ala Val Leu Val Tyr Lys Phe Tyr Phe His Leu Met
530             535             540

Leu Leu Ala Gly Cys Ile Lys Tyr Gly Arg Gly Glu Asn Ile Tyr Asp
545             550             555             560

Ala Phe Val Ile Tyr Ser Ser Gln Asp Glu Asp Trp Val Arg Asn Glu
                565             570             575

Leu Val Lys Asn Leu Glu Glu Gly Val Pro Pro Phe Gln Leu Cys Leu
            580             585             590

His Tyr Arg Asp Phe Ile Pro Gly Val Ala Ile Ala Ala Asn Ile Ile
        595             600             605

His Glu Gly Phe His Lys Ser Arg Lys Val Ile Val Val Val Ser Gln
        610             615             620

His Phe Ile Gln Ser Arg Trp Cys Ile Phe Glu Tyr Glu Ile Ala Gln
625             630             635             640

Thr Trp Gln Phe Leu Ser Ser Arg Ala Gly Ile Phe Ile Val Leu
            645             650             655

Gln Lys Val Glu Lys Thr Leu Leu Arg Gln Gln Val Glu Leu Tyr Arg
                660             665             670

Leu Leu Ser Arg Asn Thr Tyr Leu Glu Trp Glu Asp Ser Val Leu Gly
            675             680             685

Arg His Ile Phe Trp Arg Arg Leu Arg Lys Ala Leu Leu Asp Gly Lys
690             695             700

Ser Trp Asn Pro Glu Gly Thr Val Gly Thr Gly Cys Asn Trp Gln Glu
```

```
705                 710                 715                 720

Ala Thr Ser Ile

<210> SEQ ID NO 41
<211> LENGTH: 564
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<220> FEATURE:
<221> NAME/KEY: MISC_FEATURE
<222> LOCATION: (276)..(290)
<223> OTHER INFORMATION: GS linkder
<220> FEATURE:
<221> NAME/KEY: MISC_FEATURE
<222> LOCATION: (291)..(358)
<223> OTHER INFORMATION: Mutated CD8 hinge
<220> FEATURE:
<221> NAME/KEY: MISC_FEATURE
<222> LOCATION: (359)..(381)
<223> OTHER INFORMATION: TLR4 transmembrane domain
<220> FEATURE:
<221> NAME/KEY: MISC_FEATURE
<222> LOCATION: (382)..(564)
<223> OTHER INFORMATION: TLR4 cytosolic domain

<400> SEQUENCE: 41

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220
```

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
            245                 250                 255

Trp Tyr Phe Asp Val Trp Gly Ala Gly Thr Thr Val Thr Val Ser Ser
            260                 265                 270

Val Asp Leu Gly Gly Gly Ser Gly Gly Gly Ser Gly Gly Gly
            275                 280                 285

Gly Ser Ser Ala Leu Ser Asn Ser Ile Met Tyr Phe Ser His Phe Val
290                 295                 300

Pro Val Phe Leu Pro Ala Lys Pro Thr Thr Thr Pro Ala Pro Arg Pro
305                 310                 315                 320

Pro Thr Pro Ala Pro Thr Ile Ala Ser Gln Pro Leu Ser Leu Arg Pro
            325                 330                 335

Glu Ala Ser Arg Pro Ala Ala Gly Gly Ala Val His Thr Arg Gly Leu
            340                 345                 350

Asp Phe Ala Ser Asp Ile Ile Gly Val Ser Val Leu Ser Val Leu Val
            355                 360                 365

Val Ser Val Val Ala Val Leu Val Tyr Lys Phe Tyr Phe His Leu Met
370                 375                 380

Leu Leu Ala Gly Cys Ile Lys Tyr Gly Arg Gly Glu Asn Ile Tyr Asp
385                 390                 395                 400

Ala Phe Val Ile Tyr Ser Ser Gln Asp Glu Asp Trp Val Arg Asn Glu
            405                 410                 415

Leu Val Lys Asn Leu Glu Glu Gly Val Pro Pro Phe Gln Leu Cys Leu
            420                 425                 430

His Tyr Arg Asp Phe Ile Pro Gly Val Ala Ile Ala Ala Asn Ile Ile
            435                 440                 445

His Glu Gly Phe His Lys Ser Arg Lys Val Ile Val Val Ser Gln
450                 455                 460

His Phe Ile Gln Ser Arg Trp Cys Ile Phe Glu Tyr Glu Ile Ala Gln
465                 470                 475                 480

Thr Trp Gln Phe Leu Ser Ser Arg Ala Gly Ile Ile Phe Ile Val Leu
            485                 490                 495

Gln Lys Val Glu Lys Thr Leu Leu Arg Gln Gln Val Glu Leu Tyr Arg
            500                 505                 510

Leu Leu Ser Arg Asn Thr Tyr Leu Glu Trp Glu Asp Ser Val Leu Gly
            515                 520                 525

Arg His Ile Phe Trp Arg Arg Leu Arg Lys Ala Leu Leu Asp Gly Lys
530                 535                 540

Ser Trp Asn Pro Glu Gly Thr Val Gly Thr Gly Cys Asn Trp Gln Glu
545                 550                 555                 560

Ala Thr Ser Ile

<210> SEQ ID NO 42
<211> LENGTH: 564
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Sginal peptide
<220> FEATURE:
<221> NAME/KEY: MISC_FEATURE
<222> LOCATION: (19)..(275)

```
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(358)
<223> OTHER INFORMATION: GS linker
<220> FEATURE:
<221> NAME/KEY: MISC_FEATURE
<222> LOCATION: (359)..(381)
<223> OTHER INFORMATION: TLR4 transmembrane domain
<220> FEATURE:
<221> NAME/KEY: MISC_FEATURE
<222> LOCATION: (382)..(564)
<223> OTHER INFORMATION: TLR4 cytosolic domain

<400> SEQUENCE: 42
```

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Gly Ser Gly Gly Gly Gly Ser Gly Gly Gly
        275                 280                 285

Gly Ser Ser Ala Leu Ser Asn Ser Ile Met Tyr Phe Ser His Phe Val
    290                 295                 300

Pro Val Phe Leu Pro Ala Lys Pro Thr Thr Thr Pro Ala Pro Arg Pro
305                 310                 315                 320

Pro Thr Pro Ala Pro Thr Ile Ala Ser Gln Pro Leu Ser Leu Arg Pro
            325                 330                 335

Glu Ala Cys Arg Pro Ala Ala Gly Gly Ala Val His Thr Arg Gly Leu
        340                 345                 350

Asp Phe Ala Cys Asp Ile Ile Gly Val Ser Val Leu Ser Val Leu Val
            355                 360                 365

Val Ser Val Val Ala Val Leu Val Tyr Lys Phe Tyr Phe His Leu Met
370                 375                 380

Leu Leu Ala Gly Cys Ile Lys Tyr Gly Arg Gly Glu Asn Ile Tyr Asp
385                 390                 395                 400

Ala Phe Val Ile Tyr Ser Ser Gln Asp Glu Asp Trp Val Arg Asn Glu
            405                 410                 415

Leu Val Lys Asn Leu Glu Glu Gly Val Pro Pro Phe Gln Leu Cys Leu
        420                 425                 430

His Tyr Arg Asp Phe Ile Pro Gly Val Ala Ile Ala Ala Asn Ile Ile
            435                 440                 445

His Glu Gly Phe His Lys Ser Arg Lys Val Ile Val Val Val Ser Gln
        450                 455                 460

His Phe Ile Gln Ser Arg Trp Cys Ile Phe Glu Tyr Glu Ile Ala Gln
465                 470                 475                 480

Thr Trp Gln Phe Leu Ser Ser Arg Ala Gly Ile Ile Phe Ile Val Leu
            485                 490                 495

Gln Lys Val Glu Lys Thr Leu Leu Arg Gln Gln Val Glu Leu Tyr Arg
        500                 505                 510

Leu Leu Ser Arg Asn Thr Tyr Leu Glu Trp Glu Asp Ser Val Leu Gly
            515                 520                 525

Arg His Ile Phe Trp Arg Arg Leu Arg Lys Ala Leu Leu Asp Gly Lys
        530                 535                 540

Ser Trp Asn Pro Glu Gly Thr Val Gly Thr Gly Cys Asn Trp Gln Glu
545                 550                 555                 560

Ala Thr Ser Ile

<210> SEQ ID NO 43
<211> LENGTH: 378
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(311)
<223> OTHER INFORMATION: FCGR3A transmembrane domain
<220> FEATURE:
<221> NAME/KEY: MISC_FEATURE
<222> LOCATION: (312)..(336)
<223> OTHER INFORMATION: FCGR3A cytosolic domain
<220> FEATURE:
<221> NAME/KEY: MISC_FEATURE
<222> LOCATION: (337)..(378)
<223> OTHER INFORMATION: FCER1G cytosolic domain

<400> SEQUENCE: 43

```
Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Gly Ser Gly Gly Gly Gly Ser Gly Gly Gly
        275                 280                 285

Gly Ser Val Ser Phe Cys Leu Val Met Val Leu Leu Phe Ala Val Asp
    290                 295                 300

Thr Gly Leu Tyr Phe Ser Val Lys Thr Asn Ile Arg Ser Ser Thr Arg
305                 310                 315                 320

Asp Trp Lys Asp His Lys Phe Lys Trp Arg Lys Asp Pro Gln Asp Lys
                325                 330                 335

Arg Leu Lys Ile Gln Val Arg Lys Ala Ala Ile Thr Ser Tyr Glu Lys
            340                 345                 350

Ser Asp Gly Val Tyr Thr Gly Leu Ser Thr Arg Asn Gln Glu Thr Tyr
        355                 360                 365

Glu Thr Leu Lys His Glu Lys Pro Pro Gln
    370                 375
```

<210> SEQ ID NO 44
<211> LENGTH: 446
<212> TYPE: PRT

-continued

```
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(358)
<223> OTHER INFORMATION: Modified CD8a linker
<220> FEATURE:
<221> NAME/KEY: MISC_FEATURE
<222> LOCATION: (359)..(379)
<223> OTHER INFORMATION: FCGR3A transmembrane domain
<220> FEATURE:
<221> NAME/KEY: MISC_FEATURE
<222> LOCATION: (380)..(404)
<223> OTHER INFORMATION: FCGR3A cytosolic domain
<220> FEATURE:
<221> NAME/KEY: MISC_FEATURE
<222> LOCATION: (405)..(446)
<223> OTHER INFORMATION: FCER1G cytosolic domain

<400> SEQUENCE: 44

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
```

```
                    245                 250                 255

Trp Tyr Phe Asp Val Trp Gly Ala Gly Thr Thr Val Thr Val Ser Ser
                260                 265                 270

Val Asp Leu Gly Gly Gly Gly Ser Gly Gly Gly Gly Ser Gly Gly Gly
            275                 280                 285

Gly Ser Ser Ala Leu Ser Asn Ser Ile Met Tyr Phe Ser His Phe Val
        290                 295                 300

Pro Val Phe Leu Pro Ala Lys Pro Thr Thr Thr Pro Ala Pro Arg Pro
305                 310                 315                 320

Pro Thr Pro Ala Pro Thr Ile Ala Ser Gln Pro Leu Ser Leu Arg Pro
                325                 330                 335

Glu Ala Ser Arg Pro Ala Ala Gly Gly Ala Val His Thr Arg Gly Leu
            340                 345                 350

Asp Phe Ala Ser Asp Ile Val Ser Phe Cys Leu Val Met Val Leu Leu
        355                 360                 365

Phe Ala Val Asp Thr Gly Leu Tyr Phe Ser Val Lys Thr Asn Ile Arg
    370                 375                 380

Ser Ser Thr Arg Asp Trp Lys Asp His Lys Phe Lys Trp Arg Lys Asp
385                 390                 395                 400

Pro Gln Asp Lys Arg Leu Lys Ile Gln Val Arg Lys Ala Ala Ile Thr
                405                 410                 415

Ser Tyr Glu Lys Ser Asp Gly Val Tyr Thr Gly Leu Ser Thr Arg Asn
            420                 425                 430

Gln Glu Thr Tyr Glu Thr Leu Lys His Glu Lys Pro Pro Gln
        435                 440                 445

<210> SEQ ID NO 45
<211> LENGTH: 446
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(358)
<223> OTHER INFORMATION: Portion of CD8 hinge
<220> FEATURE:
<221> NAME/KEY: MISC_FEATURE
<222> LOCATION: (359)..(379)
<223> OTHER INFORMATION: FCGR3A transmembrane domain
<220> FEATURE:
<221> NAME/KEY: MISC_FEATURE
<222> LOCATION: (380)..(404)
<223> OTHER INFORMATION: FCGR3A cytosolic domain
<220> FEATURE:
<221> NAME/KEY: MISC_FEATURE
<222> LOCATION: (405)..(446)
<223> OTHER INFORMATION: FCER1G cytosolic domain

<400> SEQUENCE: 45

Met Asp Phe Gln Val Gln Ile Ile Ser Phe Leu Leu Ile Ser Ala Ser
1               5                   10                  15
```

```
Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Gly Ser Gly Gly Gly Gly Ser Gly Gly Gly
        275                 280                 285

Gly Ser Ser Ala Leu Ser Asn Ser Ile Met Tyr Phe Ser His Phe Val
    290                 295                 300

Pro Val Phe Leu Pro Ala Lys Pro Thr Thr Thr Pro Ala Pro Arg Pro
305                 310                 315                 320

Pro Thr Pro Ala Pro Thr Ile Ala Ser Gln Pro Leu Ser Leu Arg Pro
                325                 330                 335

Glu Ala Cys Arg Pro Ala Ala Gly Gly Ala Val His Thr Arg Gly Leu
            340                 345                 350

Asp Phe Ala Cys Asp Ile Val Ser Phe Cys Leu Val Met Val Leu Leu
        355                 360                 365

Phe Ala Val Asp Thr Gly Leu Tyr Phe Ser Val Lys Thr Asn Ile Arg
    370                 375                 380

Ser Ser Thr Arg Asp Trp Lys Asp His Lys Phe Lys Trp Arg Lys Asp
385                 390                 395                 400

Pro Gln Asp Lys Arg Leu Lys Ile Gln Val Arg Lys Ala Ala Ile Thr
                405                 410                 415

Ser Tyr Glu Lys Ser Asp Gly Val Tyr Thr Gly Leu Ser Thr Arg Asn
            420                 425                 430

Gln Glu Thr Tyr Glu Thr Leu Lys His Glu Lys Pro Pro Gln
```

<210> SEQ ID NO 46
<211> LENGTH: 391
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(303)
<223> OTHER INFORMATION: IgG4 short hinge
<220> FEATURE:
<221> NAME/KEY: MISC_FEATURE
<222> LOCATION: (304)..(324)
<223> OTHER INFORMATION: FCGR3A transmembrane domain
<220> FEATURE:
<221> NAME/KEY: MISC_FEATURE
<222> LOCATION: (325)..(349)
<223> OTHER INFORMATION: FCGR3A cytosolic domain
<220> FEATURE:
<221> NAME/KEY: MISC_FEATURE
<222> LOCATION: (350)..(391)
<223> OTHER INFORMATION: FCER1G cytosolic domain

<400> SEQUENCE: 46

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

-continued

```
Gly Asn Thr Lys Tyr Asp Pro Lys Phe Gln Gly Lys Ala Thr Ile Thr
            210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Gly Ser Gly Gly Gly Gly Ser Gly Gly Gly
        275                 280                 285

Gly Ser Glu Ser Lys Tyr Gly Pro Pro Cys Pro Pro Cys Pro Ile Val
290                 295                 300

Ser Phe Cys Leu Val Met Val Leu Leu Phe Ala Val Asp Thr Gly Leu
305                 310                 315                 320

Tyr Phe Ser Val Lys Thr Asn Ile Arg Ser Ser Thr Arg Asp Trp Lys
                325                 330                 335

Asp His Lys Phe Lys Trp Arg Lys Asp Pro Gln Asp Lys Arg Leu Lys
            340                 345                 350

Ile Gln Val Arg Lys Ala Ala Ile Thr Ser Tyr Glu Lys Ser Asp Gly
        355                 360                 365

Val Tyr Thr Gly Leu Ser Thr Arg Asn Gln Glu Thr Tyr Glu Thr Leu
370                 375                 380

Lys His Glu Lys Pro Pro Gln
385                 390
```

```
<210> SEQ ID NO 47
<211> LENGTH: 497
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linkder
<220> FEATURE:
<221> NAME/KEY: MISC_FEATURE
<222> LOCATION: (291)..(409)
<223> OTHER INFORMATION: IgG4 119 aa hinge
<220> FEATURE:
<221> NAME/KEY: MISC_FEATURE
<222> LOCATION: (410)..(430)
<223> OTHER INFORMATION: FCGR3A transmembrane domain
<220> FEATURE:
<221> NAME/KEY: MISC_FEATURE
<222> LOCATION: (431)..(455)
<223> OTHER INFORMATION: FCGR3A cytosolic domain
<220> FEATURE:
<221> NAME/KEY: MISC_FEATURE
<222> LOCATION: (456)..(497)
<223> OTHER INFORMATION: FCER1G cytosolic domain

<400> SEQUENCE: 47

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30
```

```
Leu Ser Ala Ser Pro Gly Glu Lys Val Thr Met Thr Cys Arg Ala Ser
                35                  40                  45

Ser Ser Val Ser Tyr Met His Phe Tyr Gln Gln Lys Pro Gly Ser Ser
     50                  55                  60

Pro Lys Pro Trp Ile Tyr Ala Thr Ser Asn Leu Ala Ser Gly Val Pro
 65                  70                  75                  80

Ala Arg Phe Ser Gly Ser Gly Ser Gly Thr Ser Phe Ser Leu Thr Ile
                 85                  90                  95

Ser Arg Val Glu Ala Glu Asp Ala Ala Thr Tyr Tyr Cys Gln Gln Trp
                100                 105                 110

Ser Ser Asn Pro Pro Thr Phe Gly Ser Gly Thr Lys Leu Glu Ile Lys
                115                 120                 125

Ser Gly Gly Gly Gly Ser Gly Gly Gly Gly Ser Gly Gly Gly Gly Ser
                130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
                180                 185                 190

Arg Pro Glu Gln Gly Leu Glu Trp Ile Gly Arg Ile Asp Pro Ala Asn
                195                 200                 205

Gly Asn Thr Lys Tyr Asp Pro Lys Phe Gln Gly Lys Ala Thr Ile Thr
                210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
                260                 265                 270

Val Asp Leu Gly Gly Gly Gly Ser Gly Gly Gly Gly Ser Gly Gly Gly
                275                 280                 285

Gly Ser Glu Ser Lys Tyr Gly Pro Pro Cys Pro Pro Cys Pro Gly Gln
                290                 295                 300

Pro Arg Glu Pro Gln Val Tyr Thr Leu Pro Pro Ser Gln Glu Glu Met
305                 310                 315                 320

Thr Lys Asn Gln Val Ser Leu Thr Cys Leu Val Lys Gly Phe Tyr Pro
                325                 330                 335

Ser Asp Ile Ala Val Glu Trp Glu Ser Asn Gly Gln Pro Glu Asn Asn
                340                 345                 350

Tyr Lys Thr Thr Pro Pro Val Leu Asp Ser Asp Gly Ser Phe Phe Leu
                355                 360                 365

Tyr Ser Arg Leu Thr Val Asp Lys Ser Arg Trp Gln Glu Gly Asn Val
                370                 375                 380

Phe Ser Cys Ser Val Met His Glu Ala Leu His Asn His Tyr Thr Gln
385                 390                 395                 400

Lys Ser Leu Ser Leu Ser Leu Gly Lys Val Ser Phe Cys Leu Val Met
                405                 410                 415

Val Leu Leu Phe Ala Val Asp Thr Gly Leu Tyr Phe Ser Val Lys Thr
                420                 425                 430

Asn Ile Arg Ser Ser Thr Arg Asp Trp Lys Asp His Lys Phe Lys Trp
                435                 440                 445
```

```
Arg Lys Asp Pro Gln Asp Lys Arg Leu Lys Ile Gln Val Arg Lys Ala
    450                 455                 460
Ala Ile Thr Ser Tyr Glu Lys Ser Asp Gly Val Tyr Thr Gly Leu Ser
465                 470                 475                 480
Thr Arg Asn Gln Glu Thr Tyr Glu Thr Leu Lys His Glu Lys Pro Pro
                485                 490                 495
Gln
```

<210> SEQ ID NO 48
<211> LENGTH: 607
<212> TYPE: PRT
<213> ORGANISM: Artificial Sequence
<220> FEATURE:
<223> OTHER INFORMATION: Chimeric angtigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(519)
<223> OTHER INFORMATION: IgG4 long hinge
<220> FEATURE:
<221> NAME/KEY: MISC_FEATURE
<222> LOCATION: (520)..(540)
<223> OTHER INFORMATION: FCGR3A transmembrane domain
<220> FEATURE:
<221> NAME/KEY: MISC_FEATURE
<222> LOCATION: (541)..(565)
<223> OTHER INFORMATION: FCGR3A cytosolic domain
<220> FEATURE:
<221> NAME/KEY: MISC_FEATURE
<222> LOCATION: (566)..(607)
<223> OTHER INFORMATION: FCER1G cytosolic domain

<400> SEQUENCE: 48

```
Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
                20                  25                  30

Leu Ser Ala Ser Pro Gly Glu Lys Val Thr Met Thr Cys Arg Ala Ser
            35                  40                  45

Ser Ser Val Ser Tyr Met His Phe Tyr Gln Gln Lys Pro Gly Ser Ser
        50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
                100                 105                 110

Ser Ser Asn Pro Pro Thr Phe Gly Ser Gly Thr Lys Leu Glu Ile Lys
            115                 120                 125

Ser Gly Gly Gly Gly Ser Gly Gly Gly Gly Ser Gly Gly Gly Gly Ser
        130                 135                 140

Met Ala Val Val Thr Gly Val Asn Ser Glu Val Gln Leu Gln Gln Ser
145                 150                 155                 160
```

-continued

Gly Ala Glu Leu Val Lys Pro Gly Ala Ser Val Lys Leu Ser Cys Thr
            165                 170                 175

Ala Ser Gly Phe Asn Ile Lys Asp Thr Tyr Ile His Trp Val Lys Gln
        180                 185                 190

Arg Pro Glu Gln Gly Leu Glu Trp Ile Gly Arg Ile Asp Pro Ala Asn
    195                 200                 205

Gly Asn Thr Lys Tyr Asp Pro Lys Phe Gln Gly Lys Ala Thr Ile Thr
210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Gly Ser Gly Gly Gly Ser Gly Gly Gly
        275                 280                 285

Gly Ser Glu Ser Lys Tyr Gly Pro Pro Cys Pro Pro Cys Pro Ala Pro
    290                 295                 300

Pro Val Ala Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser Gln Glu Asp Pro Glu Val Gln Phe Asn Trp Tyr Val Asp Gly
            340                 345                 350

Val Glu Val His Asn Ala Lys Thr Lys Pro Arg Glu Glu Gln Phe Gln
        355                 360                 365

Ser Thr Tyr Arg Val Val Ser Val Leu Thr Val Leu His Gln Asp Trp
    370                 375                 380

Leu Asn Gly Lys Glu Tyr Lys Cys Lys Val Ser Asn Lys Gly Leu Pro
385                 390                 395                 400

Ser Ser Ile Glu Lys Thr Ile Ser Lys Ala Lys Gly Gln Pro Arg Glu
                405                 410                 415

Pro Gln Val Tyr Thr Leu Pro Pro Ser Gln Glu Glu Met Thr Lys Asn
            420                 425                 430

Gln Val Ser Leu Thr Cys Leu Val Lys Gly Phe Tyr Pro Ser Asp Ile
        435                 440                 445

Ala Val Glu Trp Glu Ser Asn Gly Gln Pro Glu Asn Asn Tyr Lys Thr
    450                 455                 460

Thr Pro Pro Val Leu Asp Ser Asp Gly Ser Phe Phe Leu Tyr Ser Arg
465                 470                 475                 480

Leu Thr Val Asp Lys Ser Arg Trp Gln Glu Gly Asn Val Phe Ser Cys
                485                 490                 495

Ser Val Met His Glu Ala Leu His Asn His Tyr Thr Gln Lys Ser Leu
            500                 505                 510

Ser Leu Ser Leu Gly Lys Ile Val Ser Phe Cys Leu Val Met Val Leu
        515                 520                 525

Leu Phe Ala Val Asp Thr Gly Leu Tyr Phe Ser Val Lys Thr Asn Ile
    530                 535                 540

Arg Ser Ser Thr Arg Asp Trp Lys Asp His Lys Phe Lys Trp Arg Lys
545                 550                 555                 560

Asp Pro Gln Asp Lys Arg Leu Lys Ile Gln Val Arg Lys Ala Ala Ile
                565                 570                 575

Thr Ser Tyr Glu Lys Ser Asp Gly Val Tyr Thr Gly Leu Ser Thr Arg

```
                    580                 585                 590
Asn Gln Glu Thr Tyr Glu Thr Leu Lys His Glu Lys Pro Pro Gln
                595                 600                 605
```

<210> SEQ ID NO 49
<211> LENGTH: 390
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(312)
<223> OTHER INFORMATION: FCGR2A transmembrane domain
<220> FEATURE:
<221> NAME/KEY: MISC_FEATURE
<222> LOCATION: (313)..(390)
<223> OTHER INFORMATION: FCGR2A cytosolic domain

<400> SEQUENCE: 49

```
Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240
```

-continued

```
Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Gly Ser Gly Gly Gly Gly Ser Gly Gly Gly
        275                 280                 285

Gly Ser Ile Ile Val Ala Val Val Ala Thr Ala Val Ala Ala Ile
290                 295                 300

Val Ala Ala Val Val Ala Leu Ile Tyr Cys Arg Lys Lys Arg Ile Ser
305                 310                 315                 320

Ala Asn Ser Thr Asp Pro Val Lys Ala Ala Gln Phe Glu Pro Pro Gly
                325                 330                 335

Arg Gln Met Ile Ala Ile Arg Lys Arg Gln Leu Glu Glu Thr Asn Asn
            340                 345                 350

Asp Tyr Glu Thr Ala Asp Gly Gly Tyr Met Thr Leu Asn Pro Arg Ala
        355                 360                 365

Pro Thr Asp Asp Asp Lys Asn Ile Tyr Leu Thr Leu Pro Pro Asn Asp
    370                 375                 380

His Val Asn Ser Asn Asn
385                 390

<210> SEQ ID NO 50
<211> LENGTH: 458
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(358)
<223> OTHER INFORMATION: Modified CD8a hinge
<220> FEATURE:
<221> NAME/KEY: MISC_FEATURE
<222> LOCATION: (359)..(380)
<223> OTHER INFORMATION: FCGR2A transmembrane domain
<220> FEATURE:
<221> NAME/KEY: MISC_FEATURE
<222> LOCATION: (381)..(458)
<223> OTHER INFORMATION: FCGR2A cytosolic domain

<400> SEQUENCE: 50

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80
```

```
Ala Arg Phe Ser Gly Ser Gly Ser Gly Thr Ser Phe Ser Leu Thr Ile
            85                  90                  95

Ser Arg Val Glu Ala Glu Asp Ala Ala Thr Tyr Tyr Cys Gln Gln Trp
       100                 105                 110

Ser Ser Asn Pro Pro Thr Phe Gly Ser Gly Thr Lys Leu Glu Ile Lys
            115                 120                 125

Ser Gly Gly Gly Gly Ser Gly Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
            210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Ser Gly Gly Gly Ser Gly Gly Gly
        275                 280                 285

Gly Ser Ser Ala Leu Ser Asn Ser Ile Met Tyr Phe Ser His Phe Val
    290                 295                 300

Pro Val Phe Leu Pro Ala Lys Pro Thr Thr Thr Pro Ala Pro Arg Pro
305                 310                 315                 320

Pro Thr Pro Ala Pro Thr Ile Ala Ser Gln Pro Leu Ser Leu Arg Pro
            325                 330                 335

Glu Ala Ser Arg Pro Ala Ala Gly Gly Ala Val His Thr Arg Gly Leu
        340                 345                 350

Asp Phe Ala Ser Asp Ile Ile Ile Val Ala Val Val Ile Ala Thr Ala
        355                 360                 365

Val Ala Ala Ile Val Ala Ala Val Val Ala Leu Ile Tyr Cys Arg Lys
    370                 375                 380

Lys Arg Ile Ser Ala Asn Ser Thr Asp Pro Val Lys Ala Ala Gln Phe
385                 390                 395                 400

Glu Pro Pro Gly Arg Gln Met Ile Ala Ile Arg Lys Arg Gln Leu Glu
                405                 410                 415

Glu Thr Asn Asn Asp Tyr Glu Thr Ala Asp Gly Gly Tyr Met Thr Leu
            420                 425                 430

Asn Pro Arg Ala Pro Thr Asp Asp Asp Lys Asn Ile Tyr Leu Thr Leu
            435                 440                 445

Pro Pro Asn Asp His Val Asn Ser Asn Asn
450                 455

<210> SEQ ID NO 51
<211> LENGTH: 458
<212> TYPE: PRT
<213> ORGANISM: Artificial Sequence
<220> FEATURE:
```

<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(358)
<223> OTHER INFORMATION: Portion of CD8a linker
<220> FEATURE:
<221> NAME/KEY: MISC_FEATURE
<222> LOCATION: (359)..(380)
<223> OTHER INFORMATION: FCGR2A transmembrane domain
<220> FEATURE:
<221> NAME/KEY: MISC_FEATURE
<222> LOCATION: (381)..(458)
<223> OTHER INFORMATION: FCGR2A cytosolic domain

<400> SEQUENCE: 51

```
Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
            85                  90                  95

Ser Arg Val Glu Ala Glu Asp Ala Ala Thr Tyr Tyr Cys Gln Gln Trp
        100                 105                 110

Ser Ser Asn Pro Pro Thr Phe Gly Ser Gly Thr Lys Leu Glu Ile Lys
    115                 120                 125

Ser Gly Gly Gly Gly Ser Gly Gly Gly Ser Gly Gly Gly Gly Ser
130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
            165                 170                 175

Ala Ser Gly Phe Asn Ile Lys Asp Thr Tyr Ile His Trp Val Lys Gln
        180                 185                 190

Arg Pro Glu Gln Gly Leu Glu Trp Ile Gly Arg Ile Asp Pro Ala Asn
    195                 200                 205

Gly Asn Thr Lys Tyr Asp Pro Lys Phe Gln Gly Lys Ala Thr Ile Thr
210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
            245                 250                 255

Trp Tyr Phe Asp Val Trp Gly Ala Gly Thr Thr Val Thr Val Ser Ser
        260                 265                 270
```

```
Val Asp Leu Gly Gly Gly Gly Ser Gly Gly Gly Ser Gly Gly Gly
            275                 280                 285

Gly Ser Ser Ala Leu Ser Asn Ser Ile Met Tyr Phe Ser His Phe Val
    290                 295                 300

Pro Val Phe Leu Pro Ala Lys Pro Thr Thr Thr Pro Ala Pro Arg Pro
305                 310                 315                 320

Pro Thr Pro Ala Pro Thr Ile Ala Ser Gln Pro Leu Ser Leu Arg Pro
                325                 330                 335

Glu Ala Cys Arg Pro Ala Ala Gly Gly Ala Val His Thr Arg Gly Leu
            340                 345                 350

Asp Phe Ala Cys Asp Ile Ile Ile Val Ala Val Ile Ala Thr Ala
            355                 360                 365

Val Ala Ala Ile Val Ala Ala Val Val Ala Leu Ile Tyr Cys Arg Lys
    370                 375                 380

Lys Arg Ile Ser Ala Asn Ser Thr Asp Pro Val Lys Ala Ala Gln Phe
385                 390                 395                 400

Glu Pro Pro Gly Arg Gln Met Ile Ala Ile Arg Lys Arg Gln Leu Glu
                405                 410                 415

Glu Thr Asn Asn Asp Tyr Glu Thr Ala Asp Gly Gly Tyr Met Thr Leu
            420                 425                 430

Asn Pro Arg Ala Pro Thr Asp Asp Asp Lys Asn Ile Tyr Leu Thr Leu
            435                 440                 445

Pro Pro Asn Asp His Val Asn Ser Asn Asn
        450                 455

<210> SEQ ID NO 52
<211> LENGTH: 403
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(303)
<223> OTHER INFORMATION: IgG4 short hinge
<220> FEATURE:
<221> NAME/KEY: MISC_FEATURE
<222> LOCATION: (304)..(325)
<223> OTHER INFORMATION: FCGR2A transmembrane domain
<220> FEATURE:
<221> NAME/KEY: MISC_FEATURE
<222> LOCATION: (326)..(403)
<223> OTHER INFORMATION: FCGR2A cytosolic domain

<400> SEQUENCE: 52

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45
```

```
Ser Ser Val Ser Tyr Met His Phe Tyr Gln Gln Lys Pro Gly Ser Ser
     50                  55                  60
Pro Lys Pro Trp Ile Tyr Ala Thr Ser Asn Leu Ala Ser Gly Val Pro
 65                  70                  75                  80
Ala Arg Phe Ser Gly Ser Gly Ser Gly Thr Ser Phe Ser Leu Thr Ile
                 85                  90                  95
Ser Arg Val Glu Ala Glu Asp Ala Ala Thr Tyr Tyr Cys Gln Gln Trp
             100                 105                 110
Ser Ser Asn Pro Pro Thr Phe Gly Ser Gly Thr Lys Leu Glu Ile Lys
         115                 120                 125
Ser Gly Gly Gly Gly Ser Gly Gly Gly Gly Ser Gly Gly Gly Gly Ser
130                 135                 140
Met Ala Val Val Thr Gly Val Asn Ser Glu Val Gln Leu Gln Gln Ser
145                 150                 155                 160
Gly Ala Glu Leu Val Lys Pro Gly Ala Ser Val Lys Leu Ser Cys Thr
                165                 170                 175
Ala Ser Gly Phe Asn Ile Lys Asp Thr Tyr Ile His Trp Val Lys Gln
            180                 185                 190
Arg Pro Glu Gln Gly Leu Glu Trp Ile Gly Arg Ile Asp Pro Ala Asn
        195                 200                 205
Gly Asn Thr Lys Tyr Asp Pro Lys Phe Gln Gly Lys Ala Thr Ile Thr
    210                 215                 220
Thr Asp Thr Ser Phe Asn Thr Ala Tyr Leu Gln Leu Ser Ser Leu Thr
225                 230                 235                 240
Ser Glu Asp Thr Ala Val Tyr Tyr Cys Ala Lys Val Gly Tyr Gly His
                245                 250                 255
Trp Tyr Phe Asp Val Trp Gly Ala Gly Thr Thr Val Thr Val Ser Ser
            260                 265                 270
Val Asp Leu Gly Gly Gly Gly Ser Gly Gly Gly Gly Ser Gly Gly Gly
        275                 280                 285
Gly Ser Glu Ser Lys Tyr Gly Pro Pro Cys Pro Pro Cys Pro Ile Ile
    290                 295                 300
Ile Val Ala Val Val Ile Ala Thr Ala Val Ala Ala Ile Val Ala Ala
305                 310                 315                 320
Val Val Ala Leu Ile Tyr Cys Arg Lys Lys Arg Ile Ser Ala Asn Ser
                325                 330                 335
Thr Asp Pro Val Lys Ala Ala Gln Phe Glu Pro Pro Gly Arg Gln Met
            340                 345                 350
Ile Ala Ile Arg Lys Arg Gln Leu Glu Glu Thr Asn Asn Asp Tyr Glu
        355                 360                 365
Thr Ala Asp Gly Gly Tyr Met Thr Leu Asn Pro Arg Ala Pro Thr Asp
    370                 375                 380
Asp Asp Lys Asn Ile Tyr Leu Thr Leu Pro Pro Asn Asp His Val Asn
385                 390                 395                 400
Ser Asn Asn

<210> SEQ ID NO 53
<211> LENGTH: 509
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
```

```
<220> FEATURE:
<221> NAME/KEY: MISC_FEATURE
<222> LOCATION: (19)..(275)
<223> OTHER INFORMATION: TK1 ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(409)
<223> OTHER INFORMATION: IgG4 119 aa hinge
<220> FEATURE:
<221> NAME/KEY: MISC_FEATURE
<222> LOCATION: (410)..(431)
<223> OTHER INFORMATION: FCGR2A transmembrane domain
<220> FEATURE:
<221> NAME/KEY: MISC_FEATURE
<222> LOCATION: (432)..(509)
<223> OTHER INFORMATION: FCGR2A cytosolic domain

<400> SEQUENCE: 53
```

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
        115                 120                 125

Ser Gly Gly Gly Gly Ser Gly Gly Gly Gly Ser Gly Gly Gly Gly Ser
    130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Gly Ser Gly Gly Gly Ser Gly Gly Gly
        275                 280                 285

Gly Ser Glu Ser Lys Tyr Gly Pro Pro Cys Pro Pro Cys Pro Gly Gln
    290                 295                 300

```
Pro Arg Glu Pro Gln Val Tyr Thr Leu Pro Pro Ser Gln Glu Glu Met
305                 310                 315                 320

Thr Lys Asn Gln Val Ser Leu Thr Cys Leu Val Lys Gly Phe Tyr Pro
            325                 330                 335

Ser Asp Ile Ala Val Glu Trp Glu Ser Asn Gly Gln Pro Glu Asn Asn
        340                 345                 350

Tyr Lys Thr Thr Pro Pro Val Leu Asp Ser Asp Gly Ser Phe Phe Leu
    355                 360                 365

Tyr Ser Arg Leu Thr Val Asp Lys Ser Arg Trp Gln Glu Gly Asn Val
370                 375                 380

Phe Ser Cys Ser Val Met His Glu Ala Leu His Asn His Tyr Thr Gln
385                 390                 395                 400

Lys Ser Leu Ser Leu Ser Leu Gly Lys Ile Ile Val Ala Val Val Ile
            405                 410                 415

Ala Thr Ala Val Ala Ala Ile Val Ala Ala Val Val Ala Leu Ile Tyr
        420                 425                 430

Cys Arg Lys Lys Arg Ile Ser Ala Asn Ser Thr Asp Pro Val Lys Ala
    435                 440                 445

Ala Gln Phe Glu Pro Pro Gly Arg Gln Met Ile Ala Ile Arg Lys Arg
450                 455                 460

Gln Leu Glu Glu Thr Asn Asn Asp Tyr Glu Thr Ala Asp Gly Gly Tyr
465                 470                 475                 480

Met Thr Leu Asn Pro Arg Ala Pro Thr Asp Asp Asp Lys Asn Ile Tyr
            485                 490                 495

Leu Thr Leu Pro Pro Asn Asp His Val Asn Ser Asn Asn
            500                 505
```

```
<210> SEQ ID NO 54
<211> LENGTH: 619
<212> TYPE: PRT
<213> ORGANISM: Artificial Sequence
<220> FEATURE:
<223> OTHER INFORMATION: Chimeric antigen receptor
<220> FEATURE:
<221> NAME/KEY: SIGNAL
<222> LOCATION: (1)..(18)
<223> OTHER INFORMATION: Signal peptide
<220> FEATURE:
<221> NAME/KEY: MISC_FEATURE
<222> LOCATION: (19)..(275)
<223> OTHER INFORMATION: TK ScFv
<220> FEATURE:
<221> NAME/KEY: MISC_FEATURE
<222> LOCATION: (276)..(290)
<223> OTHER INFORMATION: GS linker
<220> FEATURE:
<221> NAME/KEY: MISC_FEATURE
<222> LOCATION: (291)..(519)
<223> OTHER INFORMATION: IgG4 long hinge
<220> FEATURE:
<221> NAME/KEY: MISC_FEATURE
<222> LOCATION: (520)..(541)
<223> OTHER INFORMATION: FCGR2A transmembrane domain
<220> FEATURE:
<221> NAME/KEY: MISC_FEATURE
<222> LOCATION: (542)..(619)
<223> OTHER INFORMATION: FCGR2A cytosolic domain

<400> SEQUENCE: 54

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30
```

```
Leu Ser Ala Ser Pro Gly Glu Lys Val Thr Met Thr Cys Arg Ala Ser
            35                  40                  45

Ser Ser Val Ser Tyr Met His Phe Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Phe Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Pro Thr Phe Gly Ser Gly Thr Lys Leu Glu Ile Lys
            115                 120                 125

Ser Gly Gly Gly Gly Ser Gly Gly Gly Gly Ser Gly Gly Gly Gly Ser
            130                 135                 140

Met Ala Val Val Thr Gly Val Asn Ser Glu Val Gln Leu Gln Gln Ser
145                 150                 155                 160

Gly Ala Glu Leu Val Lys Pro Gly Ala Ser Val Lys Leu Ser Cys Thr
                165                 170                 175

Ala Ser Gly Phe Asn Ile Lys Asp Thr Tyr Ile His Trp Val Lys Gln
            180                 185                 190

Arg Pro Glu Gln Gly Leu Glu Trp Ile Gly Arg Ile Asp Pro Ala Asn
            195                 200                 205

Gly Asn Thr Lys Tyr Asp Pro Lys Phe Gln Gly Lys Ala Thr Ile Thr
            210                 215                 220

Thr Asp Thr Ser Phe Asn Thr Ala Tyr Leu Gln Leu Ser Ser Leu Thr
225                 230                 235                 240

Ser Glu Asp Thr Ala Val Tyr Tyr Cys Ala Lys Val Gly Tyr Gly His
                245                 250                 255

Trp Tyr Phe Asp Val Trp Gly Ala Gly Thr Thr Val Thr Val Ser Ser
            260                 265                 270

Val Asp Leu Gly Gly Gly Gly Ser Gly Gly Gly Gly Ser Gly Gly Gly
            275                 280                 285

Gly Ser Glu Ser Lys Tyr Gly Pro Pro Cys Pro Pro Cys Pro Ala Pro
            290                 295                 300

Pro Val Ala Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser Gln Glu Asp Pro Glu Val Gln Phe Asn Trp Tyr Val Asp Gly
            340                 345                 350

Val Glu Val His Asn Ala Lys Thr Lys Pro Arg Glu Glu Gln Phe Gln
            355                 360                 365

Ser Thr Tyr Arg Val Val Ser Val Leu Thr Val Leu His Gln Asp Trp
            370                 375                 380

Leu Asn Gly Lys Glu Tyr Lys Cys Lys Val Ser Asn Lys Gly Leu Pro
385                 390                 395                 400

Ser Ser Ile Glu Lys Thr Ile Ser Lys Ala Lys Gly Gln Pro Arg Glu
                405                 410                 415

Pro Gln Val Tyr Thr Leu Pro Pro Ser Gln Glu Glu Met Thr Lys Asn
            420                 425                 430

Gln Val Ser Leu Thr Cys Leu Val Lys Gly Phe Tyr Pro Ser Asp Ile
            435                 440                 445
```

```
Ala Val Glu Trp Glu Ser Asn Gly Gln Pro Glu Asn Asn Tyr Lys Thr
    450             455             460

Thr Pro Pro Val Leu Asp Ser Asp Gly Ser Phe Phe Leu Tyr Ser Arg
465             470             475                     480

Leu Thr Val Asp Lys Ser Arg Trp Gln Glu Gly Asn Val Phe Ser Cys
                485             490                 495

Ser Val Met His Glu Ala Leu His Asn His Tyr Thr Gln Lys Ser Leu
            500             505             510

Ser Leu Ser Leu Gly Lys Ile Ile Ile Val Ala Val Val Ile Ala Thr
        515             520             525

Ala Val Ala Ala Ile Val Ala Ala Val Val Ala Leu Ile Tyr Cys Arg
530             535             540

Lys Lys Arg Ile Ser Ala Asn Ser Thr Asp Pro Val Lys Ala Ala Gln
545             550             555             560

Phe Glu Pro Pro Gly Arg Gln Met Ile Ala Ile Arg Lys Arg Gln Leu
            565             570             575

Glu Glu Thr Asn Asn Asp Tyr Glu Thr Ala Asp Gly Gly Tyr Met Thr
            580             585             590

Leu Asn Pro Arg Ala Pro Thr Asp Asp Asp Lys Asn Ile Tyr Leu Thr
        595             600             605

Leu Pro Pro Asn Asp His Val Asn Ser Asn Asn
610             615
```